United States Patent
Aimone et al.

(10) Patent No.: US 12,082,942 B2
(45) Date of Patent: Sep. 10, 2024

(54) WEARABLE APPARATUS FOR BRAIN SENSORS

(71) Applicant: INTERAXON INC., Toronto (CA)

(72) Inventors: Christopher Allen Aimone, Toronto (CA); Trevor Coleman, Toronto (CA); Ariel Stephanie Garten, Toronto (CA); Samuel Thomas Mackenzie, Toronto (CA)

(73) Assignee: INTERAXON INC., Toronto (CA)

( * ) Notice: Subject to any disclaimer, the term of this patent is extended or adjusted under 35 U.S.C. 154(b) by 1216 days.

(21) Appl. No.: 15/824,814

(22) Filed: Nov. 28, 2017

(65) Prior Publication Data

US 2018/0078206 A1  Mar. 22, 2018

Related U.S. Application Data

(63) Continuation of application No. 15/102,205, filed as application No. PCT/CA2015/000003 on Jan. 6, 2015, now Pat. No. 9,867,571.

(Continued)

(51) Int. Cl.
*A61B 5/00* (2006.01)
*A61B 5/291* (2021.01)

(52) U.S. Cl.
CPC ............ *A61B 5/6803* (2013.01); *A61B 5/291* (2021.01); *A61B 5/6831* (2013.01);
(Continued)

(58) Field of Classification Search
CPC ....... A61B 5/291; A61B 5/369; A61B 5/0006; A61B 5/6803; A61B 5/282; A61B 5/6814;
(Continued)

(56) References Cited

U.S. PATENT DOCUMENTS 2,503,275 A * 4/1950 Kleinman ................ G02C 5/20
351/118
3,118,962 A * 1/1964 Hammond ............... G02C 5/20
351/118
(Continued)

FOREIGN PATENT DOCUMENTS

EP  0412629 A  2/1991
GB  2396421 A  6/2004
(Continued)

OTHER PUBLICATIONS

WIPO, International Search Report and Written Opinion for International Application No. PCT/CA2015/000003 dated Mar. 23, 2015.
(Continued)

*Primary Examiner* — Joseph A Stoklosa
*Assistant Examiner* — Brian M Antiskay
(74) *Attorney, Agent, or Firm* — Norton Rose Fulbright Canada LLP

(57) ABSTRACT

A wearable apparatus for wearing on a head of a user, the apparatus has a band assembly comprising an outer band member comprising outer band ends joined by a curved outer band portion of a curve generally shaped to correspond to the users forehead; a flexible inner band member comprising inner band ends joined by a curved inner band portion of a curve generally shaped to correspond to the user's forehead, the inner band member is attached to the outer band member at least by each inner band end respectively attached to a respective one of the outer band ends; at least one brainwave sensor disposed inwardly along the curved inner band portion to provide a flexible conductive surface; and a deformable attachment that connects the flexible inner band member to the outer band, the deformable attachment allowing the inner band to conform to the user's forehead shape, the deformable attachment having a
(Continued)

biasing component to urge the at the at least one brainwave sensor towards the user's forehead when worn by the user.

20 Claims, 74 Drawing Sheets

Related U.S. Application Data

(60) Provisional application No. 61/924,020, filed on Jan. 6, 2014.

(52) U.S. Cl.
CPC .......... *A61B 5/7203* (2013.01); *A61B 5/6814* (2013.01); *A61B 2562/0215* (2017.08); *A61B 2562/125* (2013.01); *A61B 2562/164* (2013.01); *A61B 2562/166* (2013.01)

(58) Field of Classification Search
CPC ....... A61B 5/24; A61B 5/4094; A61B 5/7203; A61B 5/165; A61B 5/25; A61B 5/6868; A61B 5/259; A61B 5/4064; A61B 5/6815; A61B 5/6831
USPC ................ 600/372, 382–384, 390, 391–395, 600/544–545; 351/41
See application file for complete search history.

(56) References Cited

U.S. PATENT DOCUMENTS

| | | | |
|---|---|---|---|
| 3,241,154 A | 3/1966 | Aileo | |
| 3,402,005 A * | 9/1968 | Liautaud | G02C 5/16 351/122 |
| 3,416,858 A * | 12/1968 | Bowes | G02C 5/20 351/118 |
| 4,826,309 A * | 5/1989 | VanNeste | G02C 5/20 351/114 |
| 5,495,853 A | 3/1996 | Yasushi | |
| 5,790,228 A * | 8/1998 | Bell, III | G02C 3/003 351/111 |
| 6,193,368 B1 * | 2/2001 | George | G02C 5/16 351/114 |
| 6,955,430 B2 * | 10/2005 | Pratt | A61F 9/022 351/159.63 |
| 2004/0073129 A1 | 4/2004 | Caldwell et al. | |
| 2004/0267152 A1 | 12/2004 | Pineda | |
| 2007/0106169 A1 | 5/2007 | Fadem | |
| 2007/0225585 A1 | 9/2007 | Washbon et al. | |
| 2008/0177197 A1 | 7/2008 | Lee et al. | |
| 2009/0214060 A1 | 8/2009 | Chuang et al. | |
| 2010/0041962 A1 * | 2/2010 | Causevic | A61B 5/377 600/383 |
| 2010/0234716 A1 | 9/2010 | Engel | |
| 2011/0004089 A1 | 1/2011 | Chou | |
| 2011/0071416 A1 | 3/2011 | Terada et al. | |
| 2011/0224569 A1 * | 9/2011 | Isenhart | A61B 5/316 600/544 |
| 2012/0029336 A1 | 2/2012 | Terada et al. | |
| 2012/0190959 A1 | 7/2012 | Hayakawa et al. | |
| 2012/0226127 A1 | 9/2012 | Asjes et al. | |
| 2013/0188080 A1 * | 7/2013 | Olsson | G06F 1/163 348/333.01 |
| 2013/0317382 A1 | 11/2013 | Le | |
| 2014/0378808 A1 | 12/2014 | Lee | |

FOREIGN PATENT DOCUMENTS

| | | |
|---|---|---|
| WO | 2002071937 A1 | 9/2002 |
| WO | 2010030363 A1 | 3/2010 |
| WO | 2013126751 A1 | 8/2013 |

OTHER PUBLICATIONS

EPO, Search Report for EP Application No. 15733213.1 dated Aug. 9, 2017.
EPO, Office Action for EP Application No. 15733213.1 dated Nov. 23, 2018.
USPTO, Office Action for U.S. Appl. No. 15/102,205 dated Apr. 19, 2017.
Intellectual Property Office of Singapore, Invitation to Respond to Written Opinion dated Nov. 1, 2021 for Singapore Patent Application No. 10201709855U.
Intellectual Property Office of Singapore, Invitation to Respond to Written Opinion dated Nov. 23, 2022 for Singapore Patent Application No. 10201709855U.

* cited by examiner

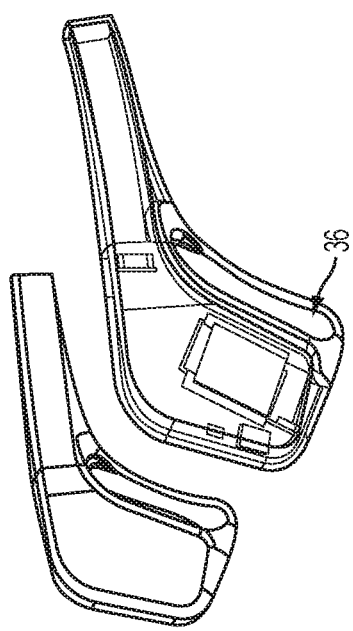
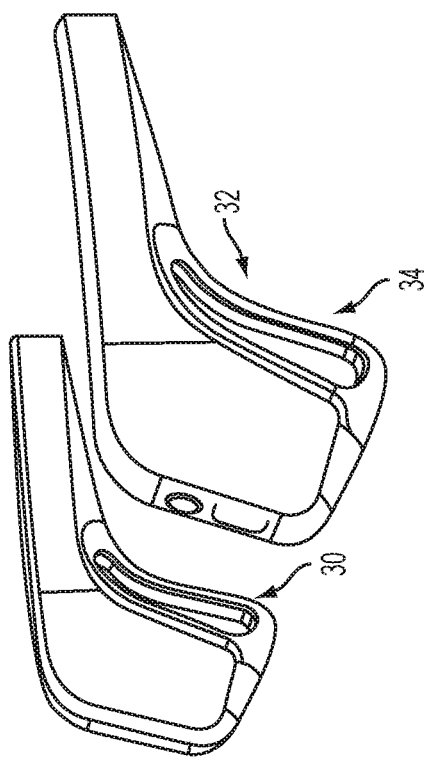
FIG. 12

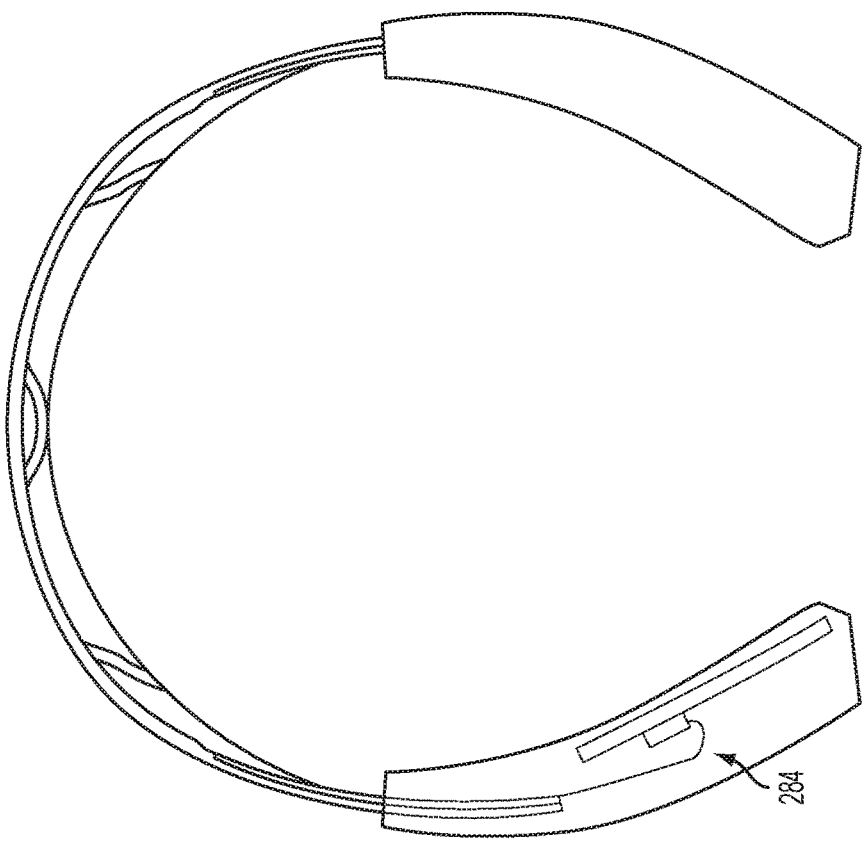
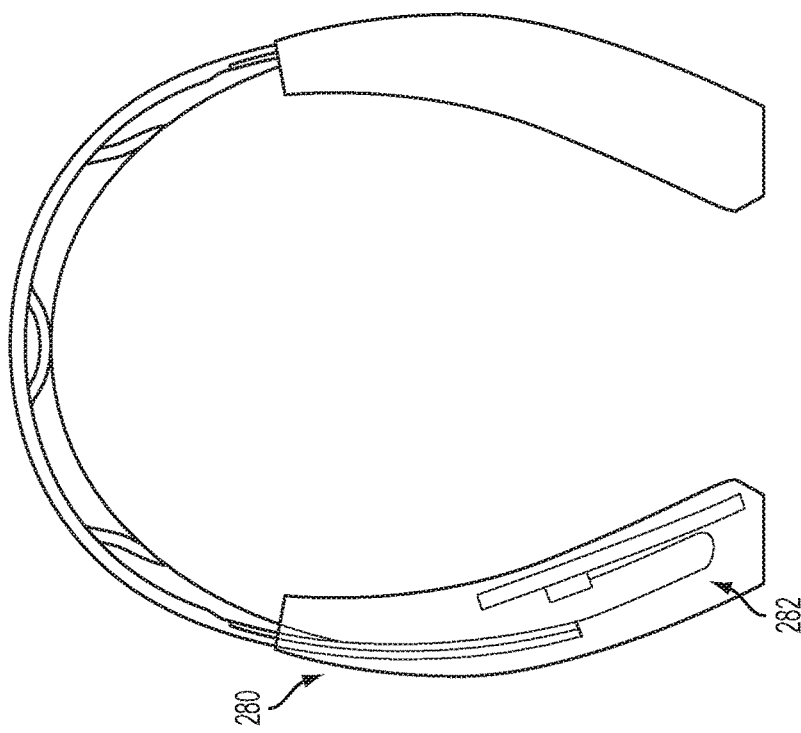
FIG. 70

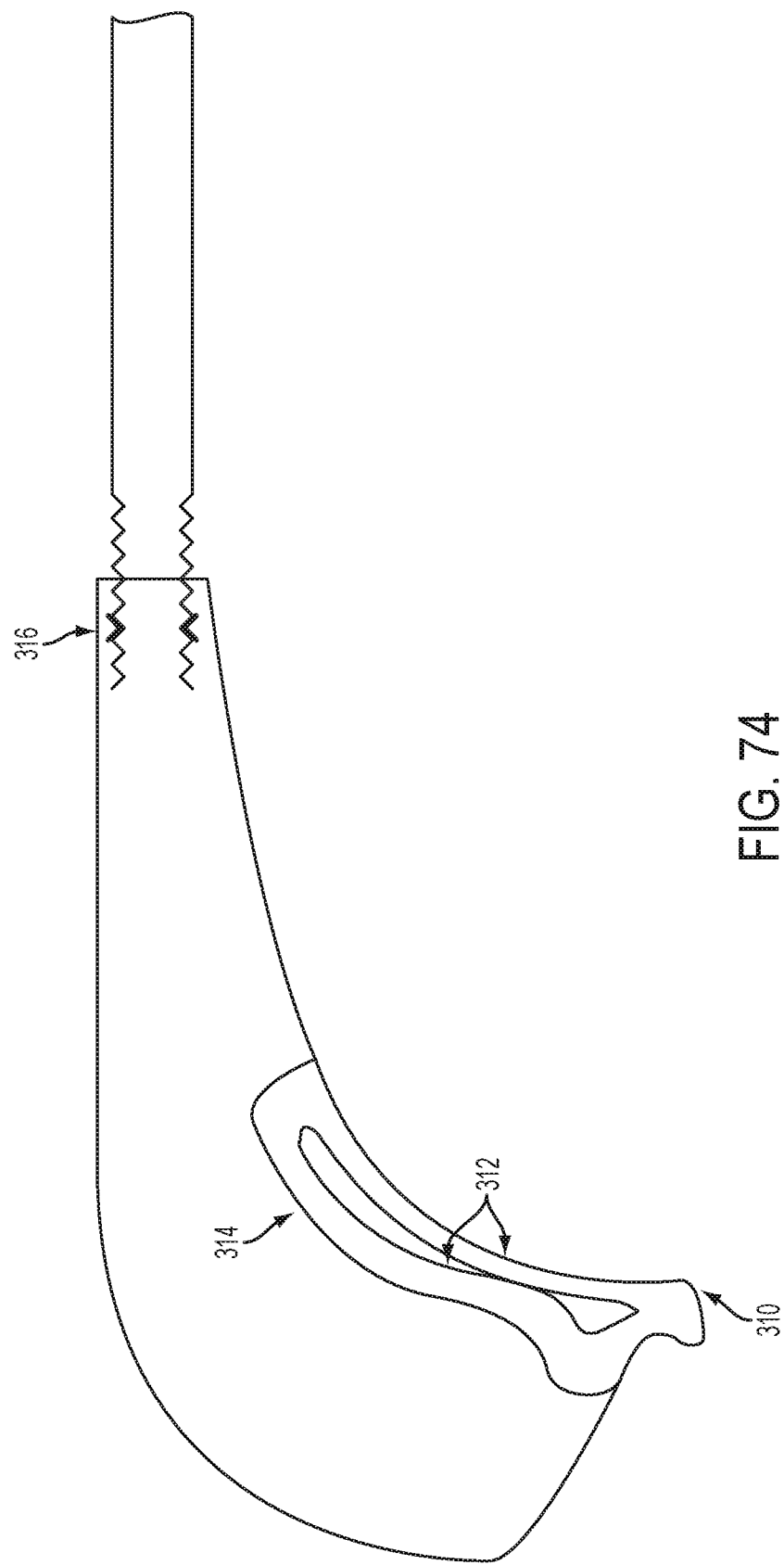

WEARABLE APPARATUS FOR BRAIN SENSORS

FIELD

Embodiments described herein relate to wearable devices. Embodiments described herein more particularly relate to wearable devices with brain sensors.

BACKGROUND

Bio-signals are signals that are generated by biological beings that can be measured and monitored. Electroencephalographs, galvanometers, and electrocardiographs are examples of devices that are used to measure and monitor bio-signals generated by humans.

A human brain generates bio-signals such as electrical patterns, which may be measured/monitored using an electroencephalogram ("EEG"). These electrical patterns, or brainwaves, are measurable by devices such as an EEG. Typically, an EEG will measure brainwaves in an analog form. Then, these brainwaves may be analyzed either in their original analog form or in a digital form after an analog to digital conversion.

Measuring and analyzing bio-signals such as brainwave patterns can have a variety of practical applications. For example, brain computer interfaces ("BCI") have been developed that allow users to control devices and computers using brainwave signals.

Monitoring brainwaves using sensors may be difficult due to challenges in obtaining an accurate, low signal to noise, brainwave signal. For example, movement of the person relative to the sensors may cause errors, or necessitate recalibration. Accordingly, there may be at least a need for improving the act of monitoring brainwaves using sensors.

SUMMARY

In accordance with an aspect, embodiments described herein may provide a wearable apparatus for wearing on a head of a user is provided, the apparatus comprising: a band assembly comprising: an outer band member comprising outer band ends joined by a curved outer band portion of a curve generally shaped to correspond to the user's forehead; an inner band member comprising inner band ends joined by a curved inner band portion of a curve generally shaped to correspond to the user's forehead, the inner band member is attached to the outer band member at least by each inner band respectively attached to a respective one of the outer band ends; at least one brainwave sensor disposed inwardly along the curved inner band portion; and biasing means disposed on the curved inner band portion at least at the at least one brainwave sensor to urge the at the at least one brainwave sensor towards the user's forehead when worn by the user.

In accordance with another aspect, embodiments described herein may provide a wearable apparatus for wearing on a head of a user, the apparatus comprises a band assembly comprising an outer band member comprising outer band ends joined by a curved outer band portion of a curve generally shaped to correspond to the users forehead; a flexible inner band member comprising inner band ends joined by a curved inner band portion of a curve generally shaped to correspond to the user's forehead, the inner band member is attached to the outer band member at least by each inner band end respectively attached to a respective one of the outer band ends; at least one brainwave sensor disposed inwardly along the curved inner band portion to provide a flexible conductive surface; and a deformable attachment that connects the flexible inner band member to the outer band, the deformable attachment allowing the inner band to conform to the user's forehead shape, the deformable attachment having a biasing component to urge the at the at least one brainwave sensor towards the user's forehead when worn by the user.

The deformable attachment may comprise a rubber spring strip that compresses along its length when the wearable apparatus is pulled tight on the user's forehead.

The deformable attachment may comprise at least one spring selected from the group consisting of a plastic leaf spring, a rubber leaf spring, a metal leaf spring, a plastic metal coil spring, a rubber metal coil spring, and a metal coil spring.

The deformable attachment may comprise foam.

The biasing component may be disposed on the curved inner band portion at least at the at least one brainwave sensor.

The deformable attachment may comprise a plurality of springs, wherein arrangement of the plurality of springs is such that when placed on the head the spring attachment provides pressure at the at least one brainwave sensor to ensure good contact with the user's head when in use.

The wearable apparatus may further comprise at least five brainwave sensors comprising an outer brainwave sensor and a central brainwave sensor, wherein the deformable attachment comprises a spring arranged at least at each of the outer brainwave sensors and at the central brainwave sensor.

The wearable apparatus may further comprise at least five brainwave sensors comprising a central brainwave sensor providing a reference measurement for other brainwave measurements, at least two brainwave sensors for providing a Driven Right Leg measurement to reduce noise of the reference measurement, at least two outer brainwave sensors for providing EEG channel measurements at FP1 and FP2 locations, and at least two earpiece brainwave sensors for providing EEG channel measurements at TP9 and TP12 locations.

The wearable apparatus may further comprise at least one earpiece shaped to secure the wearable apparatus to the user when in use, wherein the at least one earpiece comprises a conductive coating to provide at least one of the at least one brainwave sensors.

The earpiece or a portion thereof may be removable from the wearable apparatus. For example, the earpiece may include an ear pod for connected to the band assembly and a deformable earpiece portion that removably connects to the ear pod. The at least removable one earpiece may comprise a mushroom head with an attachment device that mates with a corresponding attachment device of the wearable apparatus.

The wearable apparatus may comprise at least one adjustable component to extend or retract in relation to the at least one earpiece to extend or retract that length of the band assembly.

The at least one earpiece may comprise a rubber earpiece having a mechanical holding on the back to tighten the band assembly.

The earpiece may be rubber and deformable.

The band assembly may be flexible, stretchable and twists to adjust the curve of the curved outer band portion and the curve of the curved inner band portion.

The wearable apparatus may further comprise a flexible conductive ink coating on the at least one earpiece to provide at least one of the at least one brainwave sensors.

The outer band member may comprise a rigid member.

The plurality of brainwave sensors may be configured as compressible key pad elements, each key pad element having a conductive coating that connects to a flexible circuit.

Each of the plurality of brainwave sensors may have a conductive coating that connects to a flexible circuit. The conductive coating may connect to the flexible circuit via a conductive rivet. The conductive coating may connect to the flexible circuit using mechanical pressure between the sensor and the flexible circuit. The conductive coating may connect to the flexible circuit using a hydrogel that has been hydrated with a conductive solution.

The inner band member and the outer band member may provide a stretch headband, wherein the plurality of brainwave sensors may be configured using conductive polymers.

The wearable apparatus may further comprise a semi-rigid attachment with at least one brainwave sensor attachable to the headband at a plurality of locations.

In another aspect, embodiments described herein may provide a method for connecting silver ink to flexible PCB traces of a flexible wearable apparatus to provide a conductive flexible surface comprising: creating a hatched pattern of copper on a flexible surface; creating holes in a polyamide coverlay that correspond to the copper hatched pattern; gold plating the hatched pattern of copper; printing silver ink onto the flexible surface so that adhesion between the polyimide coverlay and the silver ink keeps the silver ink on the flexible surface and the cohesive strength of the silver ink keeps it in contact with the gold plated copper.

In this respect, before explaining at least one embodiment in detail, it is to be understood that the embodiment is not limited in its application to the details of construction and to the arrangements of the components set forth in the following description or illustrated in the drawings. Other embodiments may be practiced and carried out in various ways. Also, it is to be understood that the phraseology and terminology employed herein are for the purpose of description and should not be regarded as limiting.

BRIEF DESCRIPTION OF THE DRAWINGS

Embodiments will now be described, by way of example only, with reference to the attached figures, wherein:

FIGS. 1-74 illustrate different possible embodiments of the wearable apparatus by illustrating possible diagrams for aspects of the wearable apparatus. In particular,
FIG. 1 is an example band assembly of a wearable apparatus;
FIG. 12 is an example earpiece of a wearable apparatus.

FIG. 70 is an example wearable apparatus;

FIG. 74 is an example band assembly for a wearable apparatus.

Figure 1:
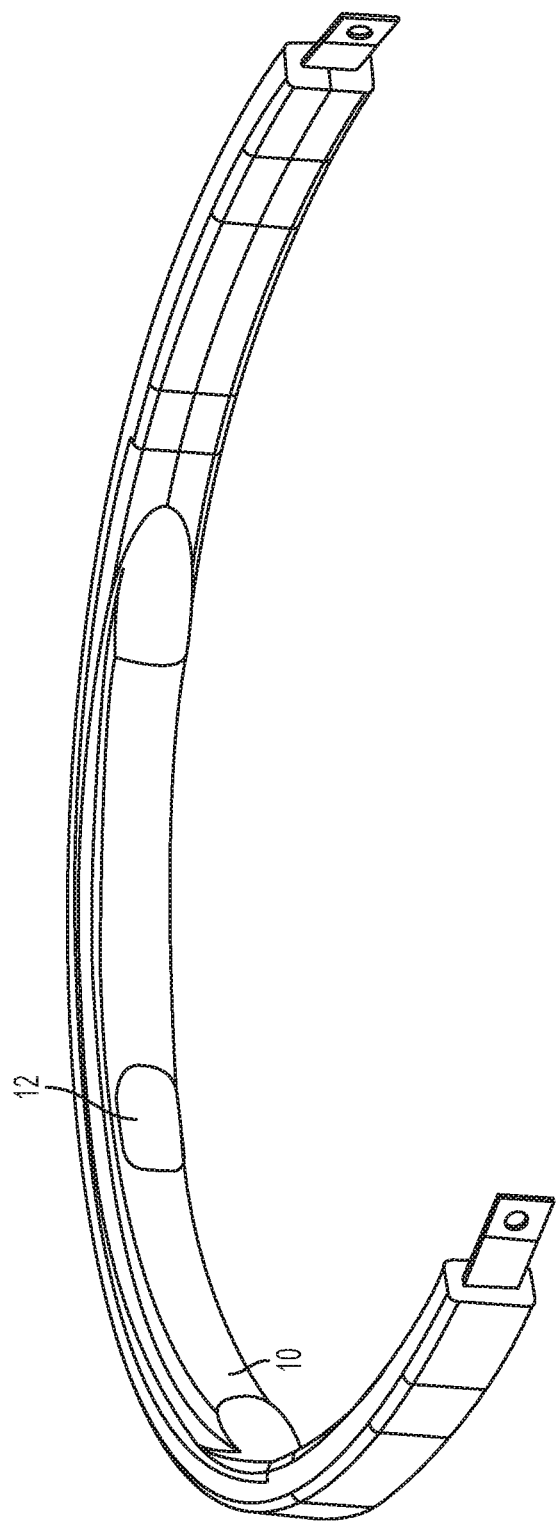

In the drawings, embodiments are illustrated by way of example. It is to be expressly understood that the description and drawings are only for the purpose of illustration and as an aid to understanding, and are not intended as a definition of the limits of the invention.

DETAILED DESCRIPTION

In accordance with an aspect, embodiments described herein provide a wearable apparatus for wearing on a head of a user is provided. The apparatus has a band assembly. The band assembly has an outer band member with outer band ends joined by a curved outer band portion of a curve generally shaped to correspond to the user's forehead. The band assembly has a flexible inner band member with inner band ends joined by a curved inner band portion of a curve generally shaped to correspond to the user's forehead. The flexible inner band member is attached to the outer band member at least by each inner band end respectively attached to a respective one of the outer band ends. At least one brainwave sensor is disposed inwardly along the curved inner band portion to provide a flexible conductive surface. A deformable attachment that connects the flexible inner band member to the outer band. The deformable attachment allows the flexible inner band to conform to the user's forehead shape. The deformable attachment has a biasing component to urge at least one brainwave sensor towards the user's forehead when worn by the user. The biasing component may be disposed on the curved inner band portion at at least the at least one brainwave sensor.

Optionally, the wearable apparatus, or headset, of the embodiments described herein may be used for collecting bio-signal data from a user for use in controlling one or more separate computing devices. The wearable apparatus may also be configured to transmit sensor data to a computing device or computer server for analysis. The wearable apparatus may also be configured to store a bio-signal interaction profile in order to analyze or process the sensor data received from the bio-signal sensors of the wearable apparatus. The profile may be updated based on the data received from the sensors or on data received from another computing device or computer server. The bio-signal data (e.g. brainwave data) may be used to determine the brain state of the user.

Optionally, the wearable apparatus of the embodiments described herein may be used to implement aspects of the systems and methods described in PCT Patent Application No. PCT/CA2013/000785, filed Sep. 16, 2013, the entirety of which is incorporated by reference herein. Accordingly, the wearable apparatus may be used with a computer network implemented system for improving the operation of one or more biofeedback computer systems. The system may include an intelligent bio-signal processing system that is operable to: capture bio-signal data and in addition optionally non-bio-signal data; and analyze the bio-signal data and non-bio-signal data, if any, so as to: extract one or more features related to at least one individual interacting with the biofeedback computer system: classify the individual based on the features by establishing one or more brain wave interaction profiles for the individual for improving the interaction of the individual with the one or more biofeedback computer systems, and initiate the storage of the brain waive interaction profiles to a database; and access one or more machine learning components or processes for further improving the interaction of the individual with the one or more biofeedback computer systems by updating automatically the brain wave interaction profiles based on detecting one or more defined interactions between the individual and the one or more of the biofeedback computer systems.

Optionally, the wearable apparatus of embodiments described herein may be used to implement aspects of the systems and methods described in POT Patent Application No. PCT/CA2013/001009, filed Dec. 4, 2013, the entirety of which is incorporated by reference herein. Accordingly, the wearable apparatus may be used with a computer system or method for modulating content based on a person's brainwave data, obtained by the sensors of the wearable apparatus of the present invention, including modifying presentation of digital content at at least one computing device. The content may also be modulated based on a set of rules maintained by or accessible to the computer system. The content may also be modulated based on user input, including through receipt of a presentation control command that may be processed by the computer system of the present invention to modify presentation of content. Content may also be shared with associated brain state information.

Some advantages of the wearable apparatus of the embodiments described herein may include achieving proper sensor placement for sensing brainwaves from a user's brain, while also being sleek and comfortable, easy to manufacture, and cost effective.

Figure 4:
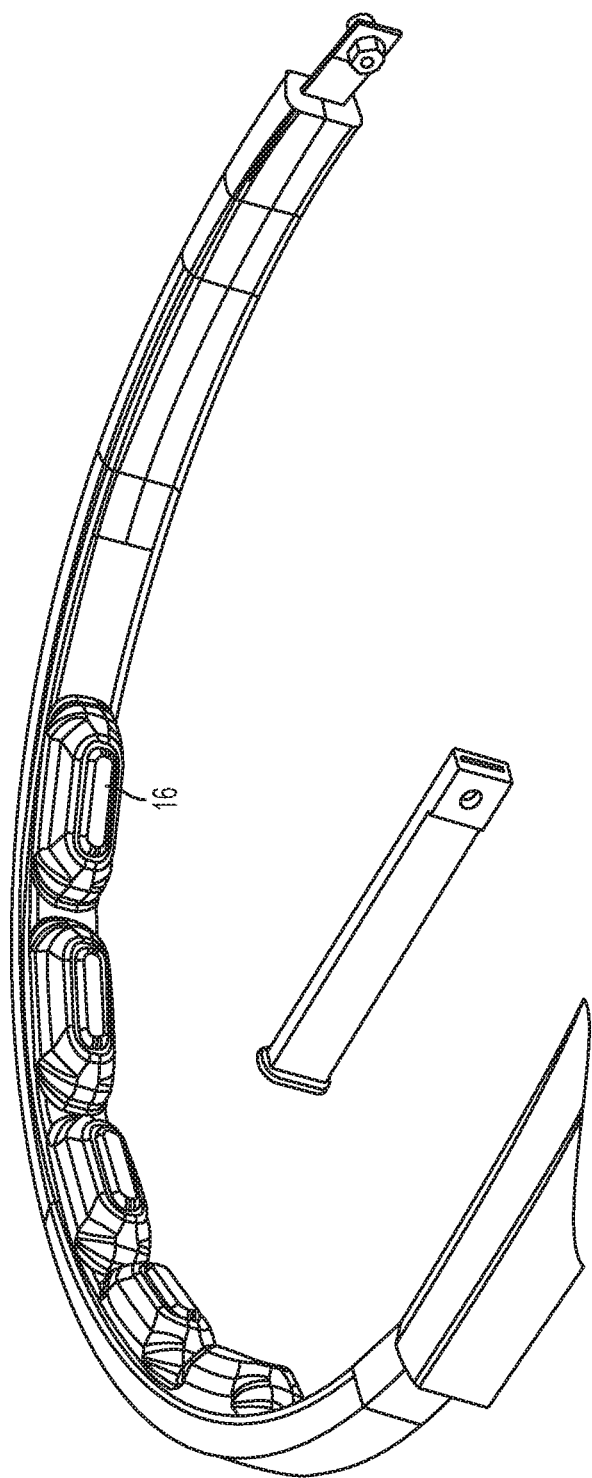
FIG. 4 is an example band assembly of a wearable apparatus.

The deformable attachment with biasing component may be a padded panel 10 that compresses when pressed against the user's forehead, as shown in FIGS. 1 and 4. Accordingly, the deformable attachment may allow the brainwave sensor, or a portion of or the entirety of the curved inner band portion to conform to the (irregular) shape of the user's head. The padded panel may provide the biasing component and may stretch along a long portion of the inner band member, or there may be an individual padded panel provided for individually suspending and biasing each brainwave sensor (electrode). The padded panel may be a compressible material, such as foam, air, gel, hydraulics, plastic, or metal spring. The padded panel is an example biasing component for the deformable attachment, and other examples including a rubber spring strip, will be described herein.

Figure 2:
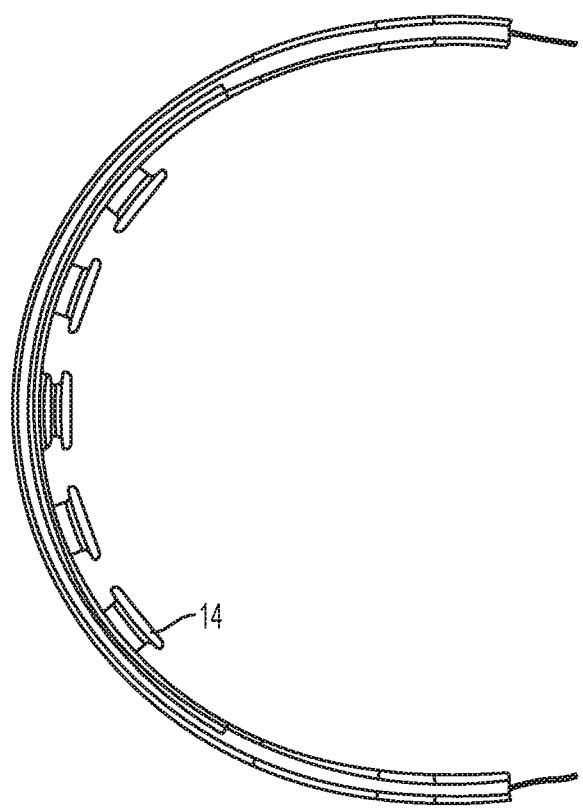
FIG. 2 is an example band assembly of a wearable apparatus.

As shown in FIG. 2, each brainwave sensor may include an electrode head 14. Each electrode head may be gimbled on the surface of the respective biasing component to conform to the angle of the head at the point of contact. Electrodes suspend individually with a compressible material underneath to provide the biasing component, such as foam, air, gel, hydraulics, plastic or metal spring.

Figure 3:
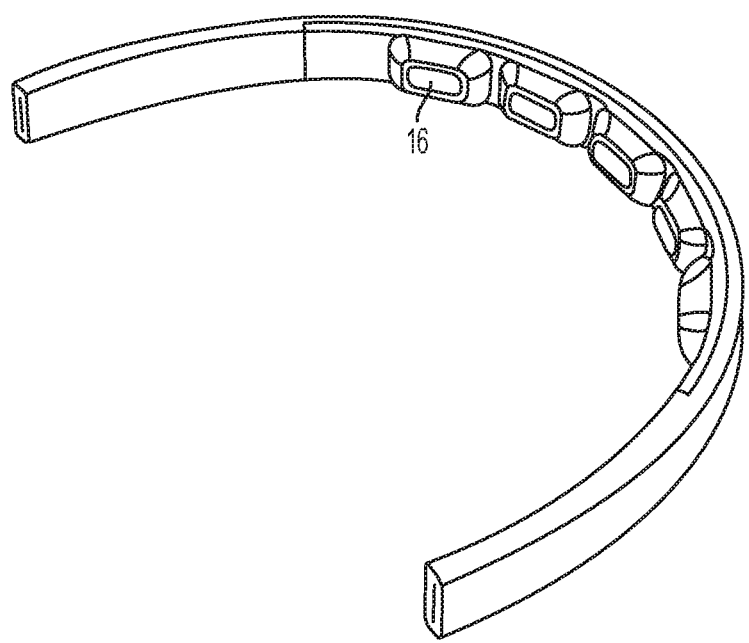
FIG. 3 is an example band assembly of a wearable apparatus.

As shown in FIGS. 3 and 4, the biasing component may be provided by a "key pad" style sensor design with "key pad" elements 16. The key pad elements 16 may be provided by individual sensors siting on rubber assemblies that collapse using a similar mechanism as a keyboard key. In this example five key pad elements 16 provide brainwave sensors for the wearable apparatus. There is a central brainwave sensor at the centre of the arrangement of key pad elements 16. There are also two outer brainwave sensors at the respective two outer key pad elements 16 at the ends of the arrangement of key pad elements 16.

Figure 5:
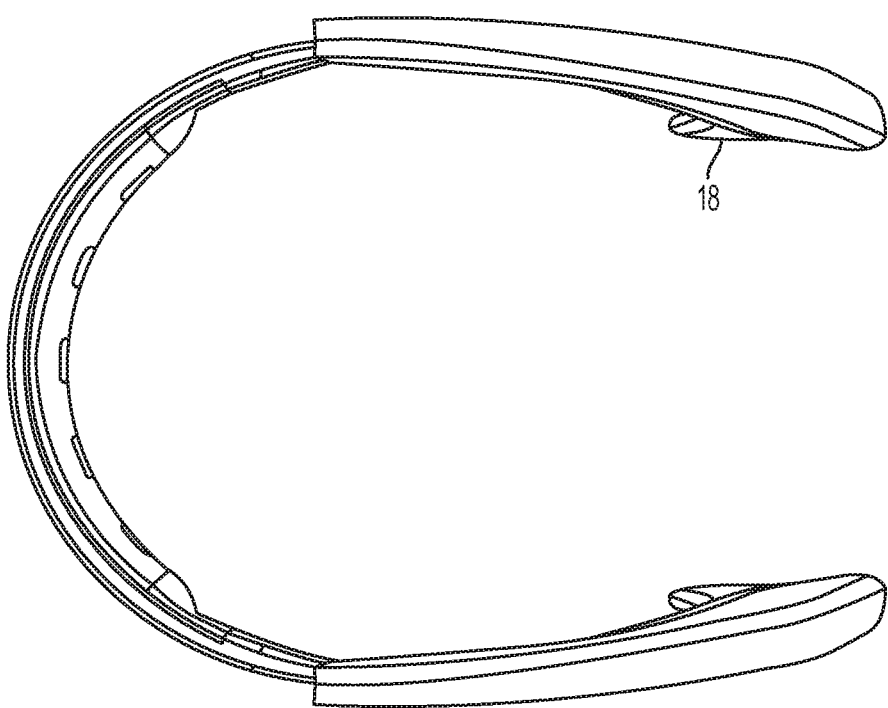
FIG. 5 is an example wearable apparatus.
Figure 6:
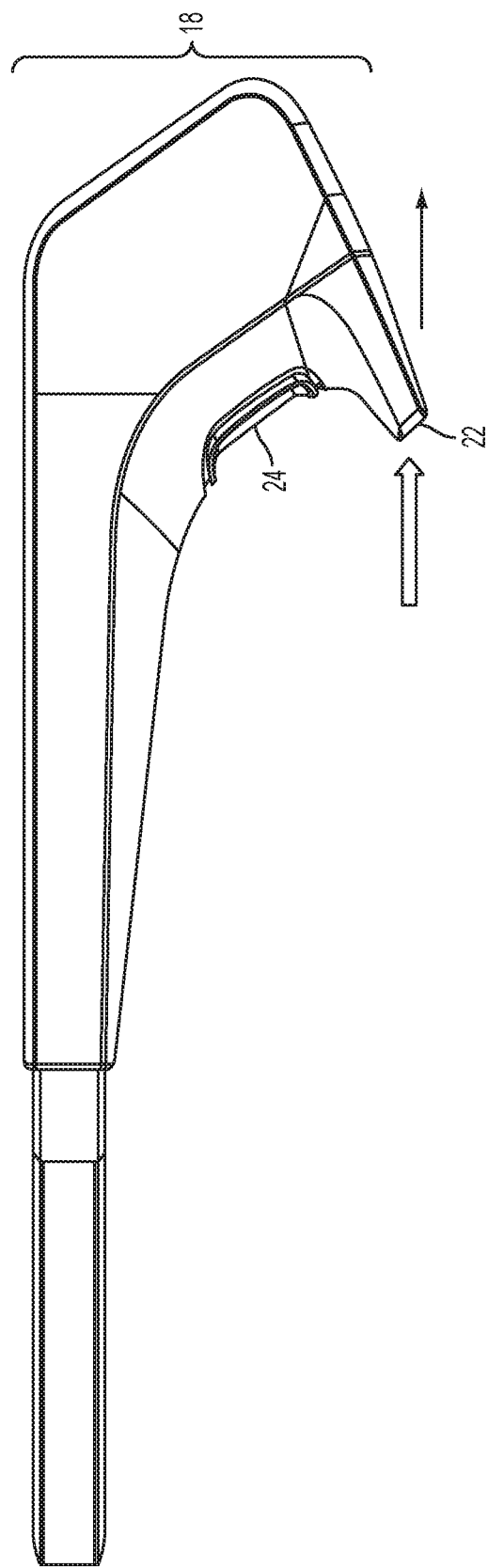
FIG. 6 is an example earpiece of a wearable apparatus.
Figure 7:
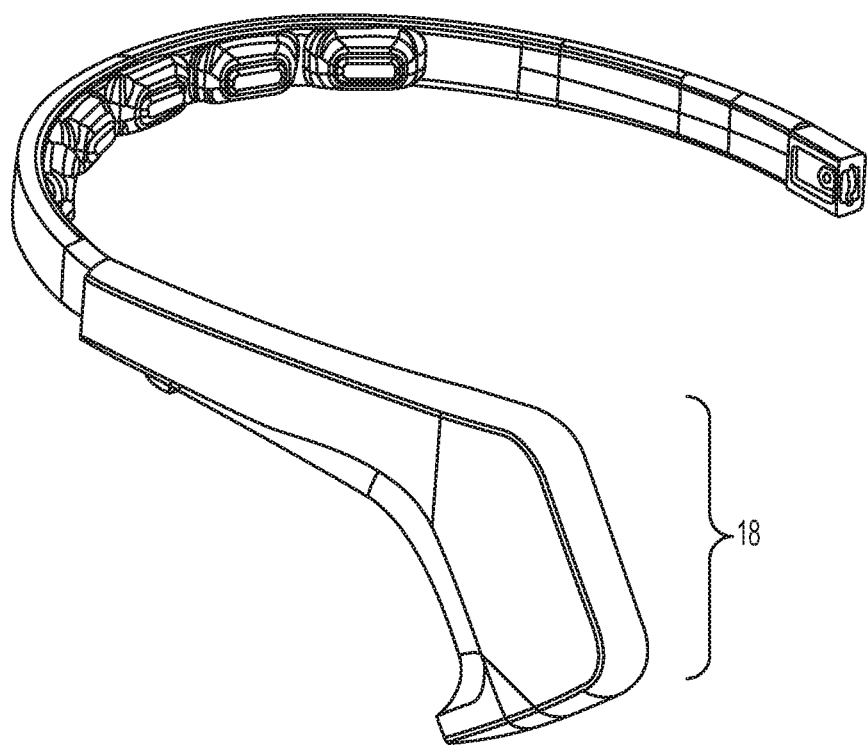
FIG. 7 is an example earpiece of a wearable apparatus.

As shown in FIGS. 5 and 6, there may be provided an earpiece 18 that is connected to the respective ends of the inner and outer bands for holding the apparatus to the user's ear. Optionally, an earpiece 18 may be provided for only one ear (as shown in FIG. 7) or for each ear (FIG. 5).

As shown in FIG. 6, the earpiece 18 may have a depressible area 24 with a thin rubber cushion, air cushion, or gel cushion that can depress against each ear may be provided, as shown in FIG. 6. The surface of the earpiece 18 or depressible area 24 may be made of metal, metal plated plastic, conductive rubber, conductive coating of silver ink, or other conductive material, in order to attempt to contact the ear without discomfort to the user.

In addition to resting on top of the user's ear, the shape of the earpiece 18 may provide a wrap portion 22 to wrap under the ear to serve to obtain a better contact below the ear, to serve to hold the headset on the head and keep it from slipping down by providing a counter balancing force at the bottom of the ear, like a hook. The wrap portion 22 can be made of conductive material that is firm or comfortable like conductive rubber.

Figure 8:
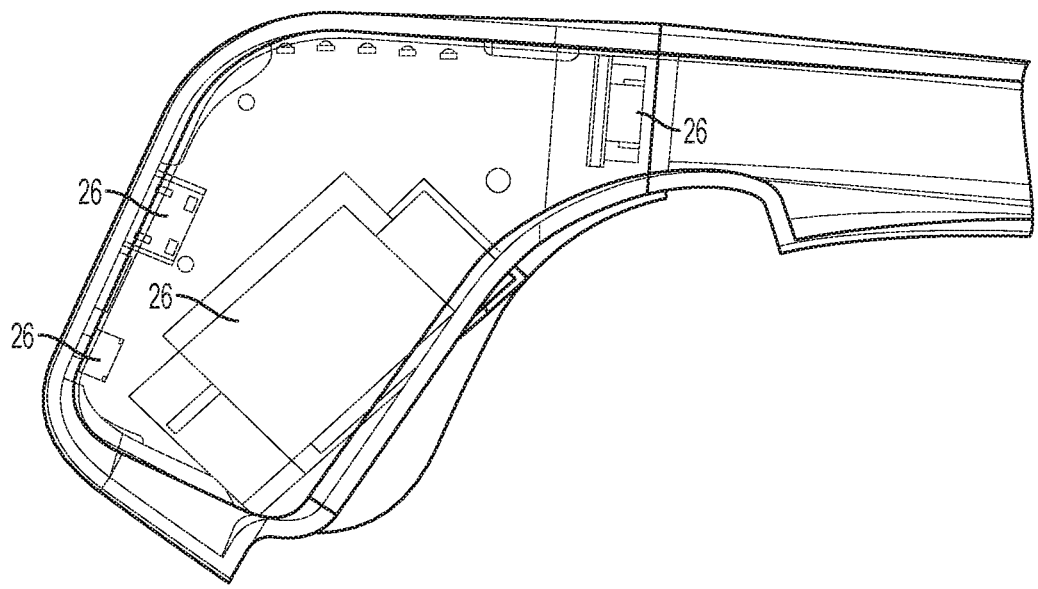
FIG. 8 is an example earpiece of a wearable apparatus.
Figure 10:
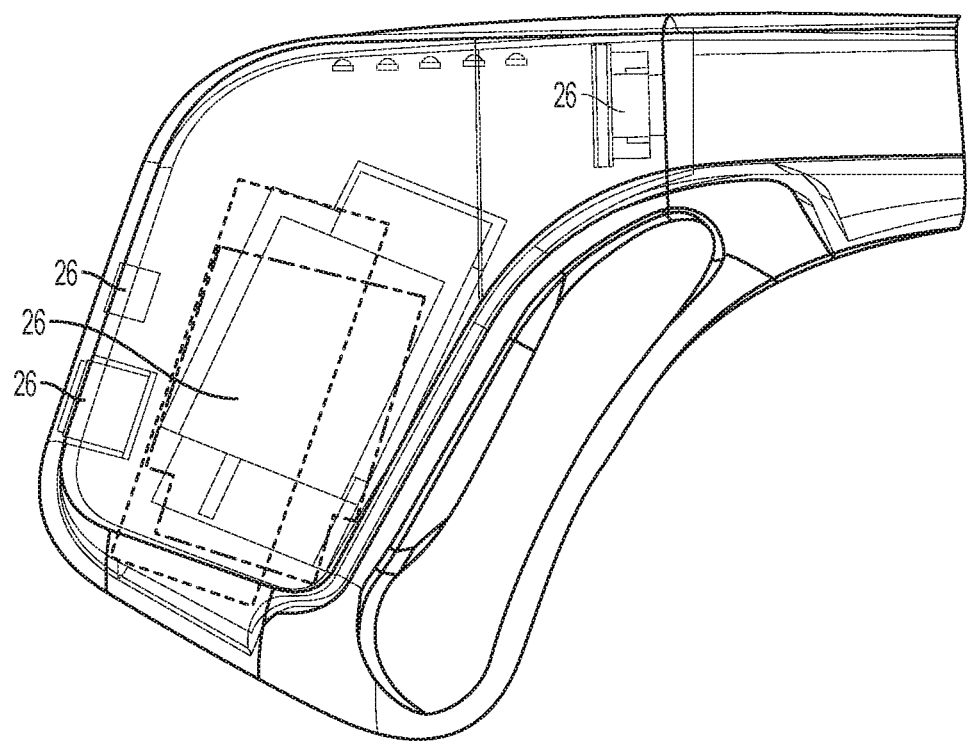
FIG. 10 is an example earpiece of a wearable apparatus.
Figure 11:
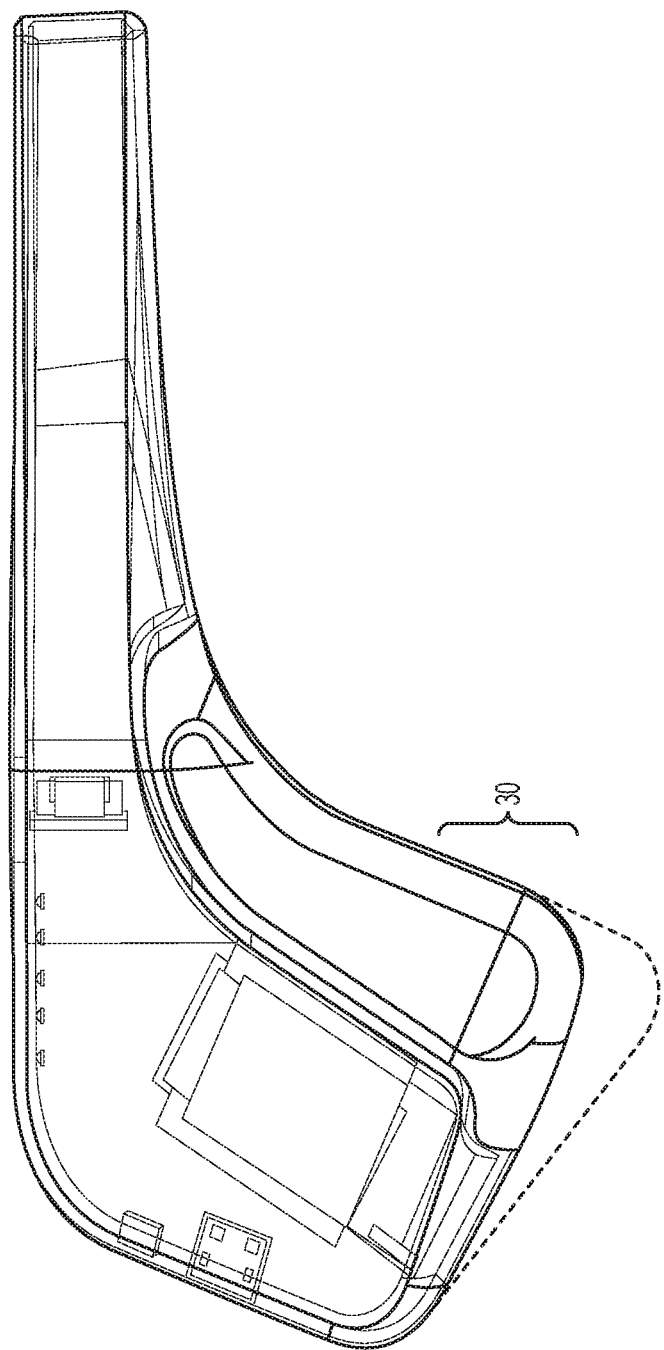
FIG. 11 is an example earpiece of a wearable apparatus.
Figure 13:
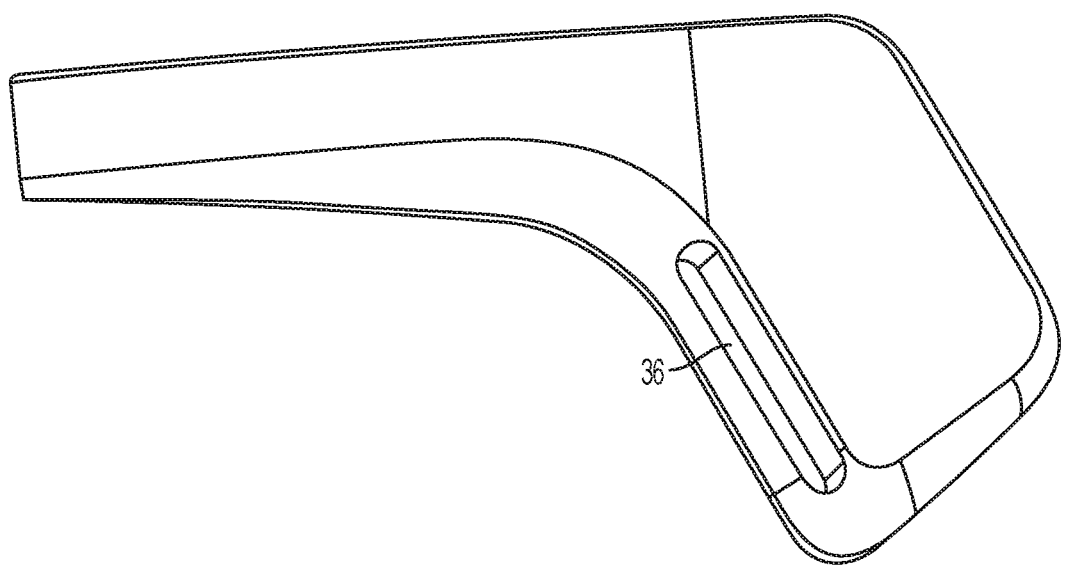
FIG. 13 is an example earpiece of a wearable apparatus.

As shown in FIGS. 8, 10, and 11, one or both earpieces may include computer electronics 26 within, namely a computer system comprising at least one computer processor, at least one (non-transitory) computer readable medium (memory) including processing instructions for the computer processor, at least one battery, and at least one communication subsystem. The computer system 26 may be connected to each brainwave sensor by communication wires, or other suitable communication means, integrated into the band assembly. Optionally, the inner band itself may be made of a conductive material, or have formed therein a conductive element used to transmit electrical signals from the brainwave sensors to the computer system 26. The communication subsystem may comprise Bluetooth™ Near-Field Communications, WiFi, or other wireless communication means for communicating with one or more computing devices, such as a mobile phone, laptop computer, desktop computer, tablet computer, or computer server.

Figure 9:
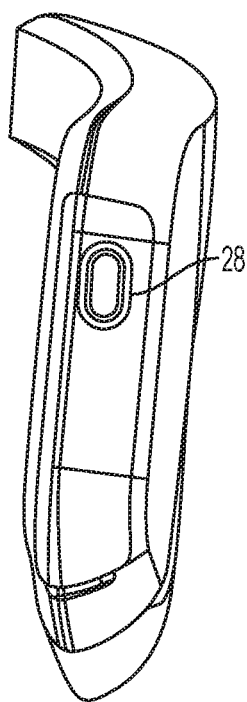
FIG. 9 is a view of an example earpiece of a wearable apparatus.

As shown in FIG. 9, the computer system 26 may also include a port 28, such as a USB port or standard or non-standard interface port for connecting the wearable apparatus to a power source for charging. The port 28 may also be used for interfacing the wearable apparatus with another computing device. The port 28 (e.g. USB port or other port) may include a cover for protecting or obscuring the USB port 28 from externalities while connected. The USB port 28 may also be used to add additional electrical parts to the wearable apparatus, such as additional conductive electrodes, either EEG, EMG, or EKG. A heart-rate monitor may also be added to the headband to affix via the USB port 28 for simultaneous EEG and EMG on one device.

As shown in FIG. 11, the shape of the bottom portion 30 of the earpiece may provide for a corner of the earpiece to not press into the back of the user's ear. As shown, a harder corner of the earpiece may help to ensure that a large portion of the shape of the earpiece does not collapse when a leading edge of the earpiece is crushed in behind the ear.

Variations of shape of the bottom portion 30 of the earpiece that contacts the user's ear are possible. The bottom portion 30 may be referred to as the contact portion. For example, as shown in FIG. 12, an inner region 36 of the earpiece contact portion may be hollowed out to be collapsible towards the portion of the earpiece housing the electronics when worn. The front edge 32 of the earpiece contact portion may be triangular to form to the groove of the user's ear. The bottom edge 34 of the earpiece contact portion may be rounded and sits below the ear so it can wrap under the ear. Comfortable conductive rubber ear contacts may be provided to provide fit to keep the headband or wearable apparatus on the head, comfort, as well as conductivity from a behind the ear electrode. Accordingly, the earpiece may also include a brainwave sensor. The rubber ear contacts may be removed or replaced to allow for different sized and shaped ears to maintain good contact and fit.

Figure 14:
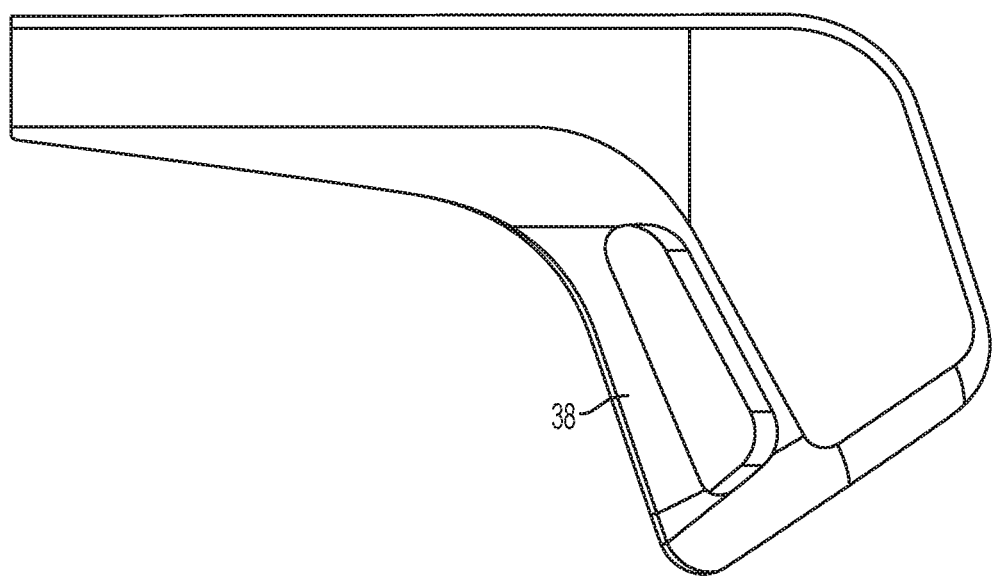
FIG. 14 is an example earpiece of a wearable apparatus.

Optionally, a smaller region 38 of the earpiece may be conductive, as shown in FIG. 14, while the rest of the earpiece material is more rigid. The smaller region 38 may be referred to as the conductive region of the earpiece.

Figure 15:
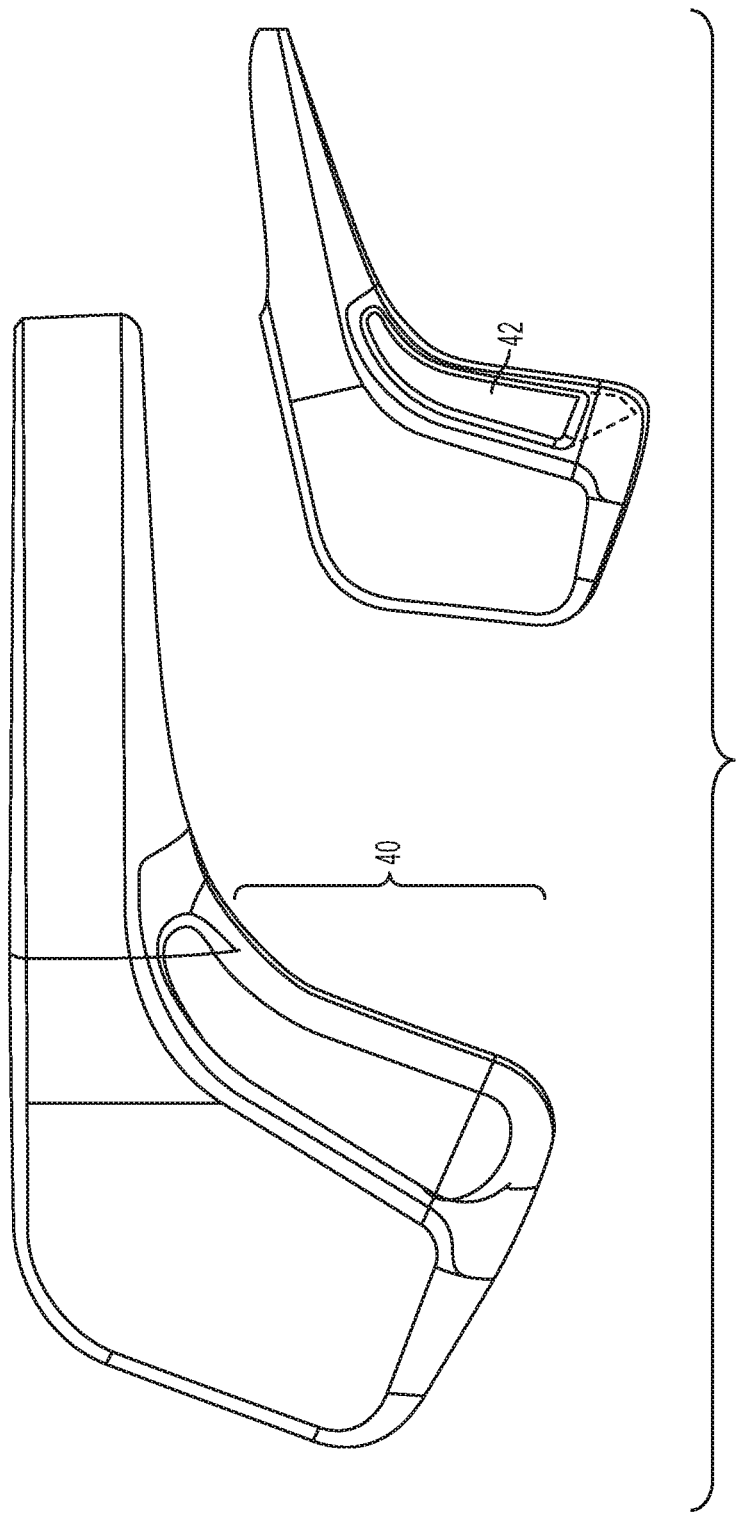
FIG. 15 is an example earpiece of a wearable apparatus.

Optionally, as shown in FIG. 15, a closed earpiece with a closed bottom portion 40 may be provided, with a hollowed-out inner portion 42 to allow additional area for collapse, increasing comfort for the user.

The outer band and inner band may be integrated into one continuous band as shown in FIGS. 1-15. The outer band may be rigid and the inner band may be flexible.

Figure 16:
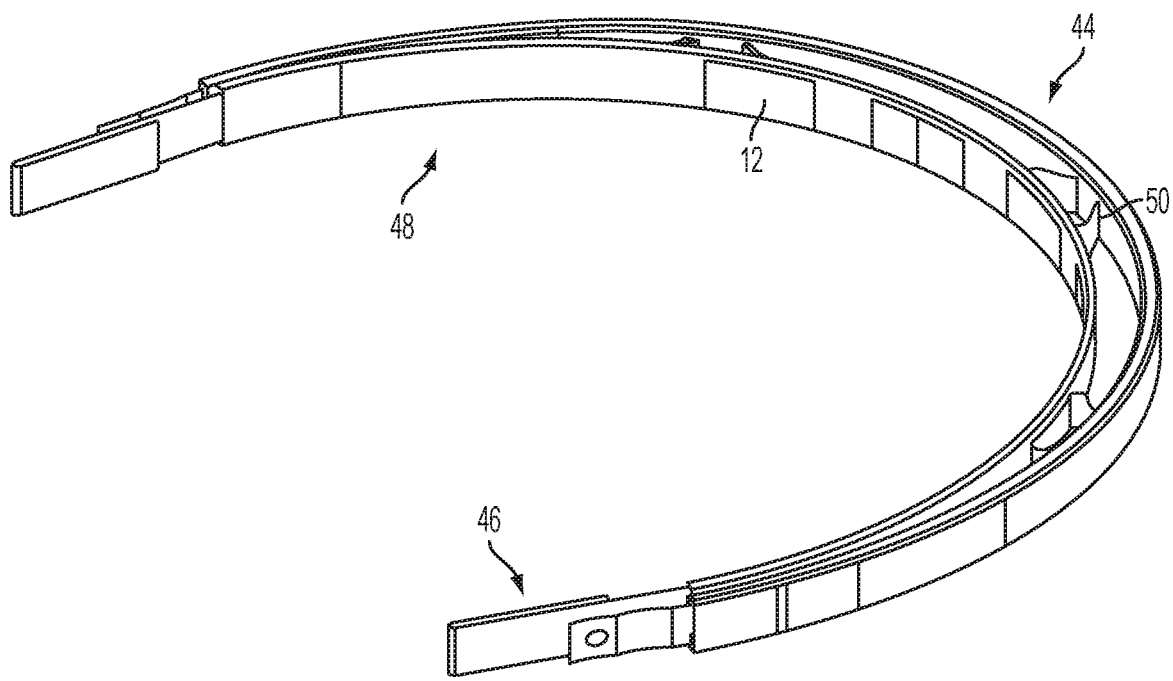
FIG. 16 is an example band assembly of a wearable apparatus.
Figure 17:
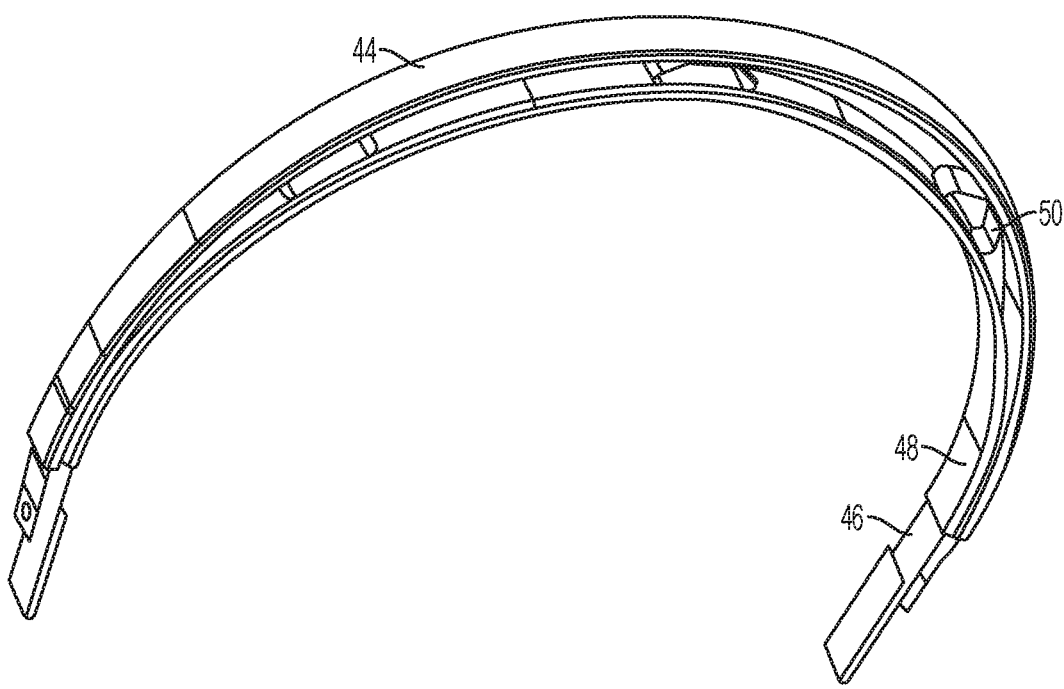
FIG. 17 is an example band assembly of a wearable apparatus.
Figure 18:
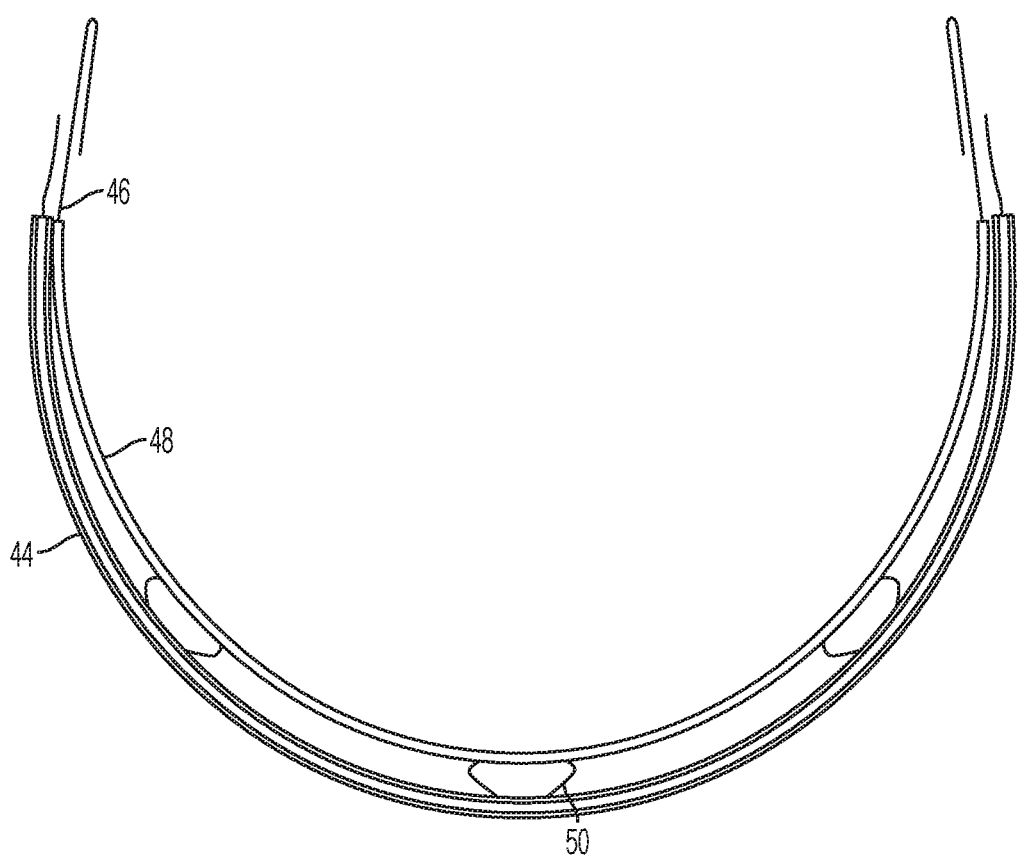
FIG. 18 is an example band assembly of a wearable apparatus.
Figure 19:
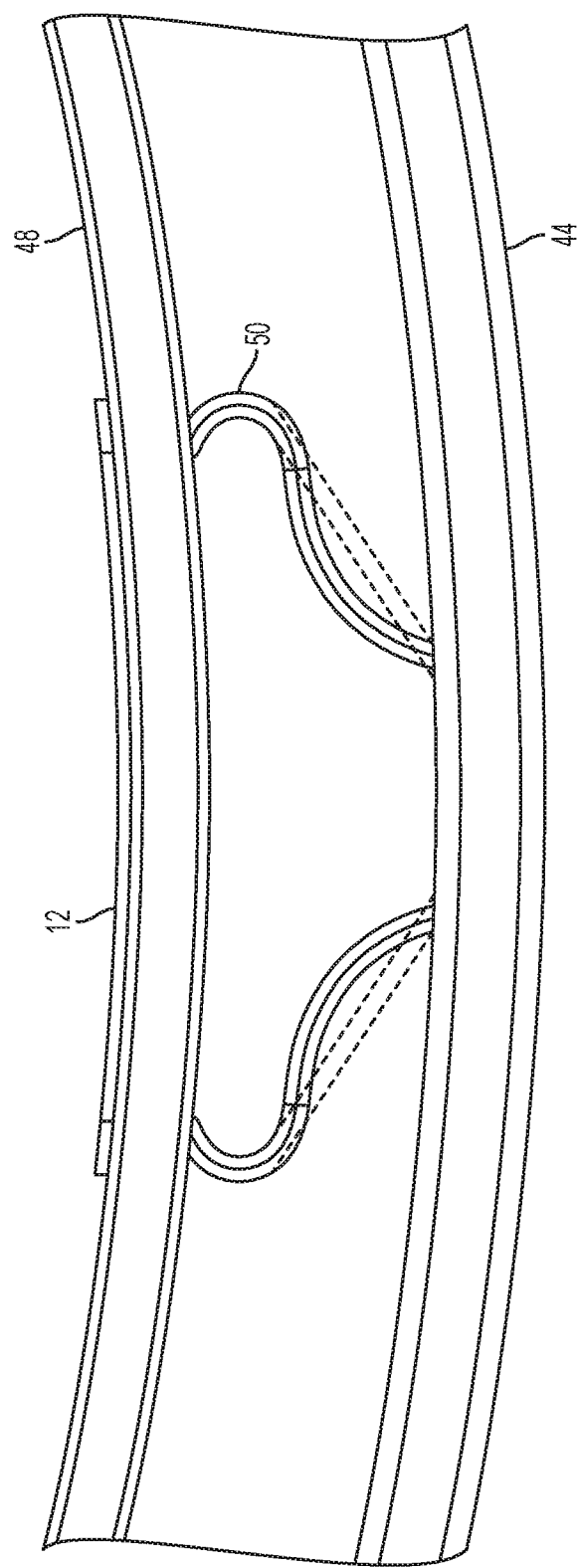
FIG. 19 is an example spring of a band assembly of a wearable apparatus.
Figure 20:
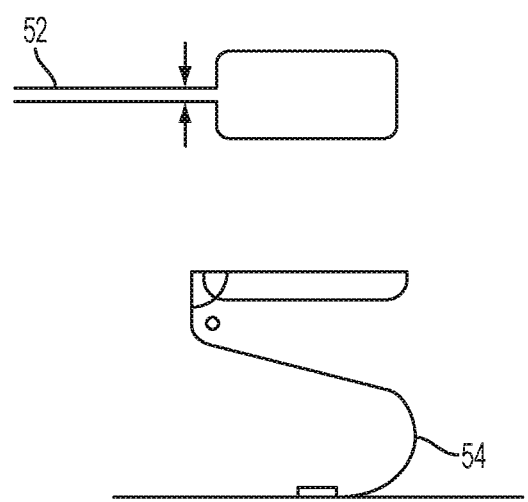
FIG. 20 is an example mount for a spring of band assembly of a wearable apparatus.

Optionally, the outer band and inner band may be formed of respective strips of material, as shown in FIGS. 16-18, and 28-29. The outer band 44 or band cover may be rigid, semi-circular or curved and made of a plastic, silicon, or other material. The inner band 48 may include a flexible printed circuit board or "Flex PCB" that has sensor 12 contacts on it. The inner band may include an interior metal band 46 with a curve shape. The inner band 48 may be flexible. The inner band 48 may be shaped to slip inside the outer band 44 and attach at the respective band ends. The inner band 48 may attach to the outer band 44 by a deformable attachment, such as springs 50. As shown in FIGS. 16-18, the inner band 48 may be supported by the outer band 44 by one or more pieces of resilient material or springs 50. Optionally, as shown, the resilient material may be shaped to form opposing spring arm 50 joining the inner and outer bands 48, 44 at oblique angles from the outer band 44. The opposing spring arms 50 may be joined by a strip of resilient material at each of the inner and outer bands 48, 44, shaped to the curves of the respective bands. When a force is applied to the inner band 48, such as from the forehead of a user of the wearable apparatus, the inner band 48 may be allowed to flex or deform towards the outer band 44 by (partially) collapsing one or more of the opposing arms 50. The opposing arms 50 may be configured to return to a rest state spacing the inner band 48 away from the outer band 44 by a particular distance, and therefore, the opposing arms 50 may bias the inner band towards the user's forehead when the opposing arms are partially collapsed by the force of the user's forehead. Accordingly, the opposing spring arms 50 may provide a biasing component. Further details of the opposing arms are shown in FIGS. 19-20. FIG. 19 provides an example illustration of how the spring arms 50 compress. In this example, the spring 50 is at a position on the band assembly that aligns or corresponds to the position of the sensor 12 on the band assembly to bias or urge the sensor 12 towards the user's head. FIG. 20 provides further details of how the spring 54 is mounted. One end of the spring 54 may be mounted to a rigid part of the band assembly and the other end of the spring 54 may be mounted against the Flex PCB. The spring 54 varies in thickness. As shown, a portion 52 of the spring 54 has a different thickness which varies the spring force. Other configurations of resilient material and springs are possible to provide a deformable attachment.

Figure 21:
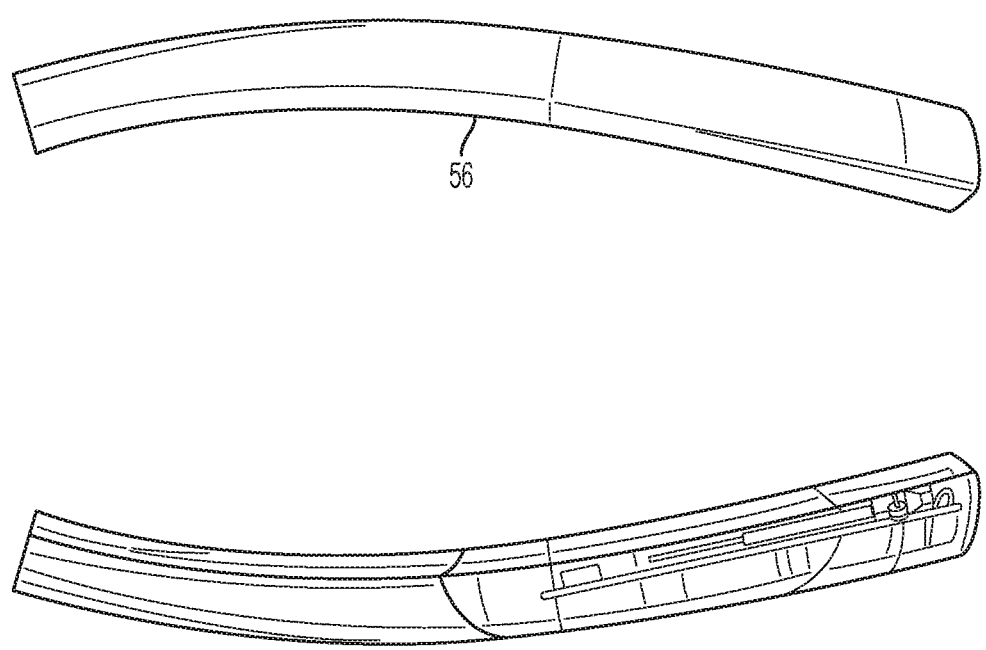
FIG. 21 is an example arm of earpiece of a wearable apparatus.
Figure 22:
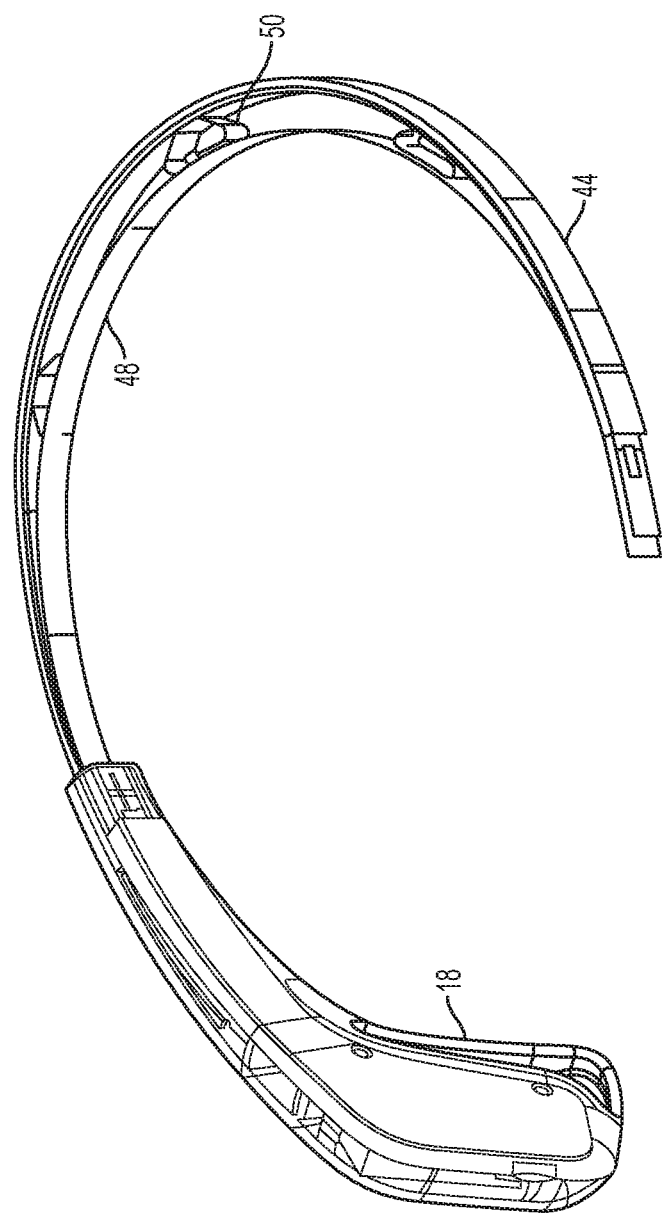
FIG. 22 is an example earpiece of a wearable apparatus.
Figure 23:
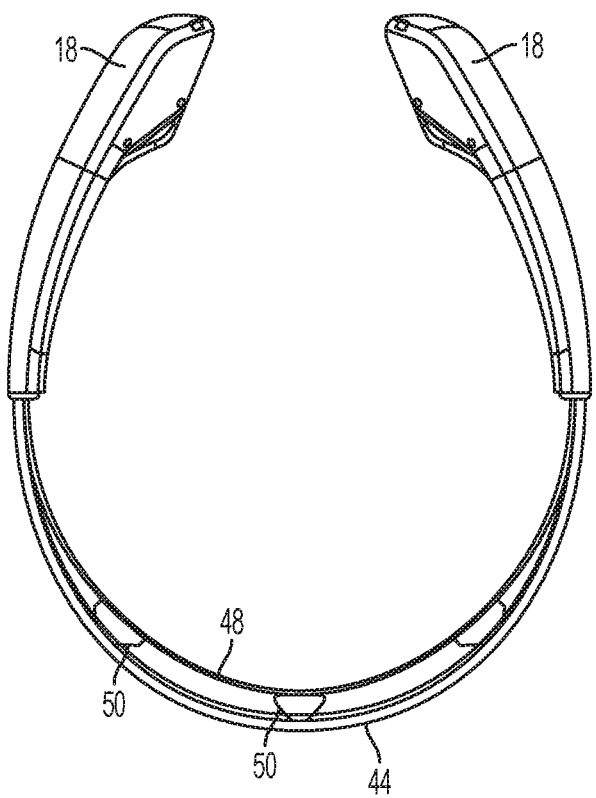
FIG. 23 is an example earpiece of a wearable apparatus.

As shown in FIGS. 6 and 7, the earpiece 18 portions may include an arm structure that may secure to ends of the inner and outer bands at the band ends. Only one earpiece 18 may contain the computer electronics 26, The other earpiece 18 may either contain no computer electronics, or may contain a battery or a second battery wired to the sensors or to the other earpiece by integrated wires, to prolong the battery life of the wearable apparatus. As shown in FIG. 21, the arm structure 56 for the earpiece 18 may be curved for comfort to conform around the user's head, and each arm can be made of a rigid material (e.g. plastic) or softer material (e.g. rubber). The arm structure 56 for the earpiece 18 may twist and flex. FIGS. 22 and 23 show an earpiece 18 connected the inner band 48 and the outer band 44. The springs 50 may provide a deformable attachment for the inner band 48 and the outer band 44. The inner band 48 and the outer band 44 may attach at end portions. The earpiece 18 may attach to the inner band 48 and the outer band 44 at an end portion by an attachment component. The attachment component may be adjustable.

Figure 24:
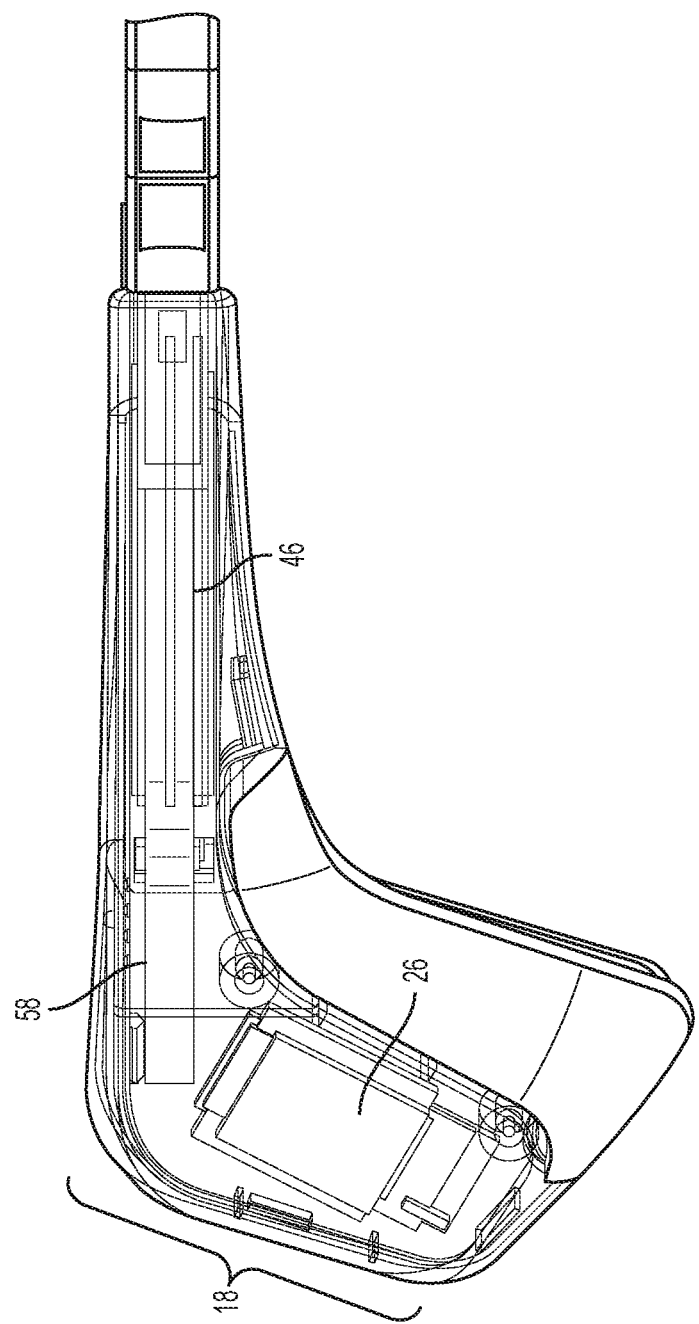
FIG. 24 is an example earpiece of a wearable apparatus.
Figure 25:
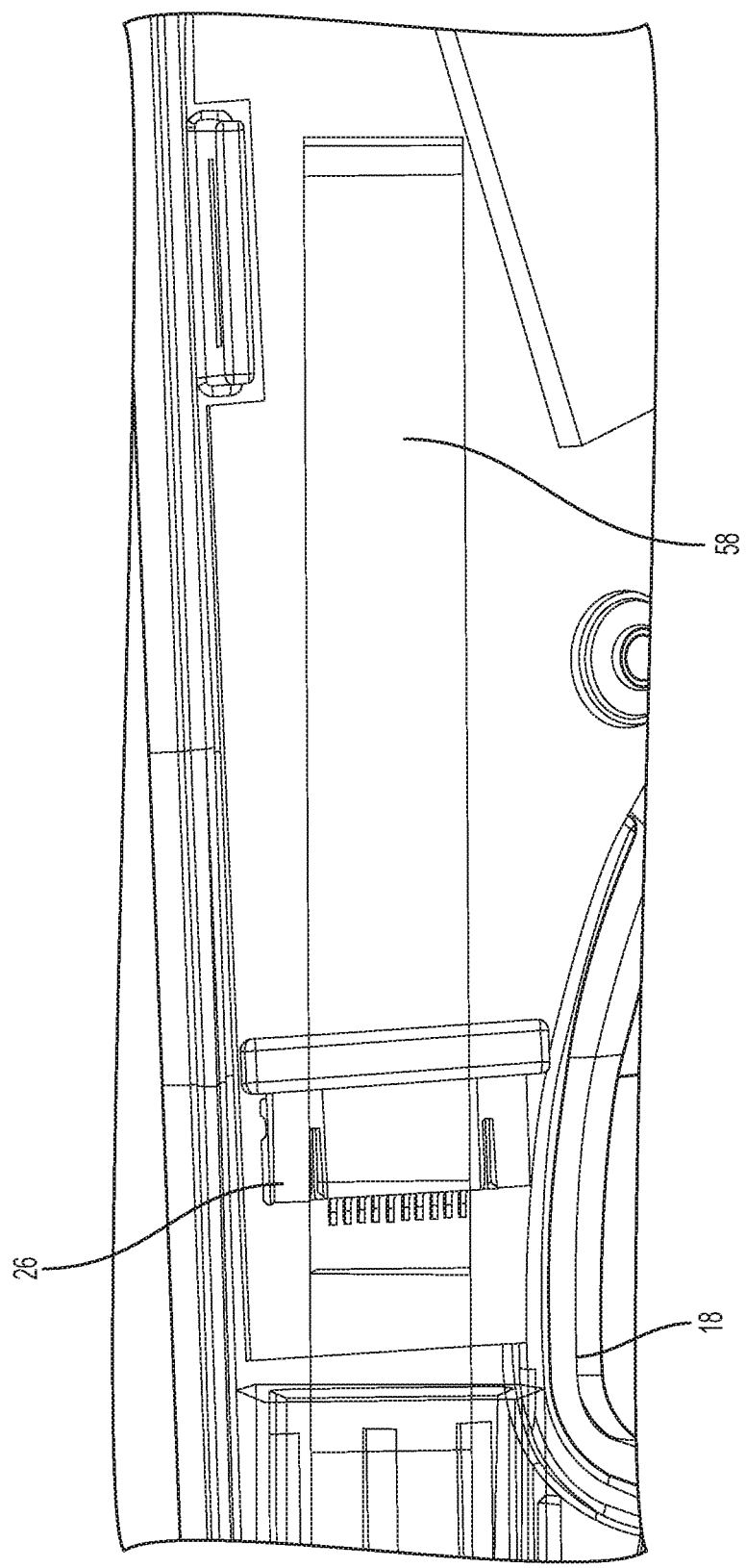
FIG. 25 is an example portion of an earpiece of a wearable apparatus.

FIG. 24 shows an internal view of how the inner band (e.g. interior metal band 46) may connect to the earpiece as shown by the end portion 58 the inner band 46. The inner band 46 has end portions 58 that connect to computer electronics via communication interface of one of the earpieces 18 for data collection from sensors. Optionally, computer electronics 26 components in each earpiece 18 are positioned lower down in the earpiece 18 to allow for clearance for the inner band end portions 58 to be fully inserted into the respective earpieces 18. Inserting an end portion 58 of the inner bands 46 into the earpiece/arm structure 18 as shown in FIG. 25 may provide for further stability of the wearable apparatus. The flex end portion 58 may match up perpendicularly to a ZIF connector.

Figure 26:
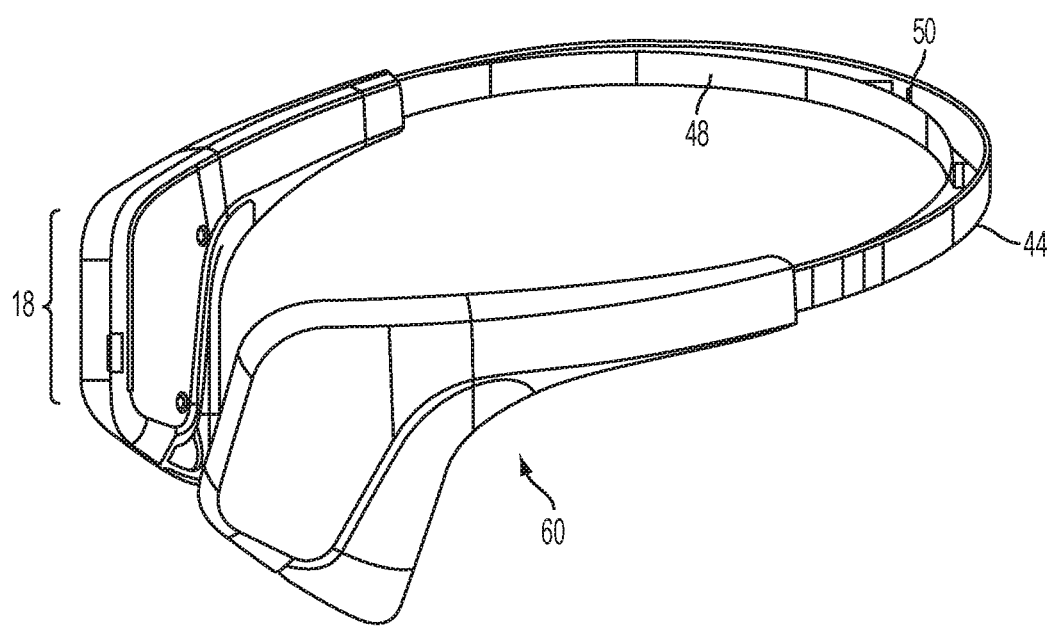
FIG. 26 is an example wearable apparatus.
Figure 27:
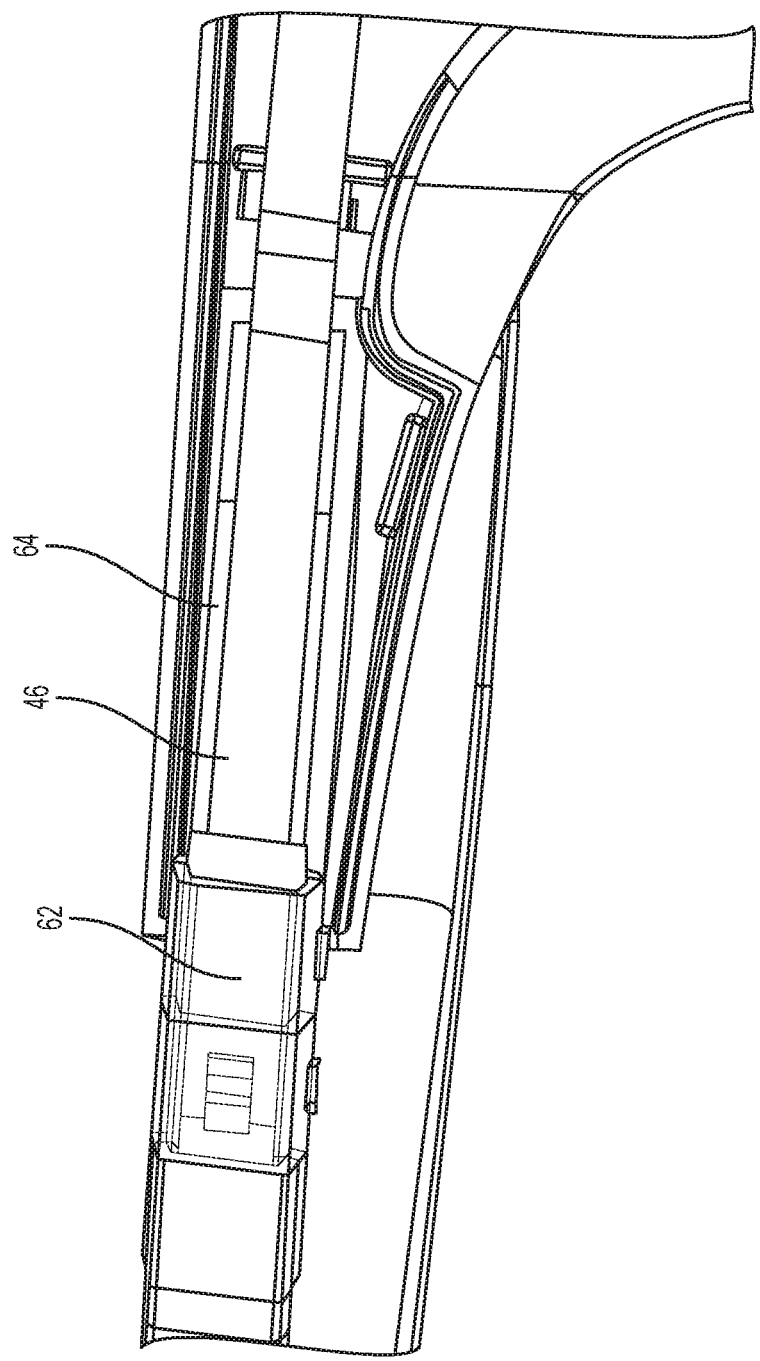
FIG. 27 is portion of an example earpiece of a wearable apparatus.

FIG. 26 shows a perspective view of an embodiment of the wearable apparatus 60 with earpieces 18. The outer band may be secured or clipped by an attachment component 62 to secure to the inner band 46 at the respective ends as shown in FIG. 27. The inner band may be held by a receiving slot 64 of the earpiece as shown in FIG. 27. The receiving slot 64 may include panels shaped to receive the end portion of the inner band 46. The receiving slot 64 may be proximate to the attachment component 62 to guide the inner band 46. The inner band may slide within the receiving slot 64 to adjust the length of the band assembly, as will be described herein.

Figure 28:
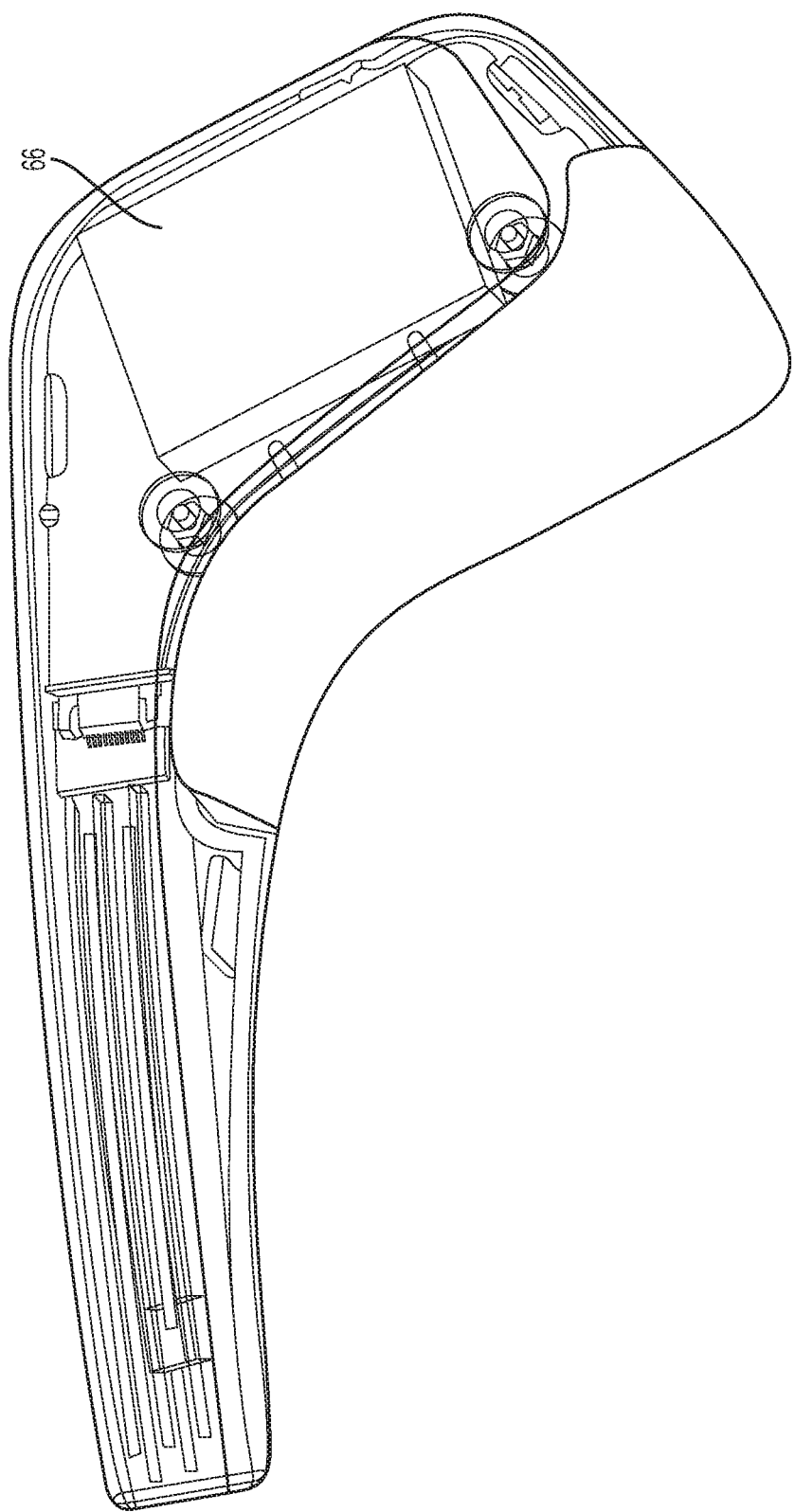
FIG. 28 is an example earpiece of a wearable apparatus.
Figure 29:
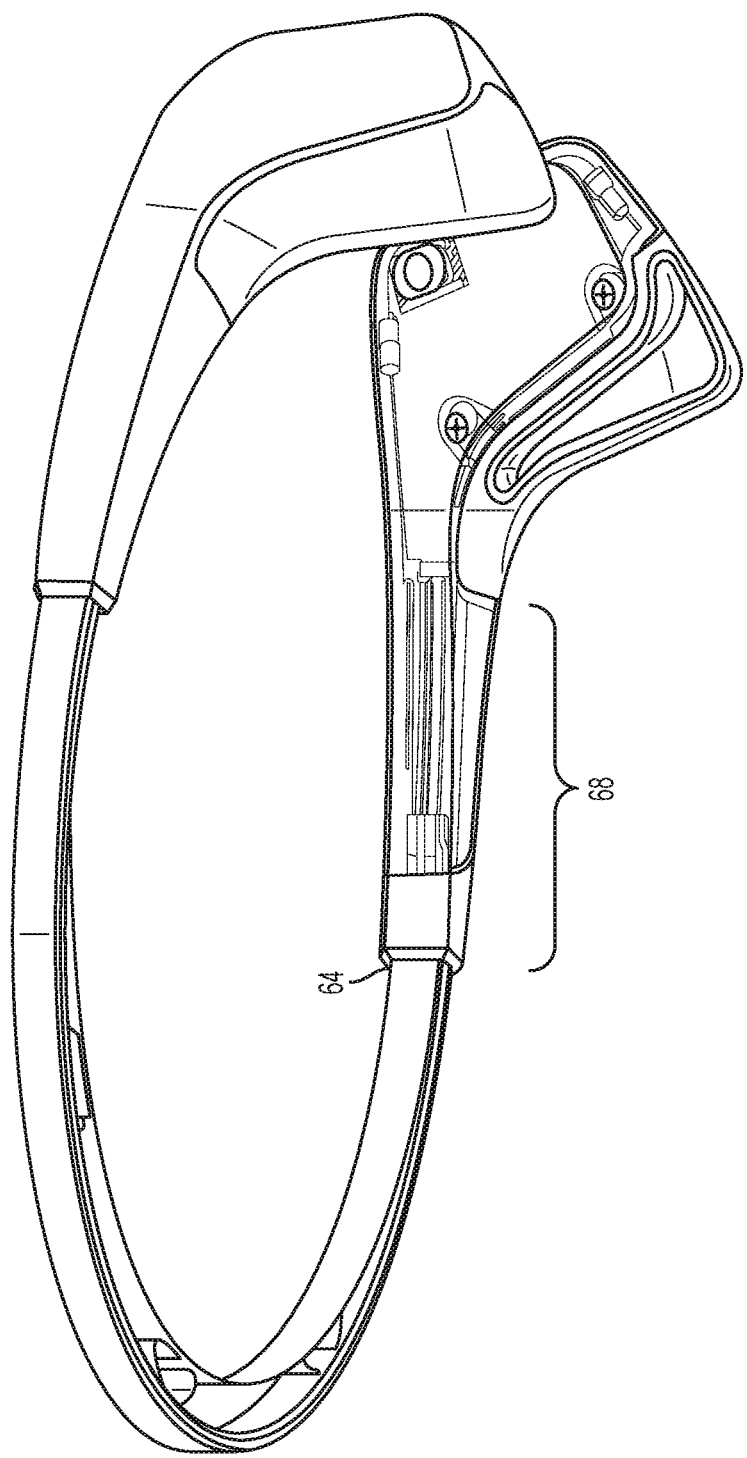
FIG. 29 is an example wearable apparatus.
Figure 30:
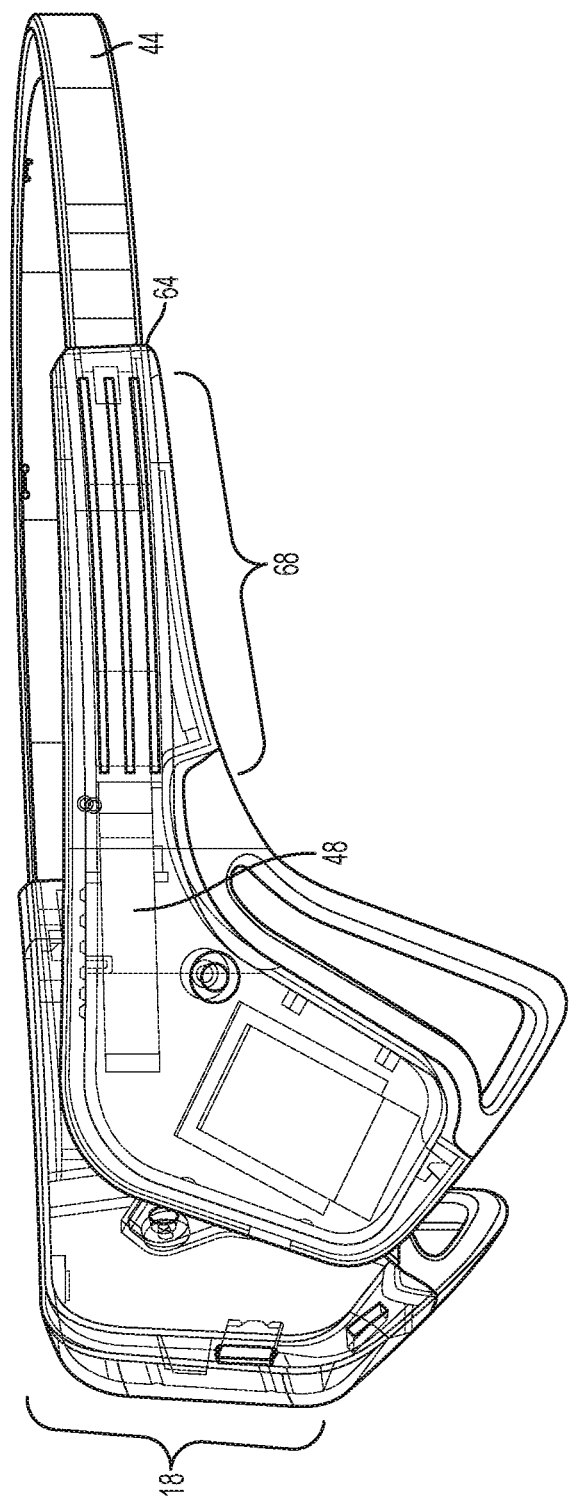
FIG. 30 is an example wearable apparatus.

FIG. 28 shows an embodiment of an earpiece of the wearable apparatus storing a battery component 66 to provide a power source for the computer electronics and sensors. The inner band end portion 48 may be inserted into this earpiece to connect to the connection port of the battery component 66 as shown in FIGS. 29-30. The receiving slot 64 is along an arm portion 68 of the earpiece. The receiving slot 64 receives the end portion 48 of the band assembly (including outer band 44) to secure to the ear piece and connect to the connection port.

Figure 31:
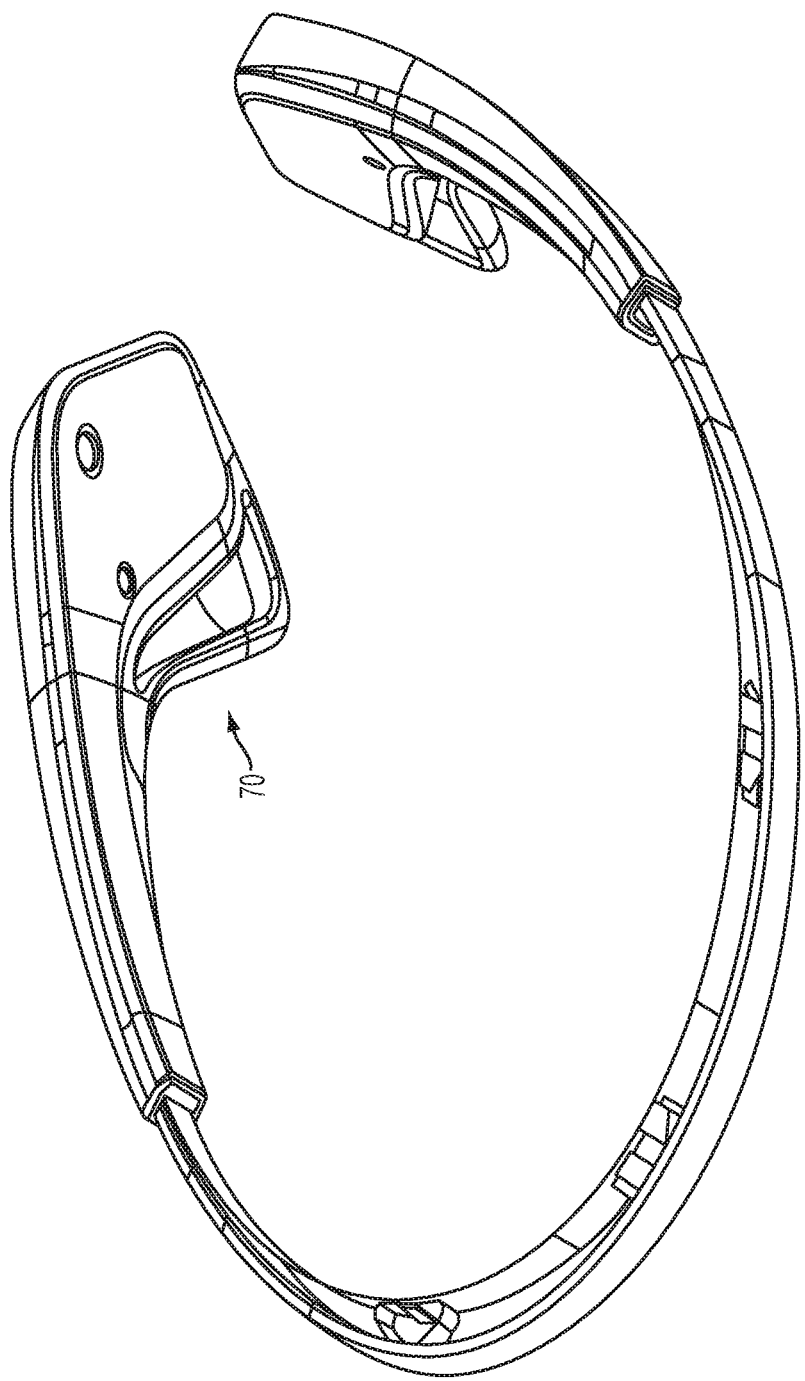
FIG. 31 is an example wearable apparatus.

As shown in FIG. 31, the arm structure 70 of the earpiece and bands may have a minor twist to bring the bottom of the inner band, earpieces and sensor contacts inwards, in order to shape along the head. The wearable apparatus may be adjustable to configure an amount of twist to provide different degrees of twist. By twisting the entire band unit, this allows the bottom of the ear pieces to move in towards the head of the user. This may provide for the wearable apparatus to conform to the user's head when it sits against the head, rather than just going straight down.

Figure 32:
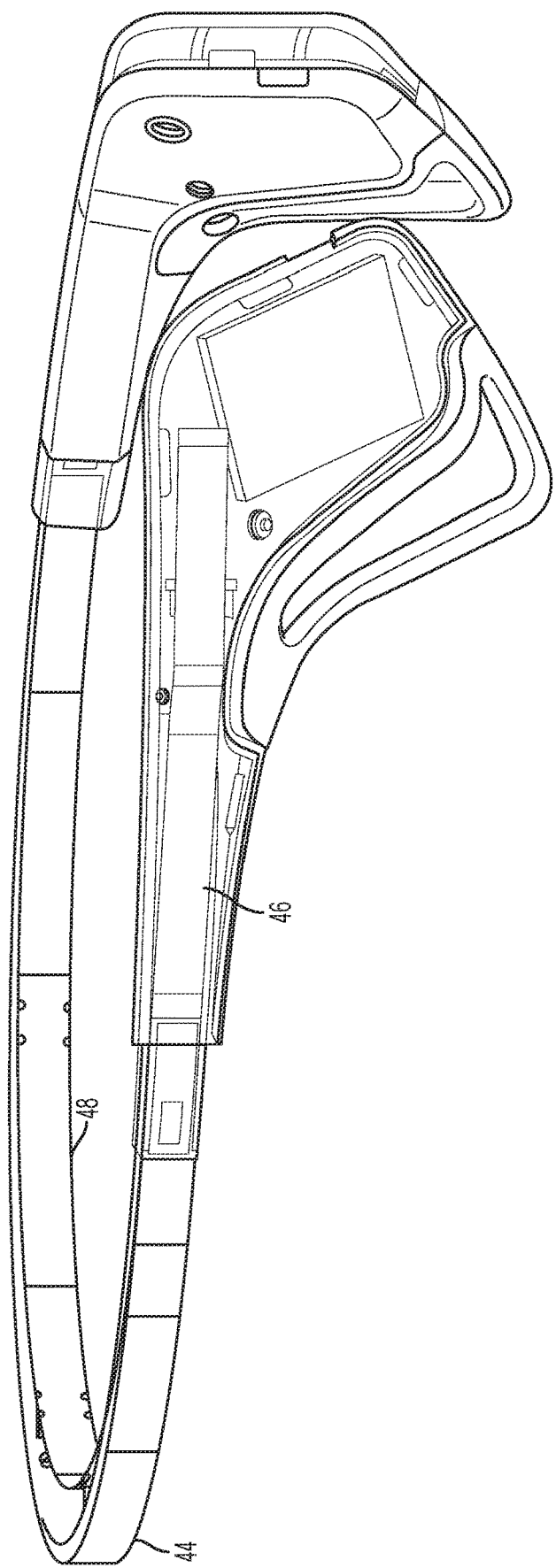
FIG. 32 is an example wearable apparatus.
Figure 33:
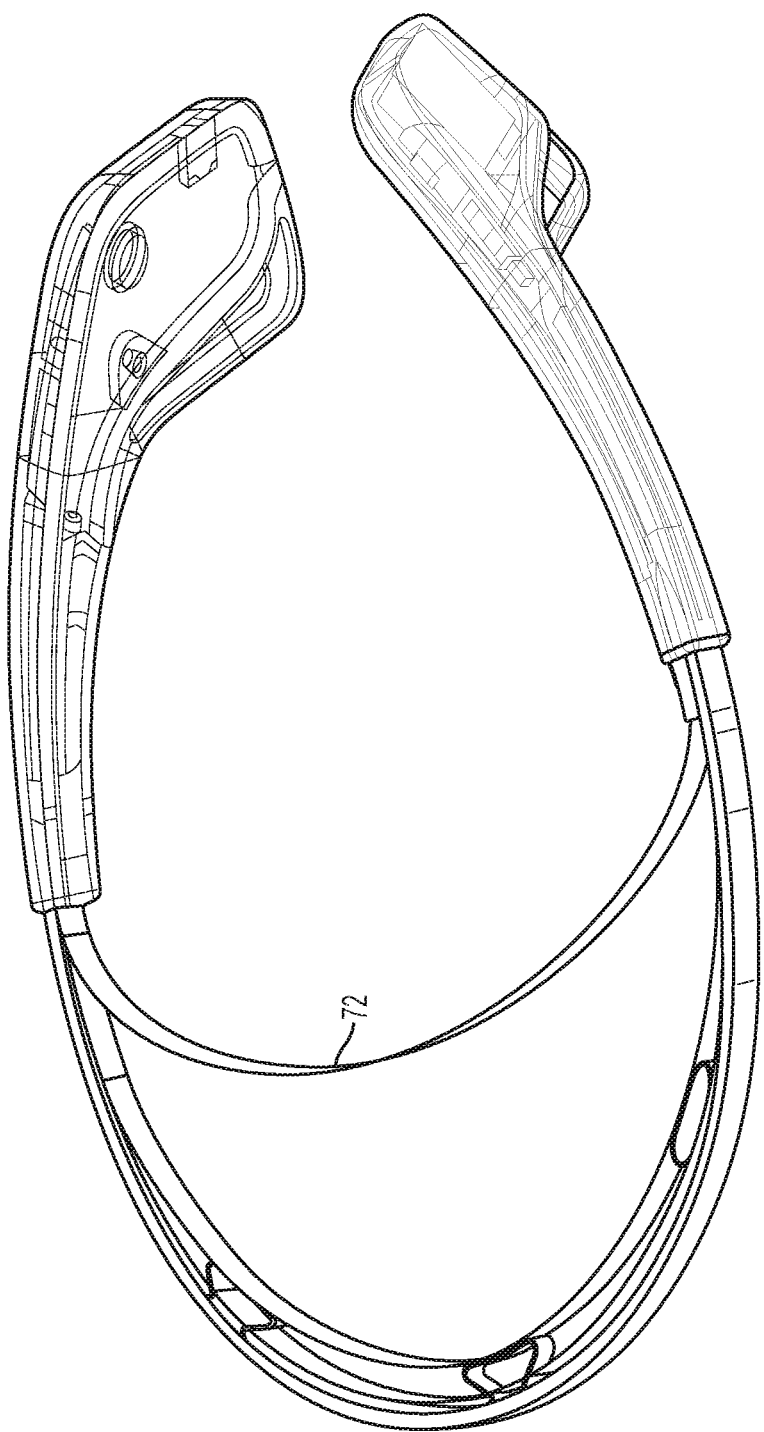
FIG. 33 is an example wearable apparatus.

FIG. 32 shows an optional shape of the bands 44, 46 and Flex PCB cover 48, particularly the inner band 46 within the earpiece. FIG. 33 shows the position of the band 72 when it is adjusted for the smallest size and fully retracted.

Figure 34:
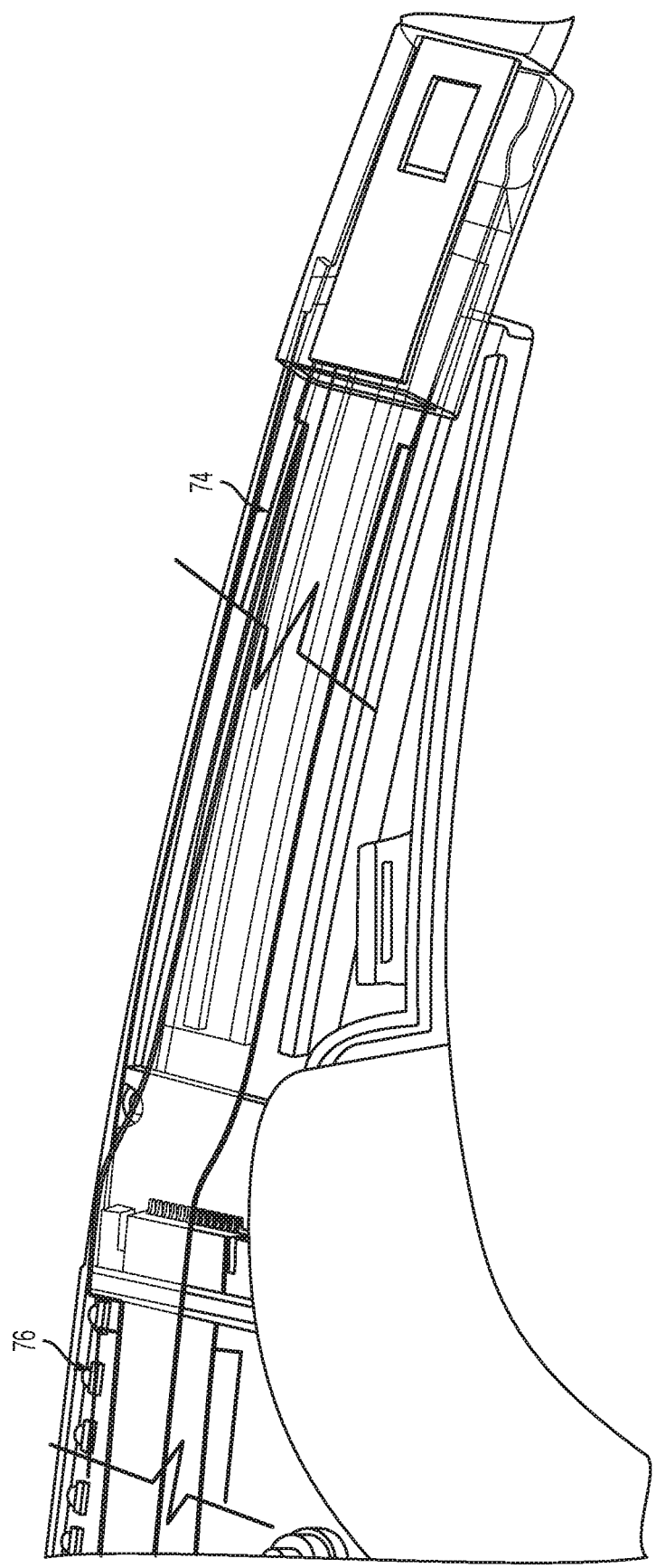
FIG. 34 is a portion of an example band assembly for a wearable apparatus.

The inner band 46 may have an approximately consistent width and thickness for its entire length, or the width or thickness may be reduced at the portion of the inner band that is received within the earpiece, as shown in FIG. 34. A portion 74 of the inner band may connect to a communication interface 76 of electronics (e.g. ZIF connector) in the earpiece.

Figure 35:
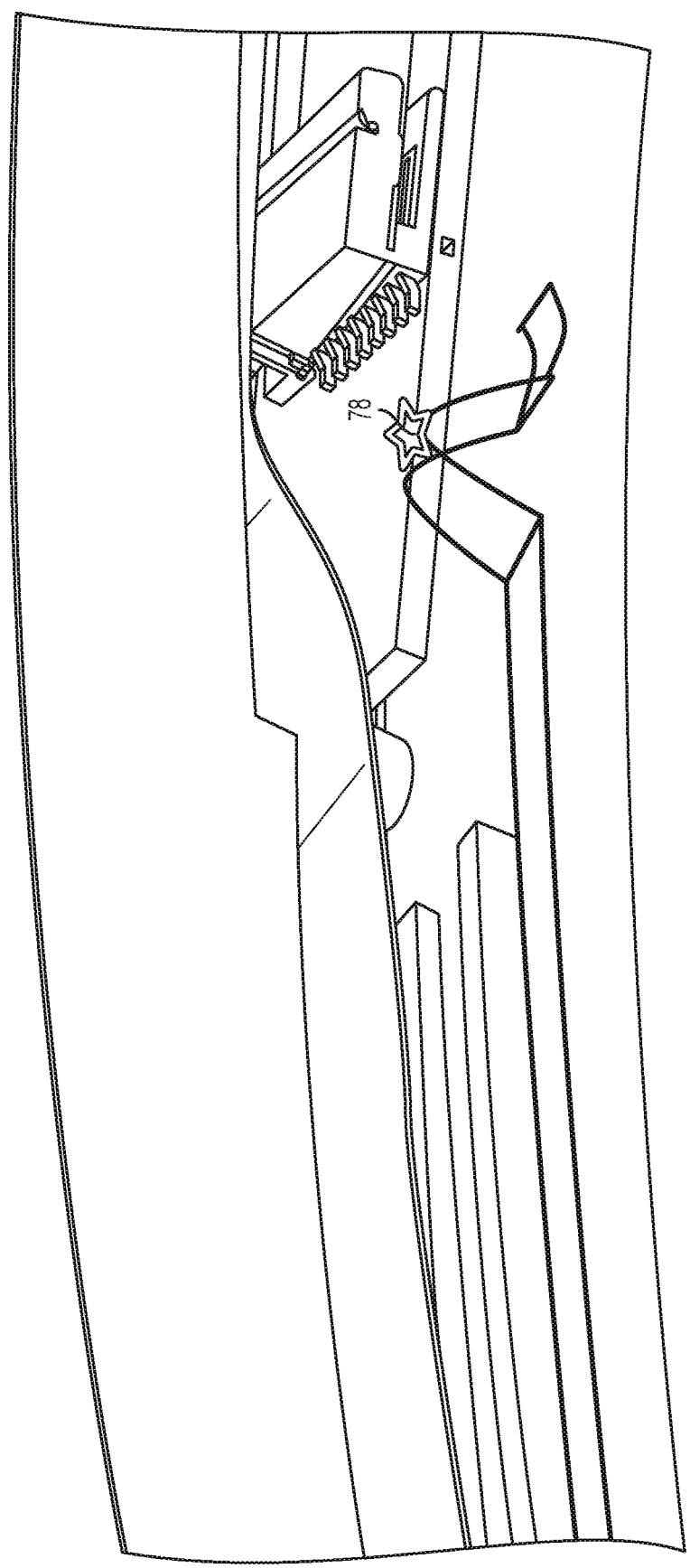
FIG. 35 is an example inner band of a wearable apparatus.

FIG. 35 shows an optional implementation of the inner band. A contact strip may fit between ribs on an inside face of the inner earpiece shell. There may be a compressive leaf spring detail 78 in the end of the contact strip. When the PCB mates up as the shells are snapped together, the bent top of the leaf spring 78 may contact a conductive pad on the underside of the Flex PCB and then the spring may compress/flex until the plastic shells are mated and closed. The compressed spring face 78 continues to mate with the Flex PCB and provide the conductive circuit between the metal slider body which is conductively linked to the end of the band and the sensor contact strip.

Figure 36:
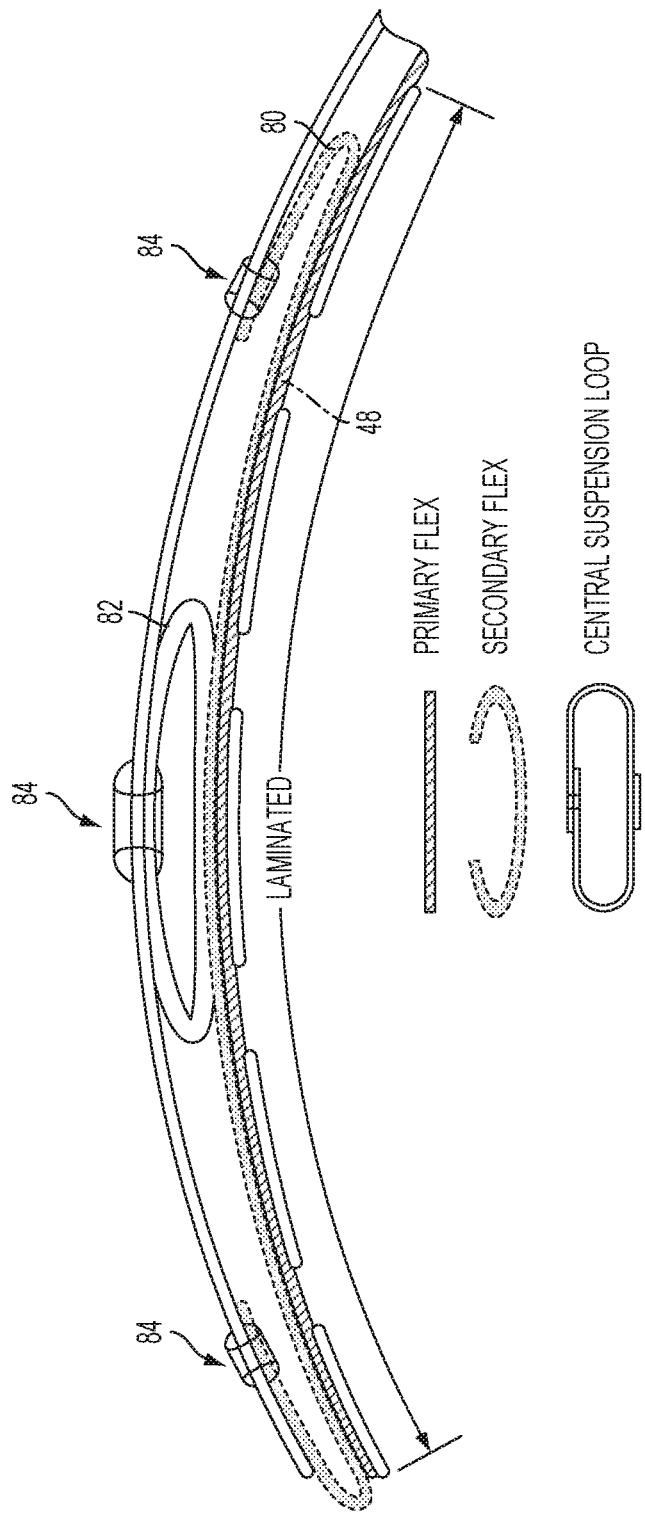
FIG. 36 is an example band assembly of a wearable apparatus.

FIG. 36 shows an embodiment which includes two inner bands: primary flex band 48 and secondary flex band 80. The secondary flex band 80 may be laminated to the primary flex band 48 and may be soldered to a central suspension loop structure 82 spacing the flex bands 48, 80 from the outer band. The central loop structure 82 may also be soldered and riveted via eyelet 84 to the outer band. The brain sensors may be disposed along the primary flex band as shown in FIG. 36.

Figure 37:
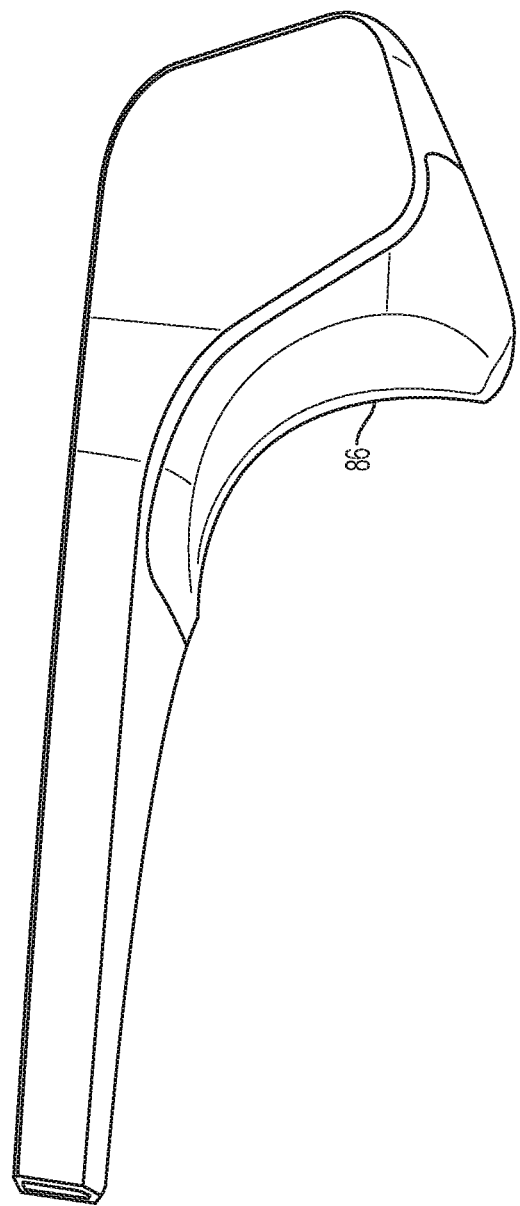
FIG. 37 is an example earpiece of a wearable apparatus.
Figure 38:
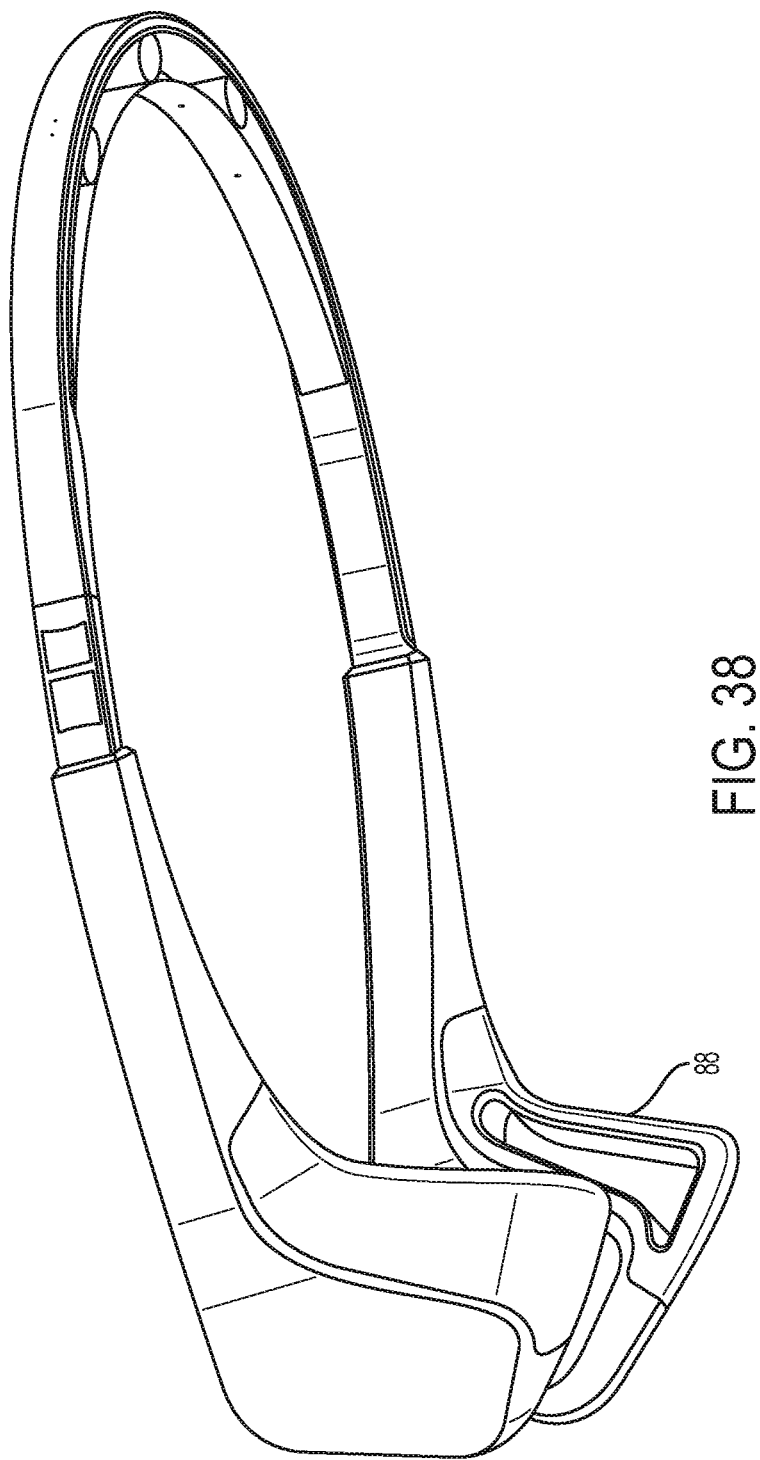
FIG. 38 is an example wearable apparatus.

In accordance with some embodiments, the ear piece has brainwave sensor(s). As shown in FIGS. 37 and 38, ear piece sensor contacts can have a number of different shapes. Further, each earpiece or ear sensor contact of the same wearable apparatus may have a different shape with respect to one another. For example, ear contacts may be filled 86 or open 88 as shown, and leading edges may tuck inside the ear. A knee of the bend may provide structural support so that the collapse primarily happens in the long strip, which can conform behind the ear. The strip may have a triangular leading edge for comfort, and the thickness of the strip may determine conformability. If the strip is too stiff, it may be painful for the user to wear. If the strip is too thin, the strip may compress to the back wall of the contact and doesn't offer the comfort that suspension of the inner band with respect to the outer band may provide.

Figure 39:
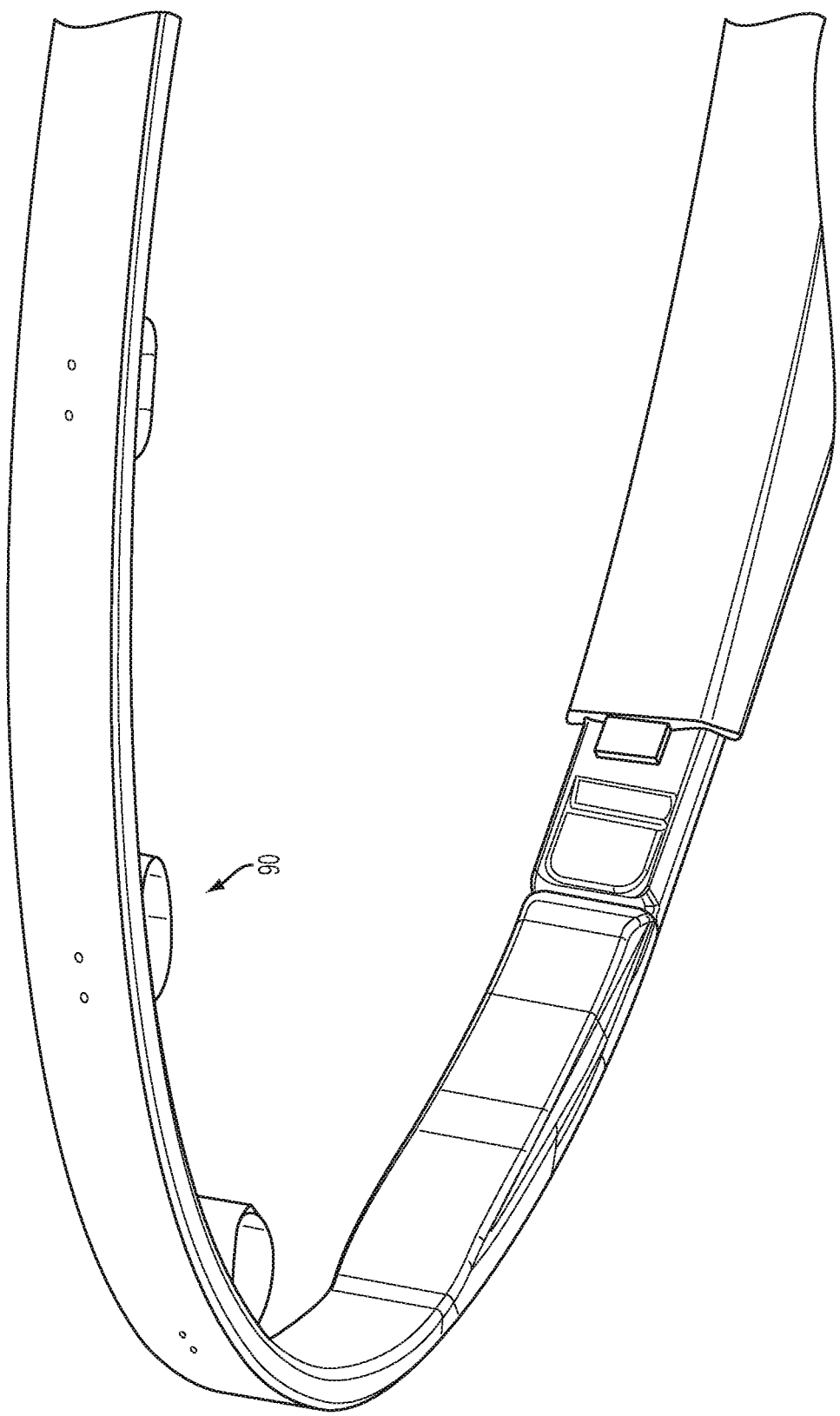
FIG. 39 is a portion of an example band assembly for a wearable apparatus.

As shown in FIG. 39, rounded conductive contacts 90 may be provided on the outer band that serves as both the brainwave sensor contacts and the biasing component or springs themselves. The rounded contacts 90 may be made of, for example, polyamide, or a plastic painted with conductive ink, or made of a conductive rubber. An example process for the silver ink is described herein.

Figure 40:
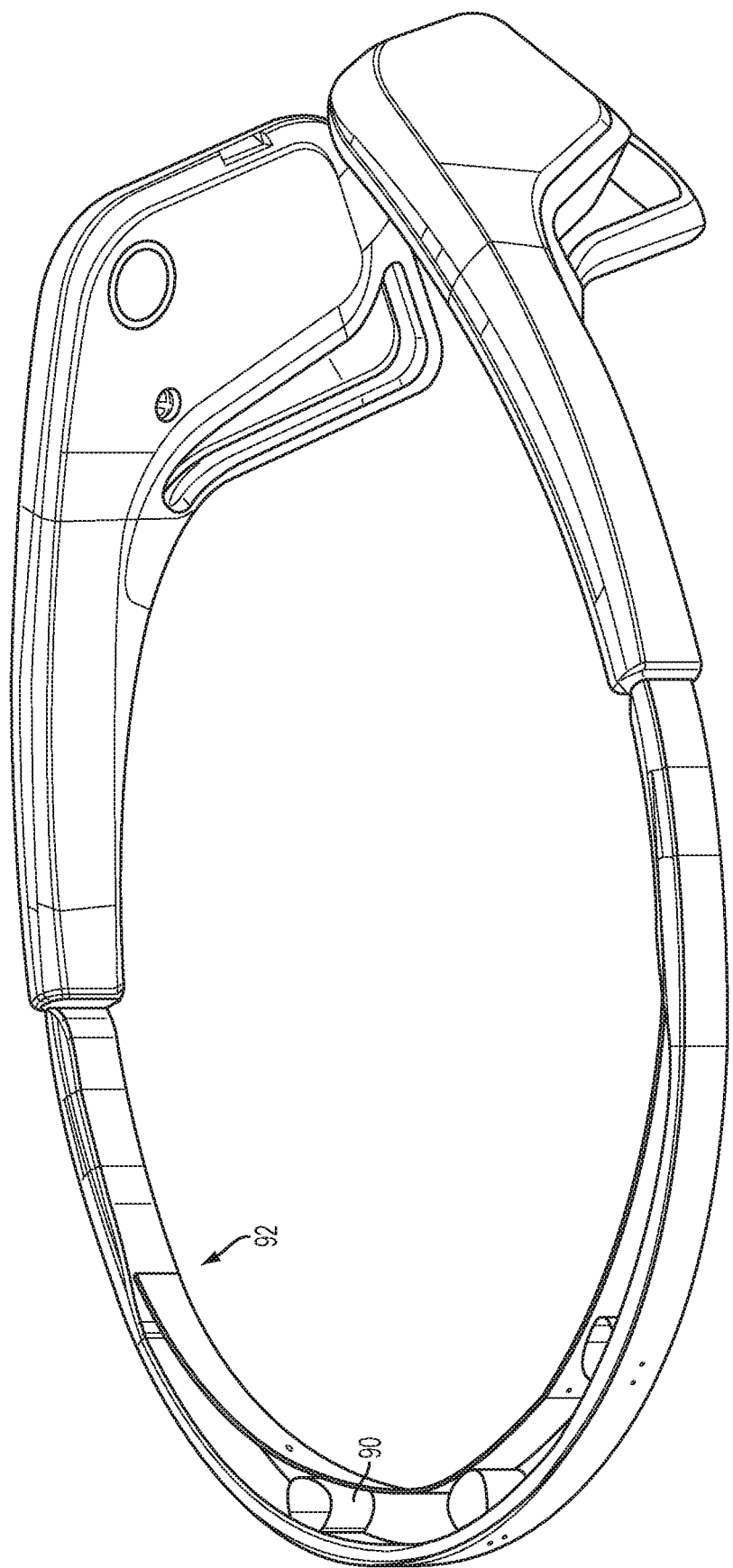
FIG. 40 is an example wearable apparatus.

FIG. 40 shows an embodiment of the wearable apparatus where the inner band doesn't slip straight into the arm structure of the earpiece but rather a portion 92 mates into the outer portion of the band assembly that is not within the arm structure of the earpiece. The biasing component may be round springs 90 made of a silicone or a similar material to the inner band (e.g. polyamide). The round springs 90 may provide additional pressure onto the brainwave sensors (e.g. electrodes) from behind, to provide a better and more consistent contact between electrode and forehead of the user. Leaf spring, round spring, helical spring, or other spring structures may be used.

Figure 41:
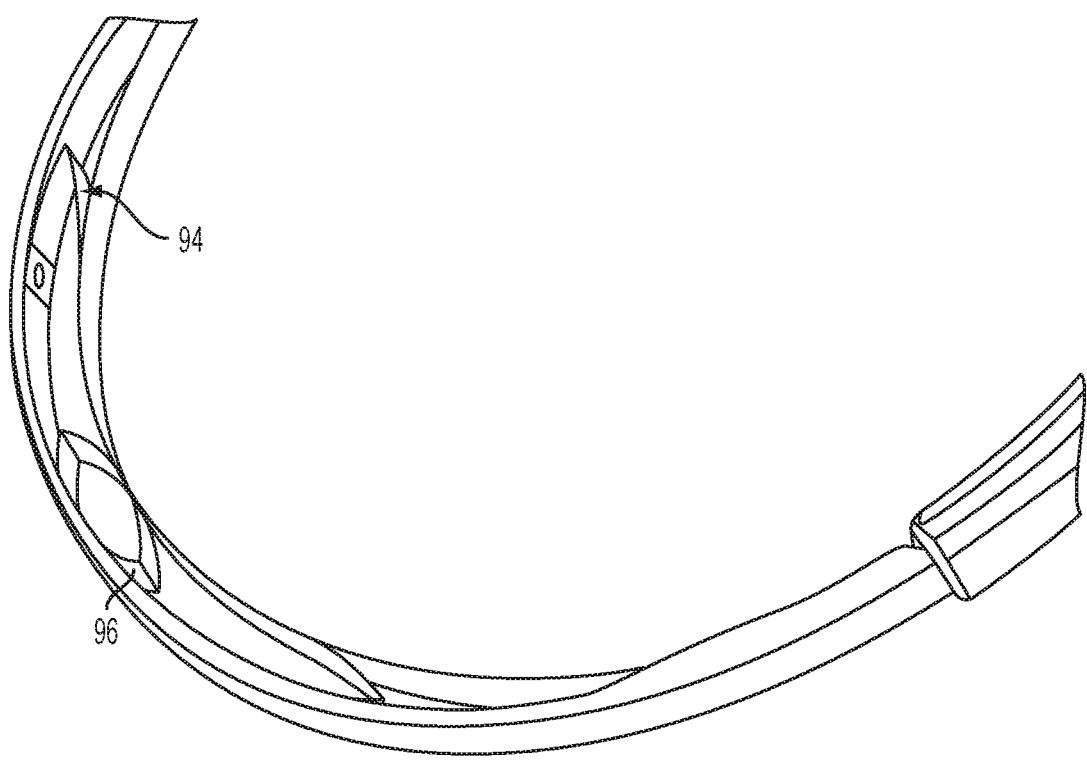
FIG. 41 is a portion of an example band assembly for a wearable apparatus.
Figure 42:
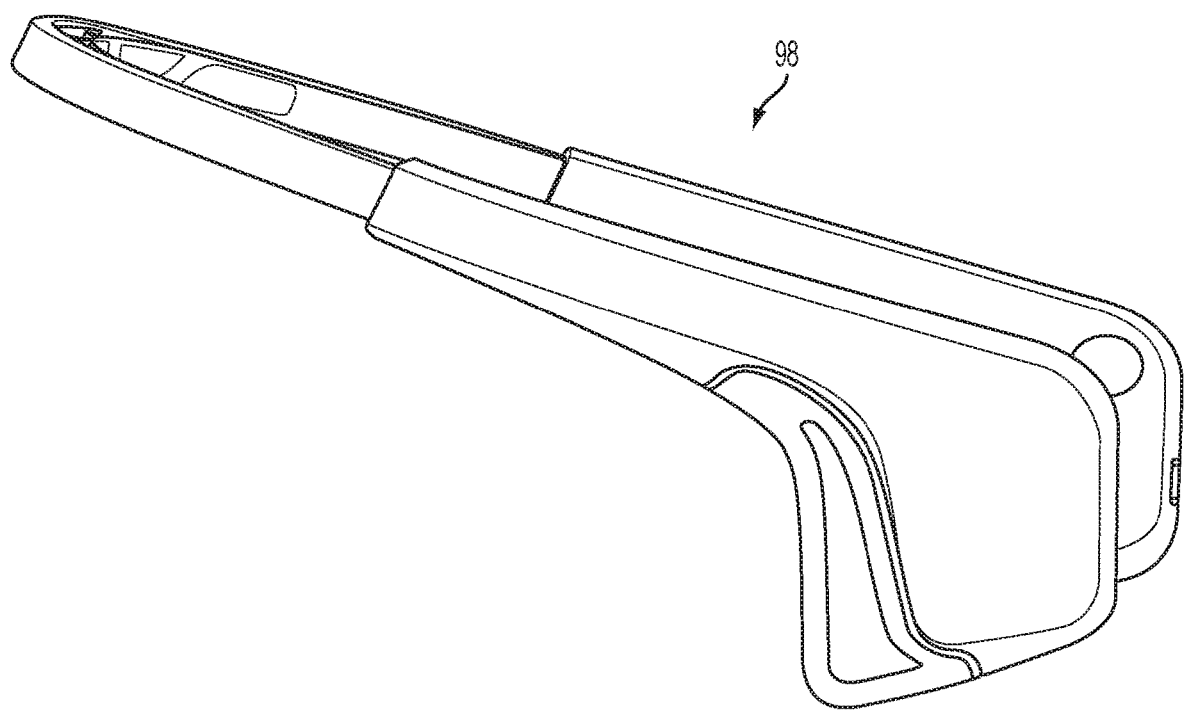
FIG. 42 is an example wearable apparatus.

In particular, leaf springs are shown in the embodiment shown in FIG. 41. The leaf springs may be on either side of a middle spring 96. The leaf springs may allow the sensor contact inner band portion 94 to push against the head. The dynamics of the middle spring 96 and the leaf springs are such that the middle spring 96 may tend to want to push the sides out, but the leaf springs pushes back and directs the contact directly into the forehead. This may compensate for a depression found on the forehead of the user, which may reside where the brain sensor electrodes are positioned.

Figure 43:
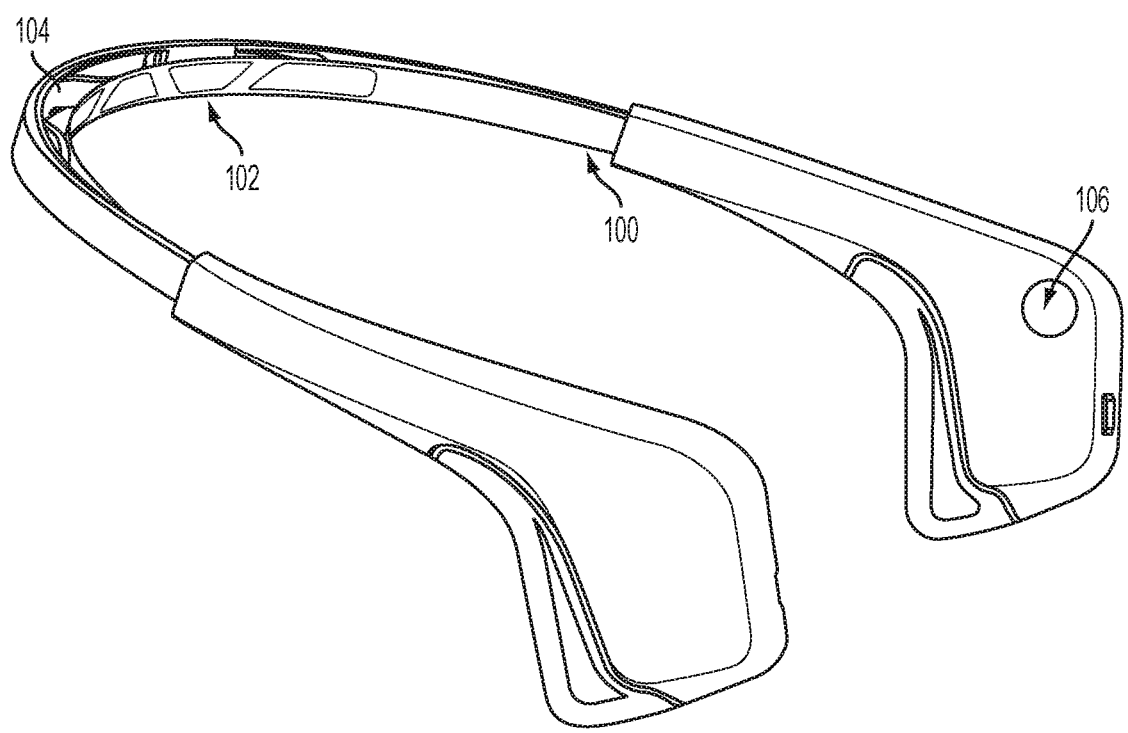
FIG. 43 is an example wearable apparatus.

FIGS. 42-48 show optional finished embodiments of the wearable apparatus 98 according to some embodiments. FIG. 43 shows that electrodes 102 are on the inner band (e.g. a flex PCB). The electrodes can connect directly to the forehead from the flex PCB. The flex colour or material could be changed by overmoulding, or otherwise covering with silicone or another material, or it could be bare. The colour of the flex can be changed by laminating additional layers on top of the flex as well. These layers could be made of polyamide. The flex assembly may benefit from additional polyamide layers both for colour as well as to determine the flexibility of the band. The band assembly at an end portion 100 may slide freely into the arm structure of the earpieces in order to conform against the user's head an attach using an adjustable attachment component. The addition of more polyamide may increase the stiffness of the inner band. As shown in FIG. 43, an on/off button 106 may also be provided in one of the earpieces. Springs 104 may provide a deformable attachment between the inner and outer bands.

Figure 44:
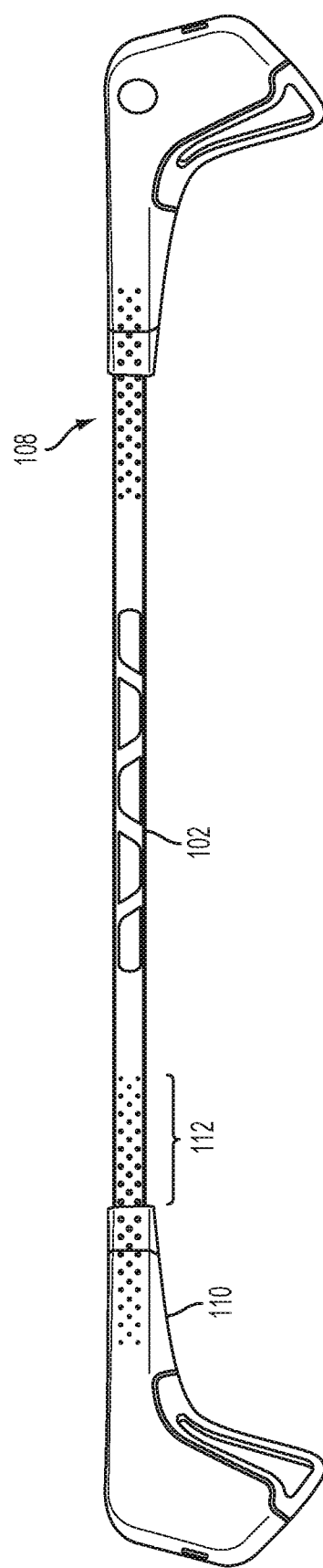
FIG. 44 is an example wearable apparatus.

As shown in FIG. 44, markings 108 on the inner band may be provided on an area of adjustment 112 of the band for sizing. The band may extend or contract into an arm 110 of the earpiece. The markings 108 indicate how extended or contracted the band is, allowing the user to know the size of the band. Markings 108 can be symmetrical, so the user can know that the band is symmetrically sized on both sides. The markings 108 may be made in a pattern that communicates the sizing to the user. There may be a gradation or a cypher that indicates the sizing in an intuitive way, optionally through numbers, dots, shapes of different graded sizes (e.g. bigger at the back, smaller at the front), or graded colour, shading, or pattern. These markings 108 can be applied in different ways. For example, they can be screen printed on using the same ink as the electrodes 102, or a different ink. The markings 108 could be stenciled. In the case of using a Flex PCB as the inner band, the markings 108 can be created by using electrical traces in the flex itself. The markings 108 could also be achieved through cut-outs in the polyamide or other layers of the flex, revealing either a different colour, or material underneath. The markings 108 may be cut-outs that reveal bare metal underneath that is then plated in a different metal.

Figure 45:
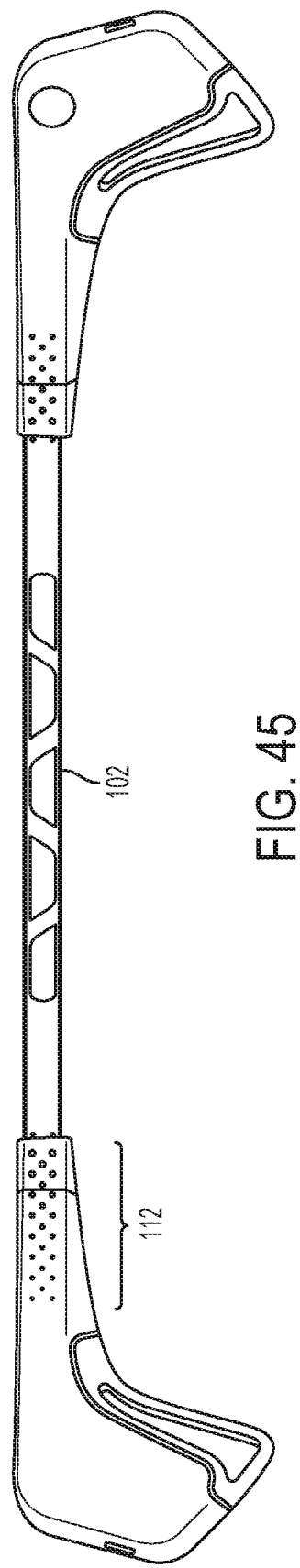
FIG. 45 is an example wearable apparatus.

FIG. 45 shows an embodiment of the wearable apparatus in a contracted position at one end of the area of adjustment. As shown, the markings are hidden.

Figure 46:
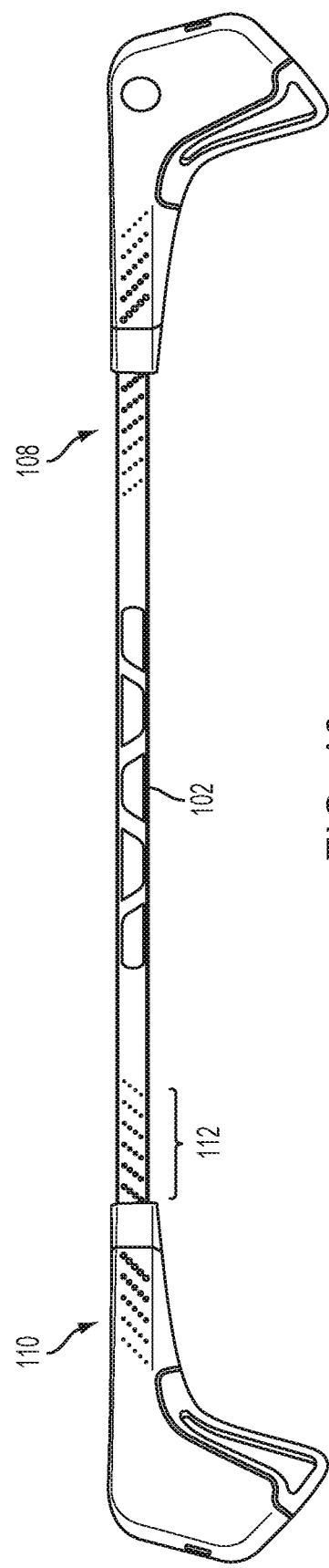
FIG. 46 is an example wearable apparatus.

FIG. 46 shows an embodiment of the wearable apparatus where embossing, printed, or debossed patterns or markings 108 makes the sizing pattern on the inner band look visually harmonious with the arm structures. The markings 108 indicate the area of adjustment 112. The electrodes 102 may also take on different shapes for aesthetic or functional reasons.

Figure 47:
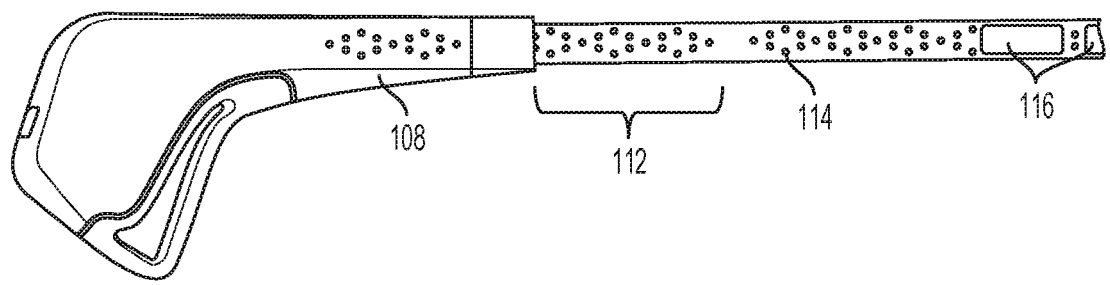
FIG. 47 is an example wearable apparatus.

FIG. 46 shows an exemplary arrangement of electrodes having a design matching the visual shape of the ear contact. The electrodes may be painted on with conductive (e.g. silver) ink. An example process is described herein using a hatched pattern of copper, FIG. 47 shows an example of the inner pattern in a different pattern and colour, with debossed pattern markings 108 and silver pattern markings 114 to indicate the area of adjustment. The silver pattern markings 114 may be proximate the brow contacts. Various embodiments of the electrodes are possible. For example, the electrodes may include: painted-on electrodes; squishy electrodes; silver electrodes embedded in conformal (rubbery) material, optionally in an S-shape so the metal can conform as well; hydrogel wrapped in an osmotically permeable membrane, like a dialysis tubing made into long thin tubes that can slip through hair; and stick-on electrodes.

The wearable apparatus of embodiments described herein may be configured to perform electrode self-test and gain compensation. By injecting a deliberate (low level) perturbation signal generated by the MCU at the input to the DRL integrator, a test signal (ETEST) may be output from the DRL output to the user's forehead. This signal can be a squarewave of any software programmable frequency, or a step function, Optionally, a spectrally pure sinewave may be used. This signal does not need to be present at all times (but could). If the DRL and REF electrodes are working properly, the test signal may appear at the REFBUF signal line and can be sampled by the controller at REFAD. This can allow the determination of whether the DRL and REF electrodes are making good contact. If these electrodes are not making good contact, any attempt to sample EEG signals is pointless, and the user interface can react in a user friendly manner, such as blanking outputs, or even communicating to the user that they need to make adjustments.

The REFBUF signal is the Analog reference to all electrode amplifiers. When ETEST is active and the REFBUF and DRL electrodes are making good contact, the test signal will appear on REFBUF. Properly connected sense electrodes will also pick up the ETEST signal applied to the user by DRL, In such case, the test waveform in the electrode signal and REFBUF signal will experience cancellation. If an electrode is not properly connected, it will experience less and less cancellation, the weaker its connection. The amount of ETEST waveform at the output of the electrode amplifiers, sensed by the A/D converters of the MCU, will give an indication of the quality of electrode coupling to the user. A fully disconnected electrode will have the maximum output signal amplitude, and a perfectly connected electrode will have zero. This knowledge can be used to indicate to the user that they should adjust their electrodes, can be used by the firmware or application to disregard the signal from a disconnected electrode, and/or could allow the algorithms to adjust their operation for optimum performance under the particular conditions being experienced. The amplitude of the test signal in at the electrode amplifier outputs indicate the effective gain of each electrode. This information can be used by software to adjust each individual electrode channel's gain to optimize differential or averaged measurements.

Figure 48:
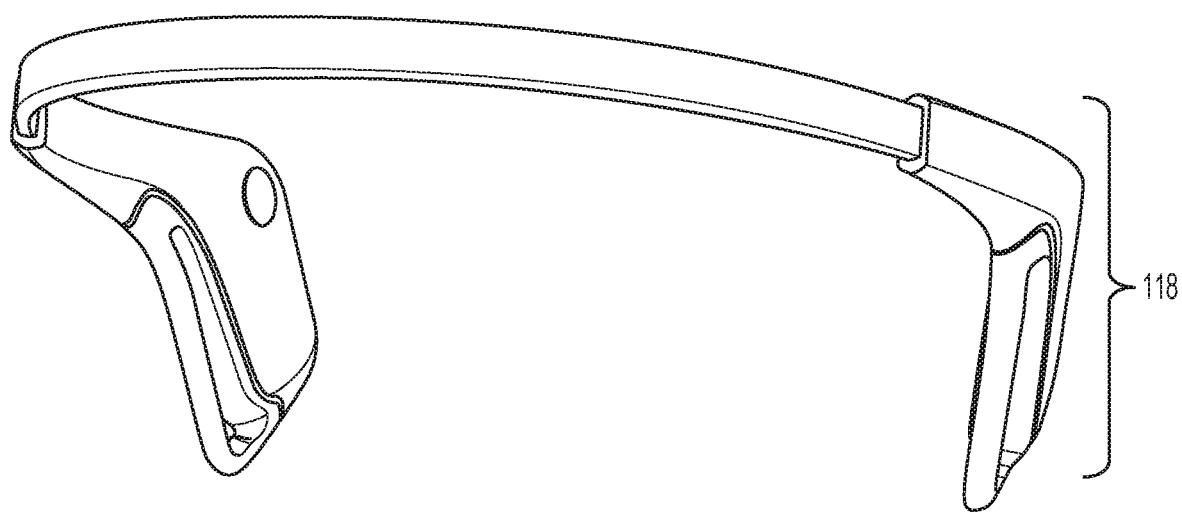
FIG. 48 is an example wearable apparatus.

FIG. 48 shows an embodiment of the wearable apparatus according to some embodiments with removable ear piece sensor contacts. The ear piece sensor contacts may snap into the plastic earpieces 118 (e.g. ear pods). There may be provided a thin metal area with a post that goes into the conductive rubber. The metal may not be required for function, and may be purely aesthetic. The metal may be thicker, or thinner, or shaped differently. The metal may be metal-plated plastic, plated with a conductive material.

There may be a post or screw that provides electrical conductivity from the conductive rubber contact through the metal contact, to the appropriate component on the PCB board in the earpiece.

The wearable apparatus may further comprise one or more lights. Lights may be provided on the top, back, front, side, or other parts of the wearable apparatus. For example, an arrangement of 5 LED lights may be provided. The computer processor control the lights to display patterns and colours indicating charging, Bluetooth paring, low battery, Bluetooth paired, and other states. In addition to lights, or as an alternative, a display screen may be provided on the wearable apparatus. The display may be a LCD, OLED, E-Paper, or other display type and may be positioned on one or both of the arm structures or earpieces. Alternatively, a display or light may be positioned in the wearable apparatus to be viewable by the user while wearing the wearable apparatus, optionally at a periphery of the user's field of view. The display may indicate information including the relative state of the wearer. For example, if the wearer is relaxed (high alpha, for example), the display could show coloured light associated with relaxation, a lighting sequence that moves "down" once or in repetition, or other indicator. The display could also indicate when something is salient, such a by detecting a P300 ERP from the user. The display may be on the front so other users can see the state, or on the back, side or inside to be discreet.

The wearable apparatus could be made small and thin by having a battery and transmitter that is off of the device, connected for example by a wire. This battery and transmitter could be clipped onto clothing, held in a pocket, or the weight of it could help to create pressure and counterbalance the headset.

The wearable apparatus may include integrated brainwave sensors for collecting bio-signal data include, for example, electroencephalogram sensors, galvanometer sensors, or electrocardiograph sensors. One or more other sensors may also be internally or externally integrated in the wearable apparatus, including: heart rate sensors; blood pressure sensors; GPS hardware; barometric pressure sensors; accelerometers; ambient light sensors; microphones; and other sensors.

Figure 49:
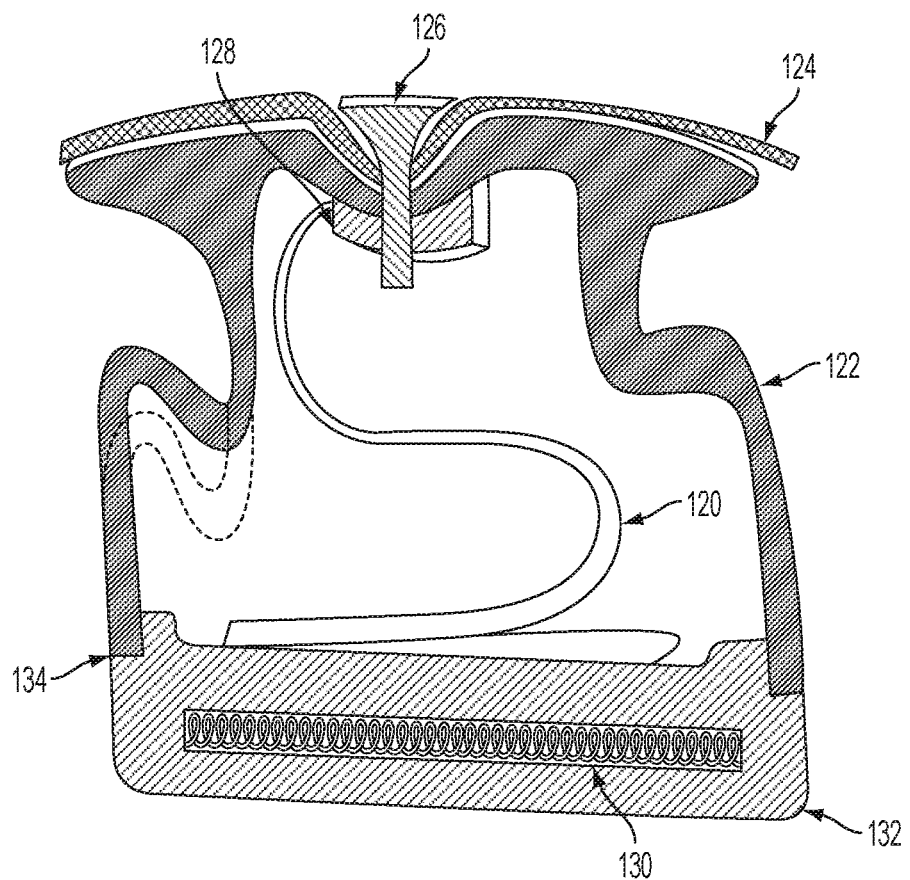
FIG. 49 is an example sensor of a wearable apparatus.

As shown in FIG. 3, the wearable apparatus may have a key pad style sensor design. Further details are shown in FIG. 49. The sensors may comprise conductive ink printed on elastomer. Elastomer forms a compressible structure that rebounds with a force suitable for the electrode or sensor contact area of the wearable apparatus. The conductive electrode or sensor area connects to a flexible circuit 120 via a conductive rivet 126 (or press fit barb with conductive retainer). The conductive rivet 126 may be a plated plastic press fit barb supported by a metal or plastic container 128. The flexible circuit 120 may be printed or etched. Elastomer may be of silicone or soft thermoplastic polyurethane (TPU) rubber 122.

An example of a suitable conductive coating is DUPONT PE872 with a silver composition for biosignal measurement on skin, shown as stretchable silver ink coating 124. Many electrodes or sensors may be mounted on a rigid or springy support, such as spring steel 130. An example construction of a support is TPU rubber overmold 132 welded on a spring steel 130 core by a welded attachment 134.

In another aspect, the wearable apparatus may be a stretch headband.

Stretch material can be used to construct a headband that fits different head sizes. The stretch allows it to be form fitting for the user. For the sensors, conductive polymers may be used to print on electrodes and coat plastic fibers that are woven into a stretch fabric or thread. The stretch fabric may be used for the inner and outer bands. In some embodiments, the headband may be washed with circuits that are waterproof or removable.

Figure 50:
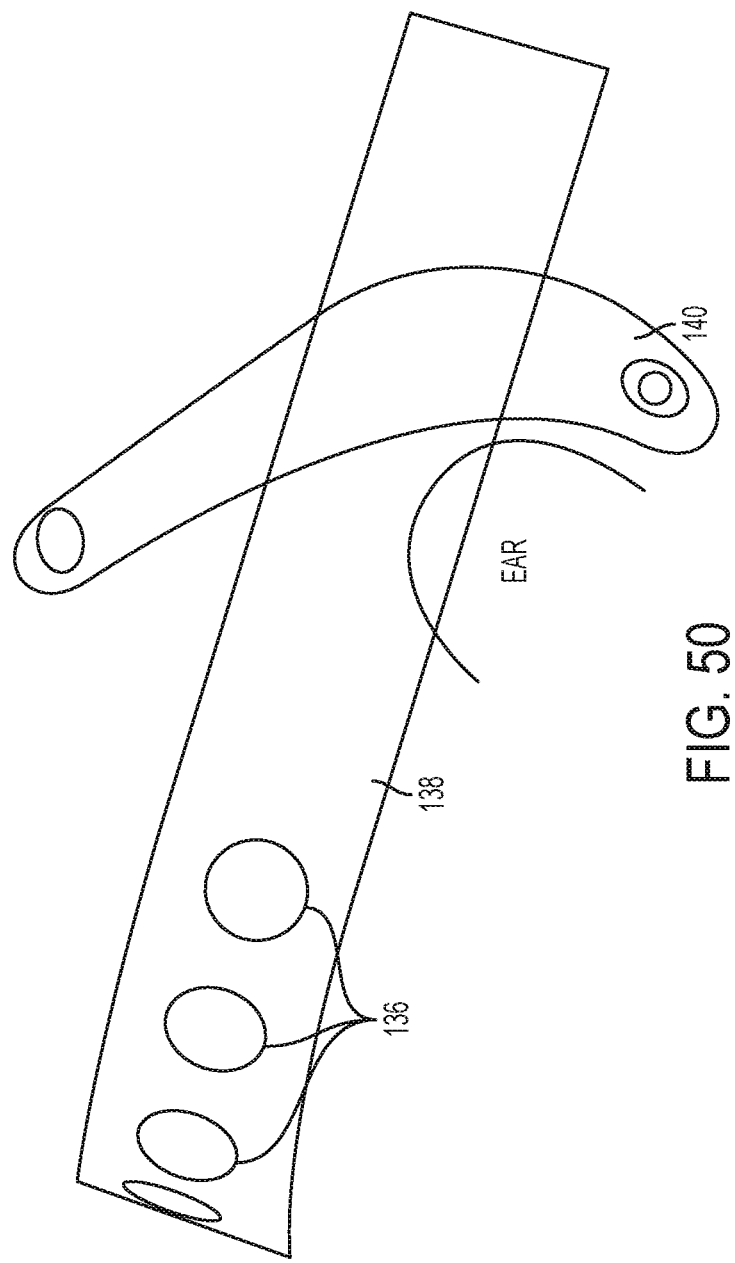
FIG. 50 is an example wearable apparatus.

FIG. 50 shows an example of the headband 138 made with a stretchy fabric. The headband 138 includes electrodes 136 for sensors.

Areas on the head that cannot be reached using the tensile headband 138 may be accessed using semi-rigid attachable parts that can be affixed to the headband 138 in different locations. An example earpiece 140 is shown as a mastoid arm attachable parts. Lever type designs take advantage of tensile forces in the stretch fabric to apply contact forces to the electrodes at the end of the lever arms used for the earpiece 140.

Figure 51:
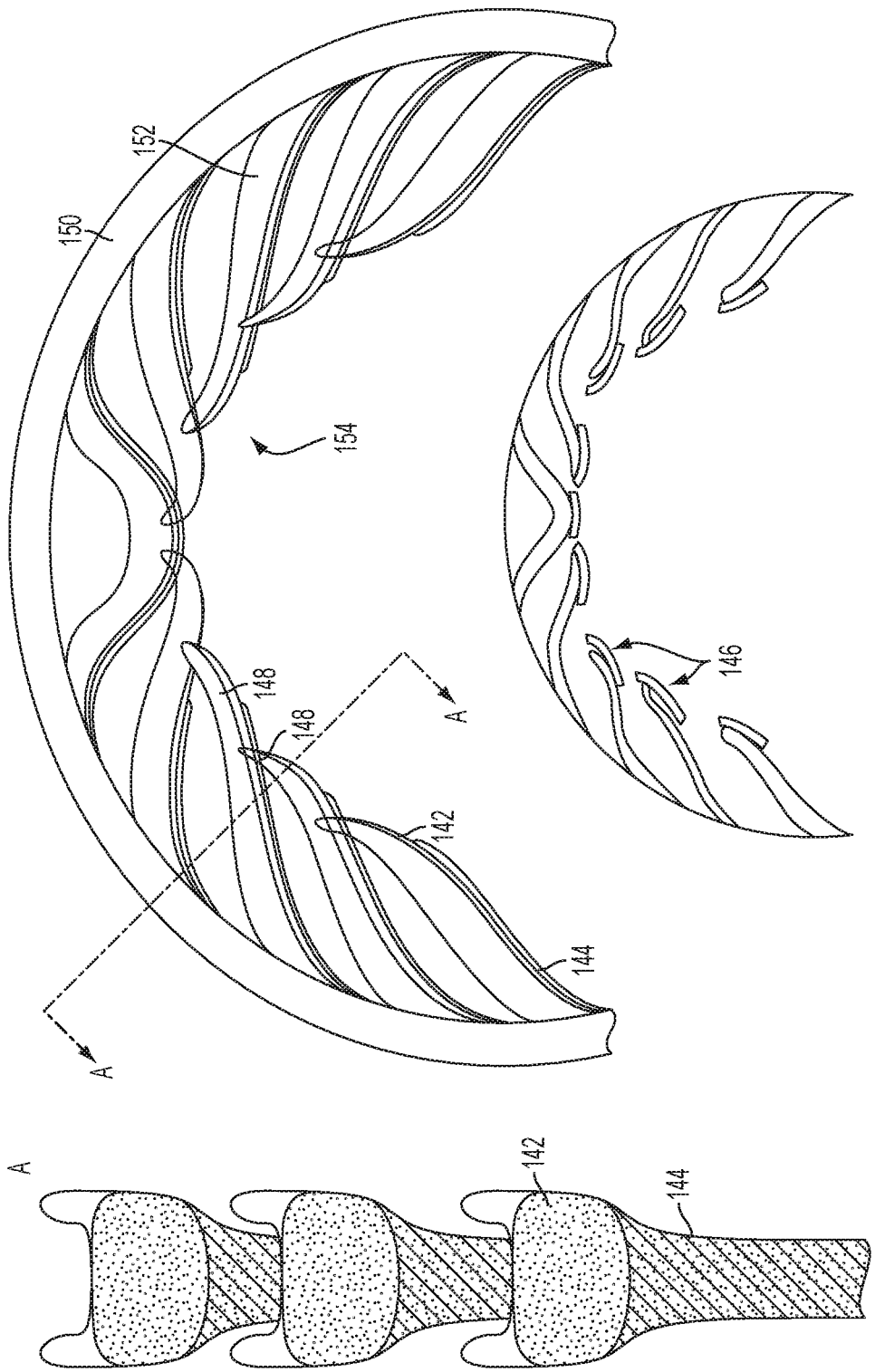
FIG. 51 is an example sensor for a wearable apparatus.

FIG. 51 shows an example illustration of layered electrode petals 154 used for at least a portion of the sensor contact area of a stretch headband. The headband has a spine 150 with a thermoplastic overmold on a stiff core. The petals 154 may be constructed using a soft TPU comolded on harder TPU to control stiffness while achieving a soft electrode. The petals 154 include a conductive coating 142 and a flexible dielectric coating 144.

Rubber and plastic or rubber composites form a plurality of electrode support arms 152 as petals 154 that deform to conform to the shape of a user's head (or other body part), to provide consistent and reliable contact force for the sensor contact area. A group 148 of electrode support arms or petals 154 may be nested or layered. In this example embodiments, the petals 154 are linked to increase lateral stiffness to maintain form and thus aesthetics and comfort.

A group 146 of petals 154 may be separated to allow them greater travel and to reach through hair or other debris, for example.

Petals 154 can be injection molded using TPU rubber. Stiffness and compression attributes may be tuned by adjusting wall thickness and form of the petals 154. Rubber may be co-molded with a stiffer thermoplastic which reduces part volume when greater stiffness is required or specific attributes such as lateral stiffness is required.

Figure 52:
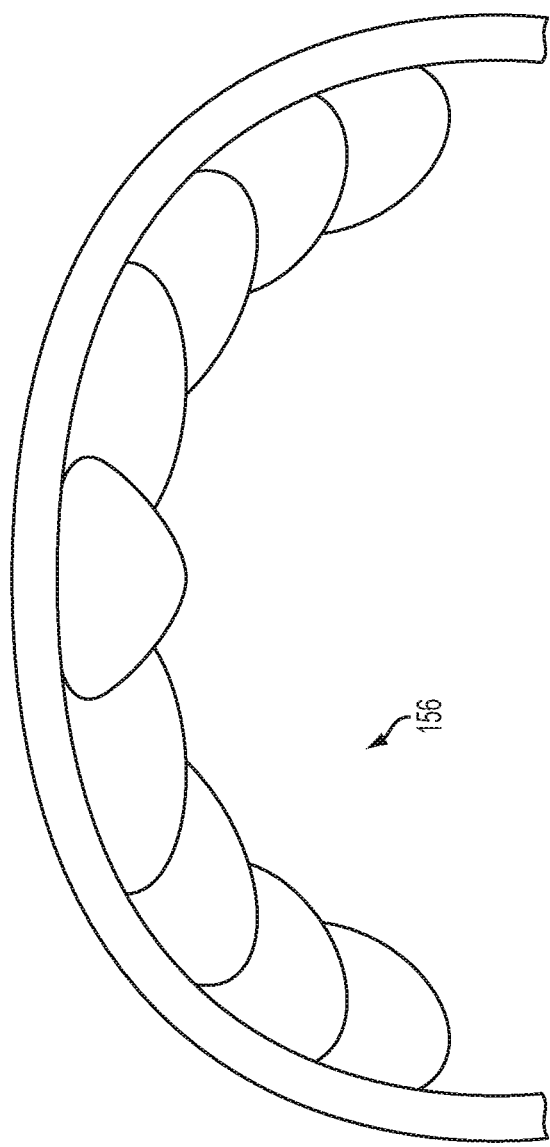
FIG. 52 is an example sensor for a wearable apparatus.

FIG. 52 illustrates different shapes for the layered electrodes 156 used for the brainwave sensors.

Various shapes of petals may be used depending on different materials, coatings, and connection methods and aesthetics. The shaped electrodes 156 may be used when conductive coating is applied to only one side of petal object and the bend radius must not be too small.

Figure 53:
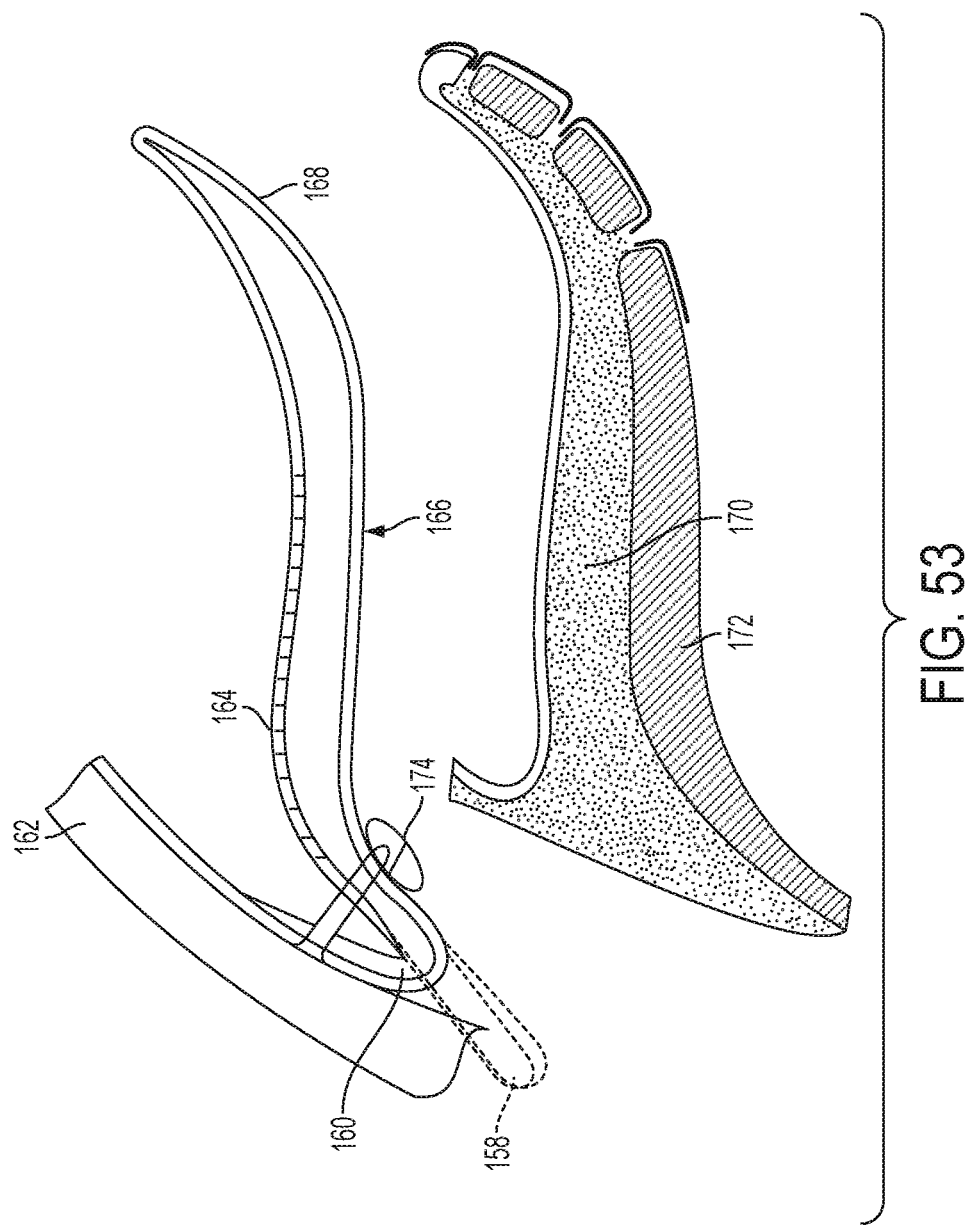
FIG. 53 is an example sensor for a wearable apparatus.

FIG. 53 shows detailed illustration of a further example electrode petal 158 according to some embodiments. The petal 158 is secured to the spine 162 of the headband using a mounting feature 174. The petal 158 includes a conductive layer 168 and a dielectric coating 166. The petal 158 may be comolded with stiffener 164 in some example embodiments.

Conductivity can be achieved using a conductive matrix in the elastomer, such as loading with carbon black. The surface properties of the electrodes may be tuned with texture and the application of conductive coating 168, such as silver or silver and silver-chloride loaded polymer inks. Selection of specific contact regions may be achieved using a dielectric coating 166 to shield the conductive areas. Conduction to the electronic system (e.g. computer electronics 26) that contains amplification, filtering, sampling, and so on, is achieved via conductive adhesives or mechanical fixation. Mechanical fixation (e.g. via mounting feature 174) may compress a conductive region of an electrode petal 158 to a conductive region on a printed circuit, for example.

Copper circuits may be gold plated to inhibit oxides from forming. Screen printed electronics may use silver ink for the contact area, or silver ink with a thin carbon layer to stop oxidation.

On the petal 158, if the rubber substrate is not conductive, the conductive ink (or conductive co-molded coating) is extended such that the surface may form the conductive link to the electrical system. Printing of inks is facilitated by molding the rubber such that it may be unfolded and held flat for printing, then released for assembly, as shown with folds 160 used to bring conductive surfaces to opposing sides. A mounting feature 174 secures the petal 158 to the spine 162 of the headband to maintain the fold 160. Accordingly, the petal 158 may be molded flat to facilitate screen printing of conductive ink, and folded during assembly.

In some example embodiments, insulating elastomers can be molded hollow with small holes to allow passage of moisture. The interior of the petal 158 can be filled with a hydrogel 170 that is contained by the petal skin. The exterior of the petal 158 may be a soft TPU layer 172. The hydrogel 170 is hydrated with a saline solution. The electrode area that touches the skin has a conductive coating such as silver ink. Ions in the saline solution form the electrical connection from the surface of the petal and the electrical system. Flexion of the petals cause a pumping action that forces moisture to the surface of the electrode when the device is being worn.

Figure 54:
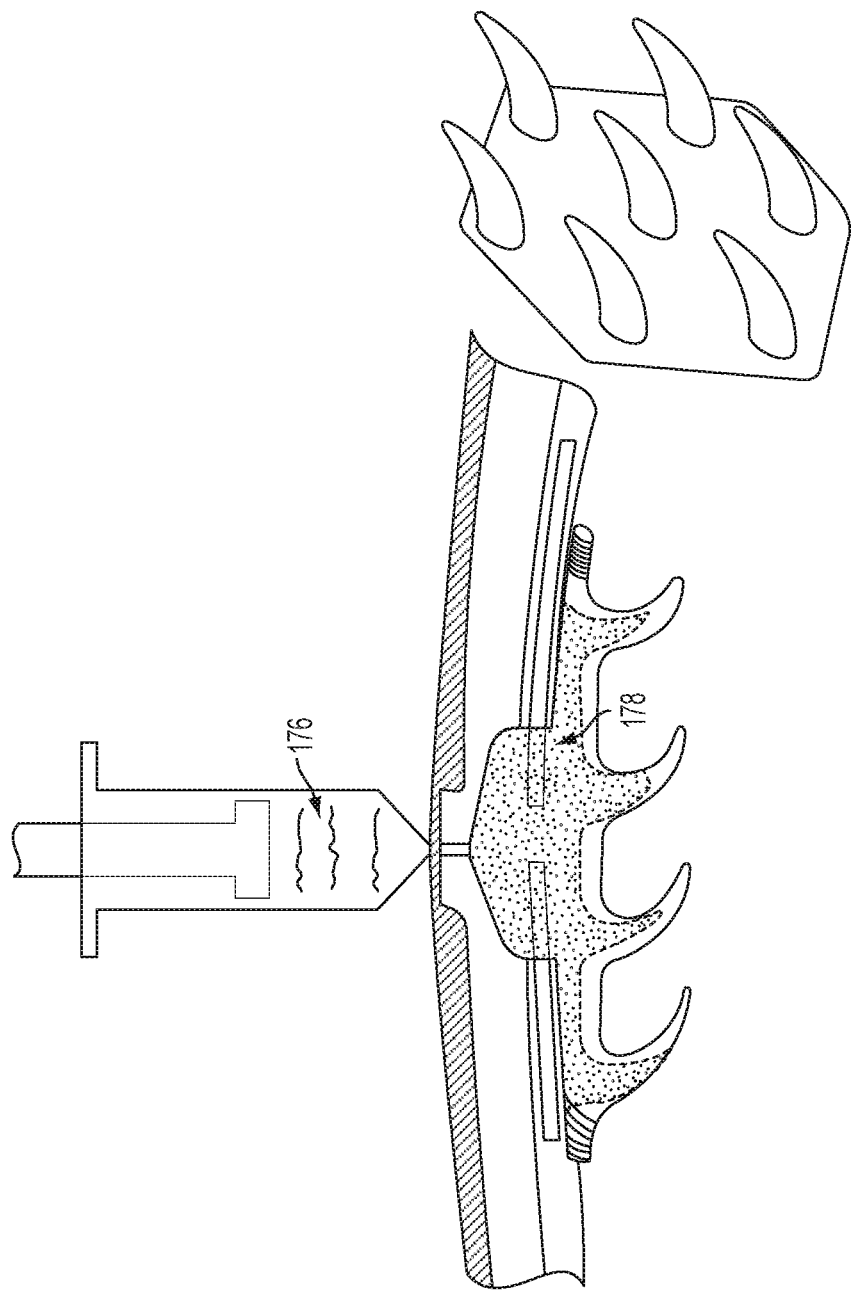
FIG. 54 is an example sensor for a wearable apparatus.
Figure 55:
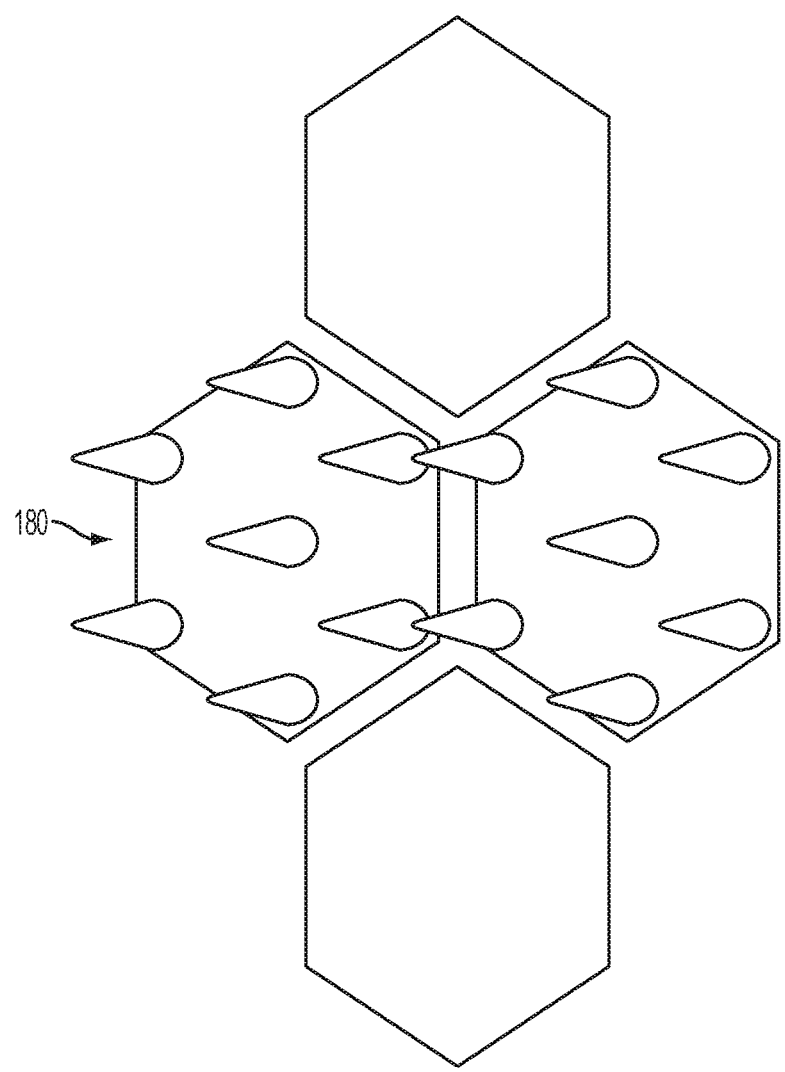
FIG. 55 is an example sensor for a wearable apparatus.
Figure 56:
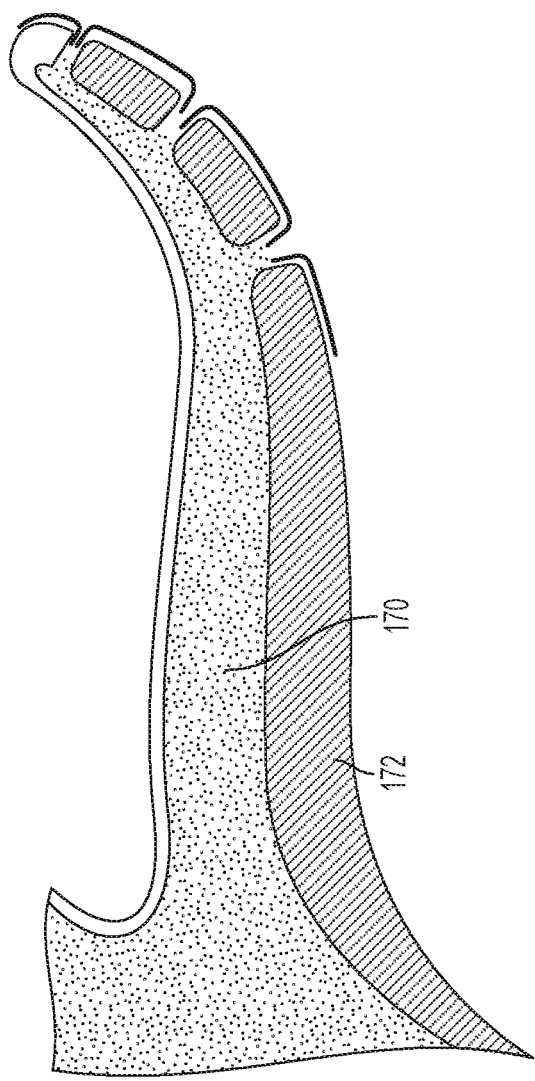
FIG. 56 is an example sensor for a wearable apparatus.

If the hydrogel becomes too de-hydrated, saline may be injected through self-sealing rubber ports. FIG. 54 illustrates saline 176 hydrating the hydrogel particles 178 in the rubber ports. FIG. 55 illustrates another example configuration of rubber ports 180. FIG. 56 illustrates a detailed view of petals with a soft TPU exterior layer 172 to provide rubber ports filled with hydrogel 170 In some embodiments, rubber petals may be arranged with groups to reduce cost and complexity. Groups may be sealed over a flexible printed circuit that comes in contact with the saline hydrogel. Gold plating or carbon printing may be used to prevent corrosion.

Figure 57:
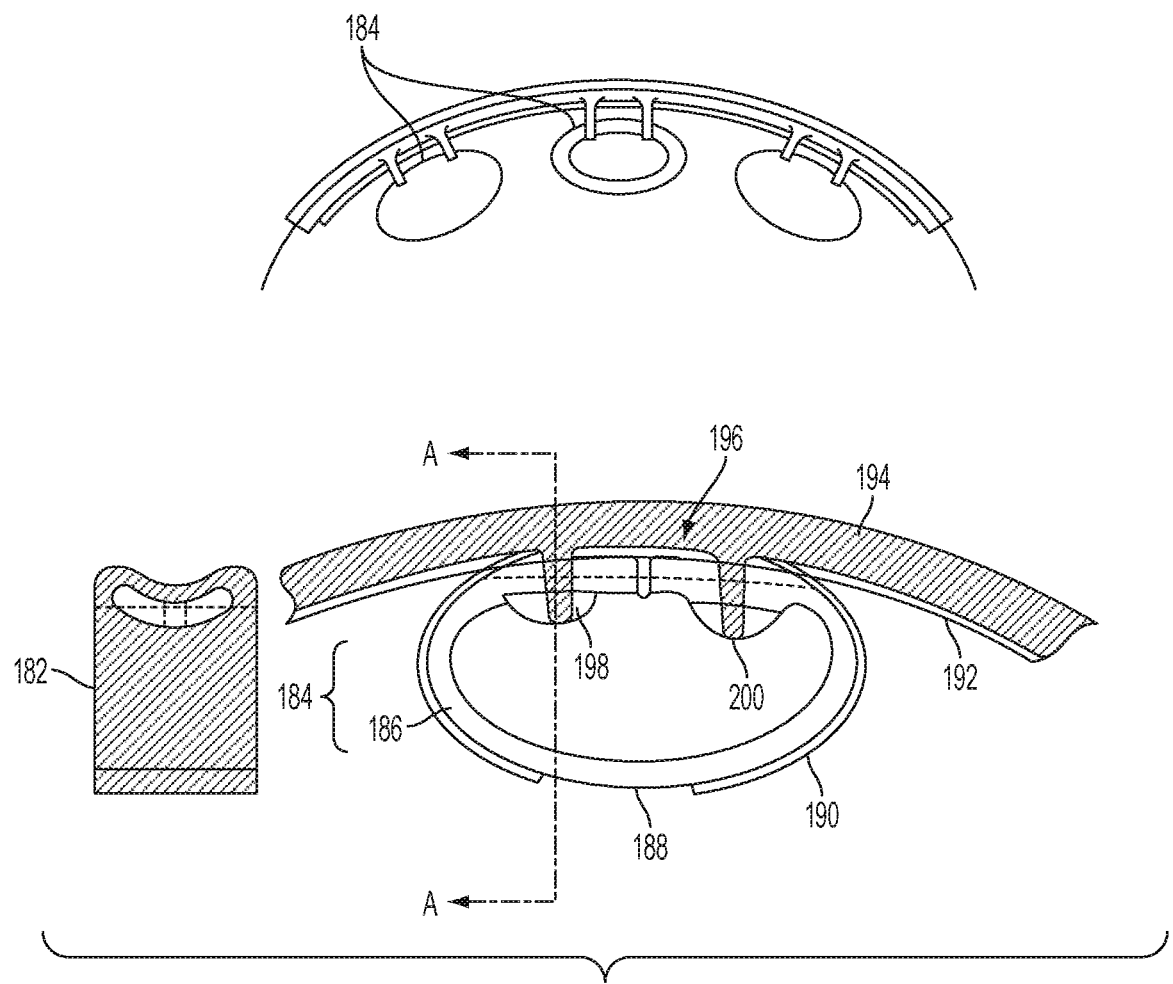
FIG. 57 is an example sensor for a wearable apparatus.

In some embodiments, the sensors may be open pillow electrodes. As shown in FIG. 57, open pillow electrodes 184 may be positioned along the headband or band assembly. The open pillow electrode 184 connects to flex circuit 192 mounted to a portion 194 of the band assembly made of hard rubber over molded on a stiffener. An electrical connection 196 may be established via compression. The open pillow electrode 184 has an inner layer 186, a conductive layer 188 and insulating layer 190. The open pillow electrode 184 may be made of thermoplastic rubber. A cross section view 182 of the open pillow electrode 184 is shown as a cut away portion at the line A. An arm 198 made of comolded rigid plastic may be attached to the open pillow electrode 184 via a weld or bond 200.

Figure 58:
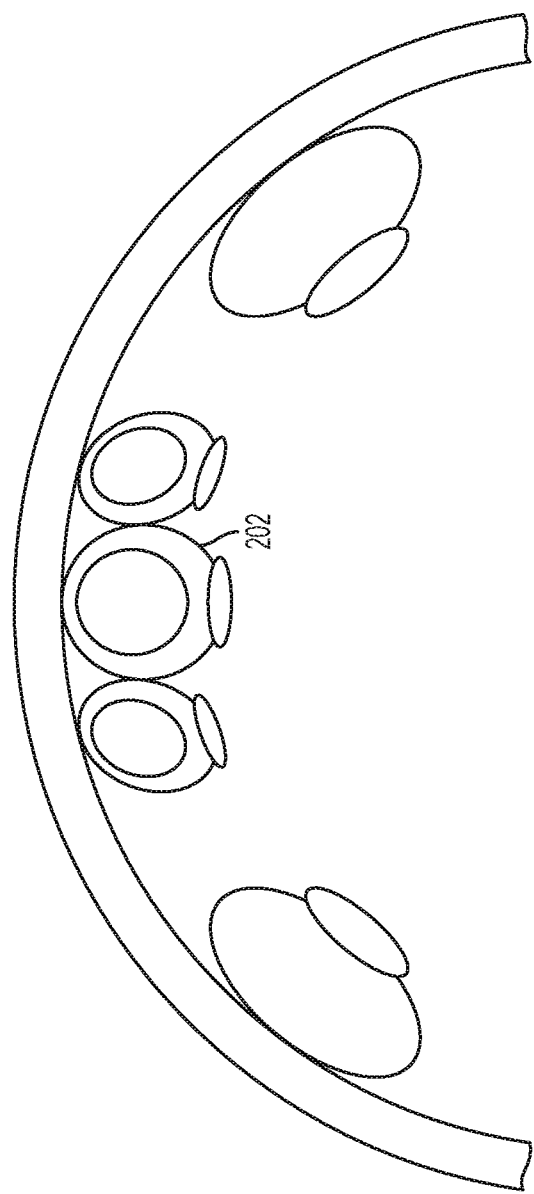
FIG. 58 is an example sensor for a wearable apparatus.

FIG. 58 illustrates an alternative view of electrodes 202 arranged in a grouping on the band assembly. The electrodes 202 may be open pillow electrodes as shown in FIG. 57 with an additional two electrodes for a total of five sensors as another illustrative example.

Figure 59:
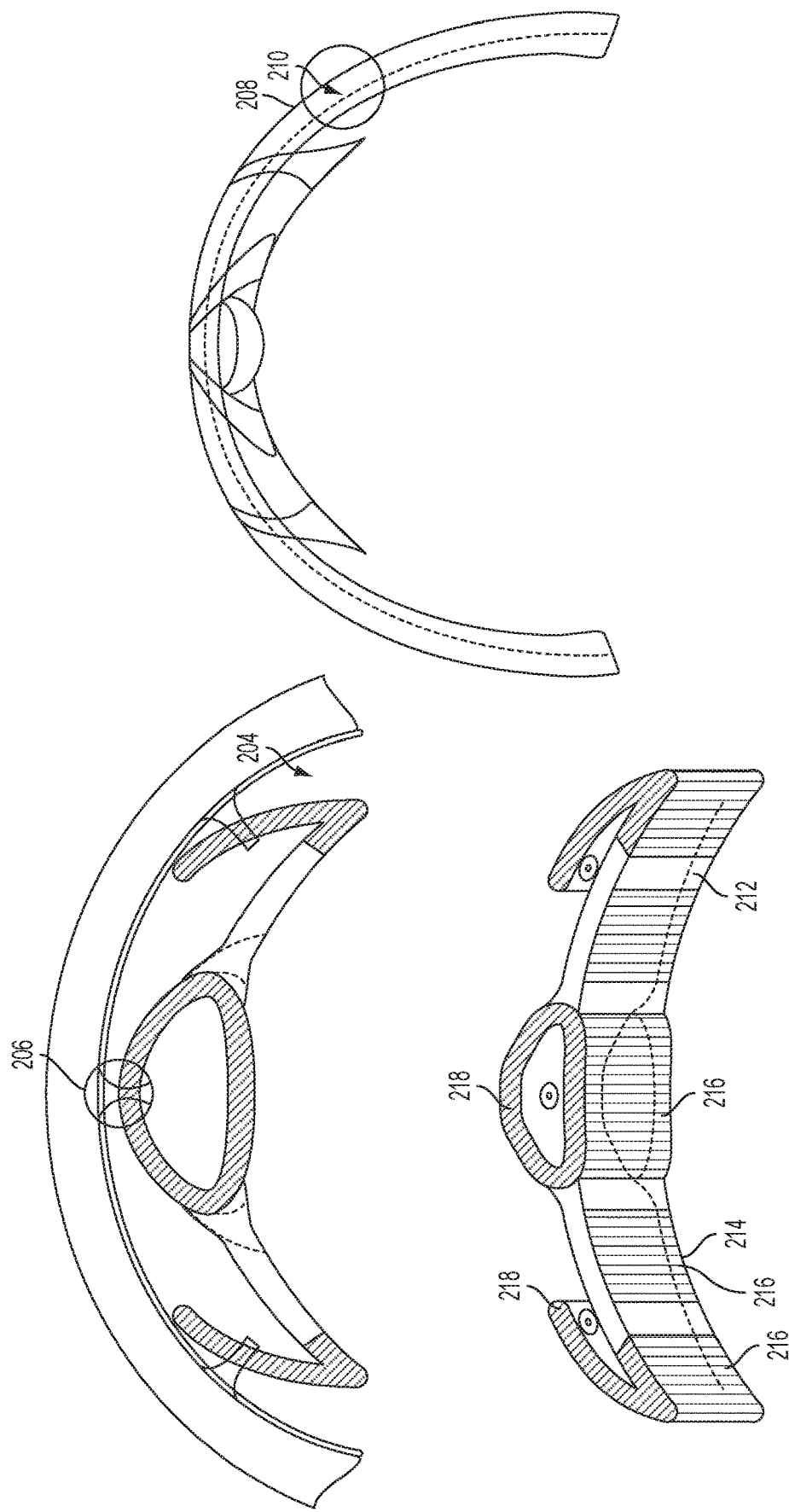
FIG. 59 is an example sensor for a wearable apparatus.

FIG. 59 illustrates a further alternative embodiment of the band assembly. The band assembly may include a rubber overmold 208 and spring steel 210 for flexibility and fit. The band assembly includes a flexible printed circuited (FPC) 204 with an electrical connection 206 to electrodes via compression. The electrodes may include a molder rubber portion 212, such as TPU BASF ELASTOLLAN and a conductive coating 216 of silver ink such as DUPONT PE872, where the coating wraps to the back portion 218 of the electrode. The electrodes may also include a connection 214 on the bottom portion.

Figure 60:
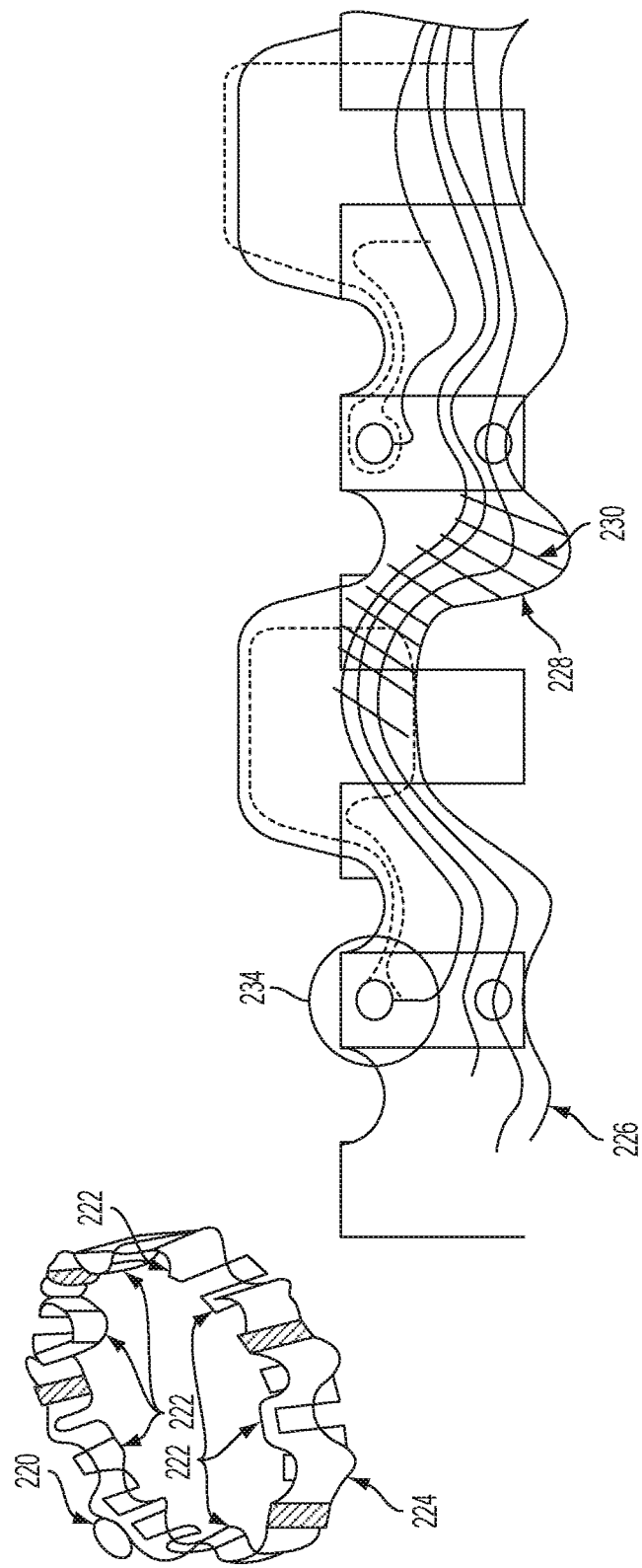
FIG. 60 is an example wearable apparatus.

FIG. 60 illustrates another alternative embodiment of a band assembly providing a stretch headband for biosignal acquisition. An electronics system 220 connects to conductive electrodes 222 positioned on a headband with a spring steel spine 224. The electrodes 222 connect to an FPC 228 via an electrical connection 234 with mechanical fixation points. The headband includes a flexible polymer portion 226 and has a dielectric coating 230.

Figure 61:
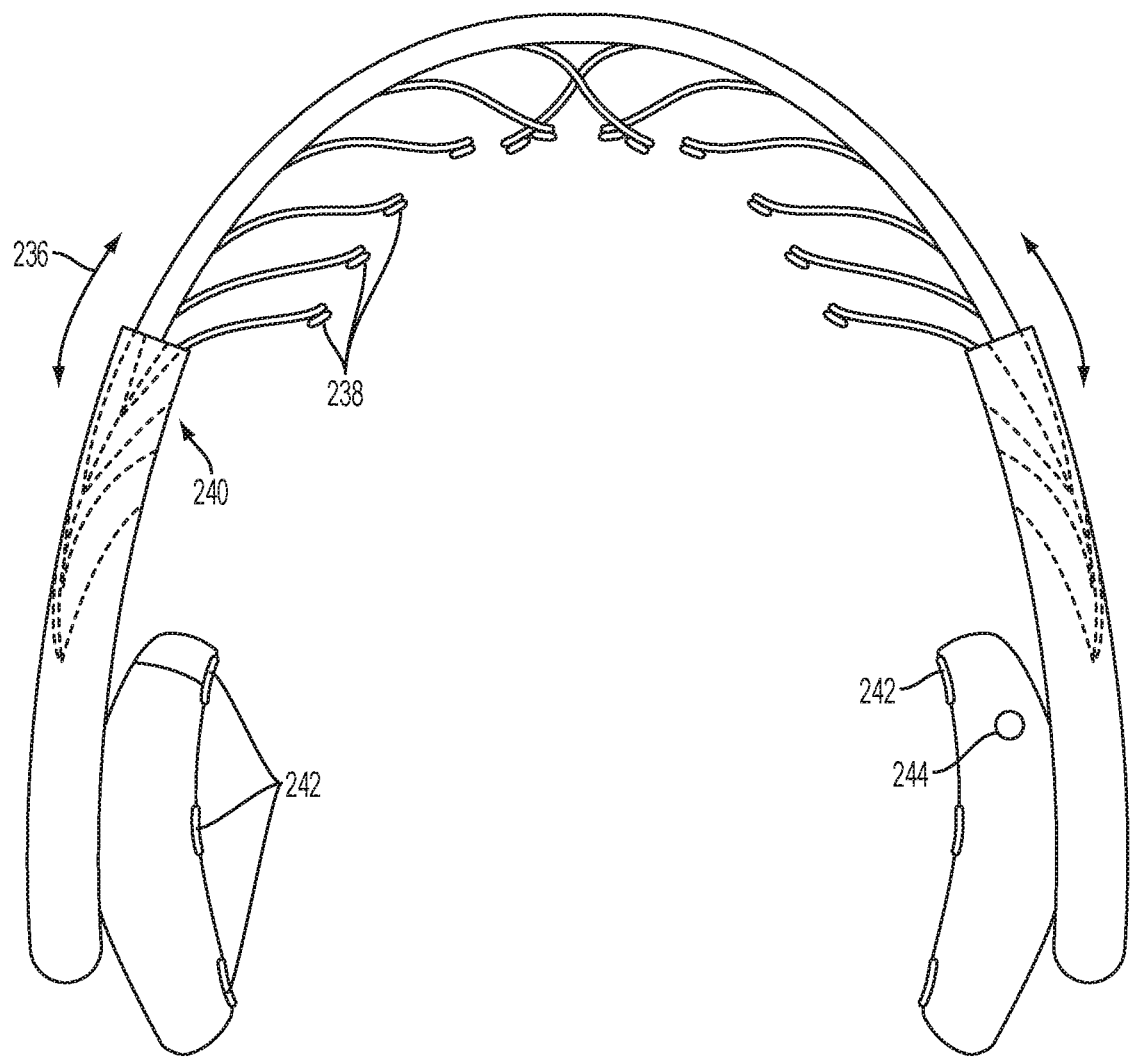
FIG. 61 is an example wearable apparatus.

FIG. 61 illustrates a further alternative embodiment of a band assembly with layered electrode petals 238, where the band assembly is to be worn on top of the head. This example band assembly connects with headphones 244. The headphones 244 have conductive ink on the surface to form electrodes 242. The band assembly includes an adjustable attachment 236 between arms of the headphones 244 and the band assembly to adjust to different lengths and fit different head sizes. The petal electrodes collapse into housing or arm of the headphones 242 at a portion 240 where the band assembly connects to the arms of the headphones 244.

Figure 62:
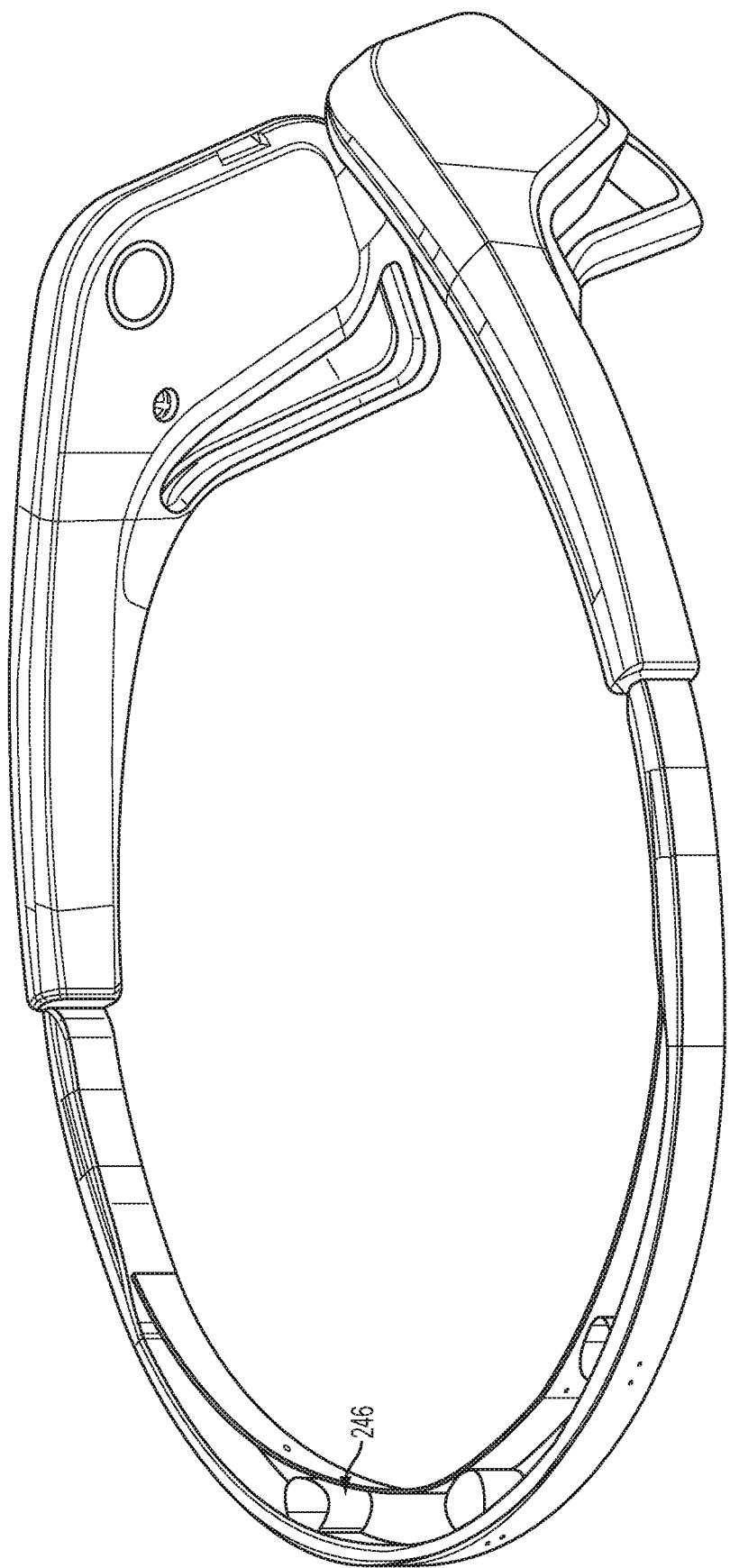
FIG. 62 is an example wearable apparatus.
Figure 64:
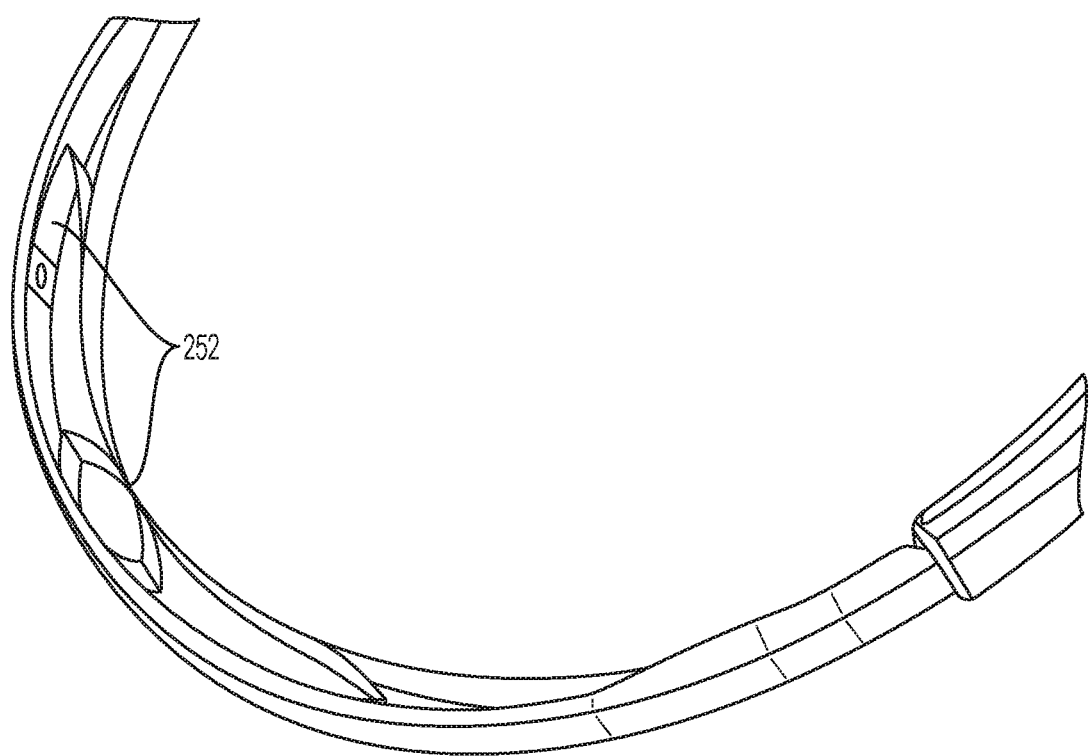
FIG. 64 is an example band assembly for a wearable apparatus.

As described, in an aspect, embodiments described herein may provide a band assembly with an inner band member and an outer band member. The band assembly may have a rigid, semi-circular outer band member and a flexible inner band member with a deformable attachment to the outer band member allowing the inner band member to conform to a user's forehead shape. For example, the inner band may attach to the outer band with a rubber spring strip as an example of a deformable attachment. The rubber spring strip provides a spring mechanism as the rubber compresses along its length when the headband is pulled tight to the head. The inner band may also be attached by a plastic, rubber or metal leaf spring as further examples of deformable attachments. Additional examples include a plastic, rubber or metal coil spring. The deformable attachment may also be foam. The arrangement of the springs are such that when placed on the head the deformable attachment provides a biasing component for pressure at the electrodes to ensure good contact with the head. FIGS. 62 and 64 show different example arrangements for the springs, with springs placed at a central sensor for the reference measurement (REF) and outer sensors for FP1 and FP2 measurements. The outer sensors may be the outer of five sensors of the band assembly. This arrangement of the springs may ensure the sensors have good contact with the head during use. FIG. 62 shows an example spring arrangement with circular, plastic or metal springs 246 behind the location of the outer sensors and the central sensor. FIG. 64 shows another example spring arrangement with a plastic of metal elliptical or leaf springs 252 including a middle spring.

Figure 65:
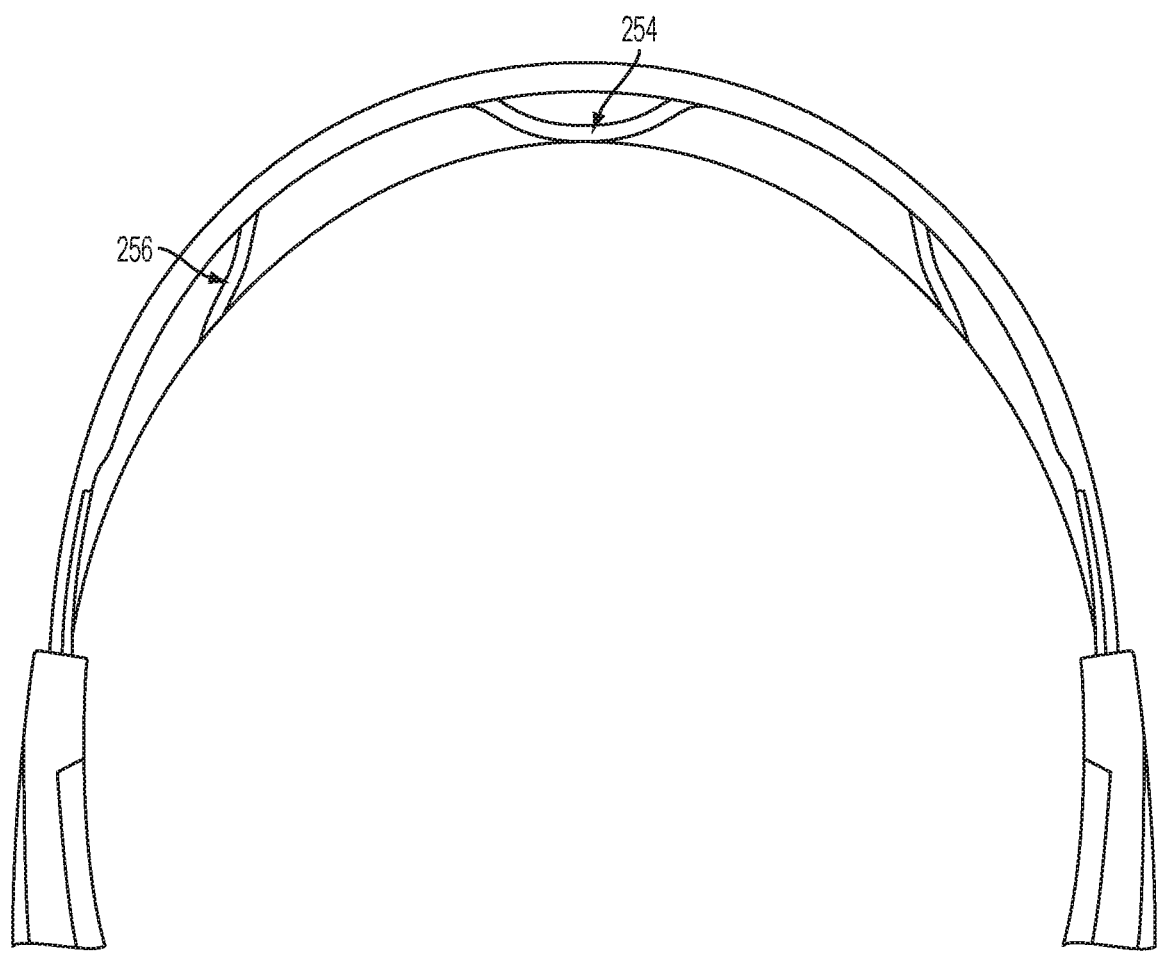
FIG. 65 is an example band assembly for a wearable apparatus.

FIG. 65 illustrates a schematic diagram of an example rubber spring strip that provides a suspension strip with side parts 256 that maintain contact between the sensors and the forehead of the user. The rubber spring strip may be referred to herein as a deformable attachment or a suspension strip. The rubber spring strip also includes a center portion 254 that provides pressure on the central sensor (e.g. REF electrode) and the forehead of the user. When the center portion 254 is compressed against the head, the side parts 256 are pulled towards the center.

Figure 66:
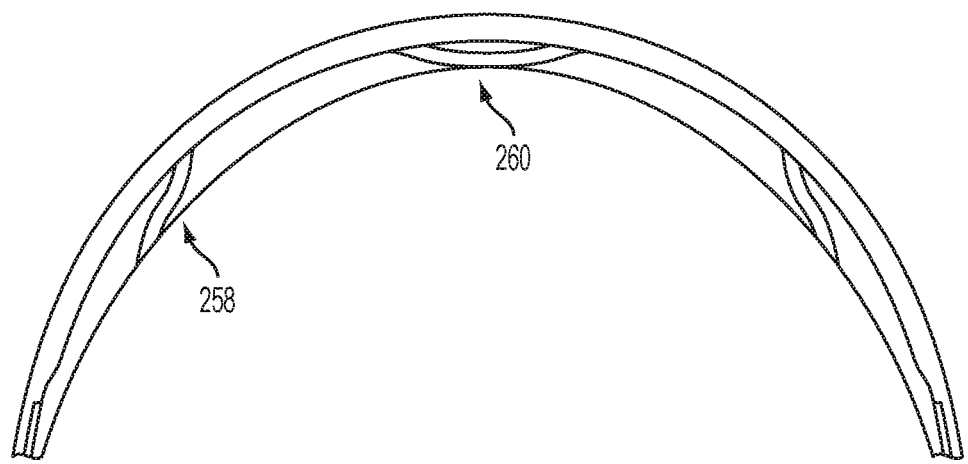
FIG. 66 is an example band assembly for a wearable apparatus.

FIG. 66 illustrates a schematic diagram of a further example rubber spring strip with side parts 258 and a center portion 260. The side parts of the suspension strip translate into a force directed against the user's forehead. The forehead pushing on the center portion 260 pulls the side parts 258 inward. The flex PCB may not stretch.

Figure 68:
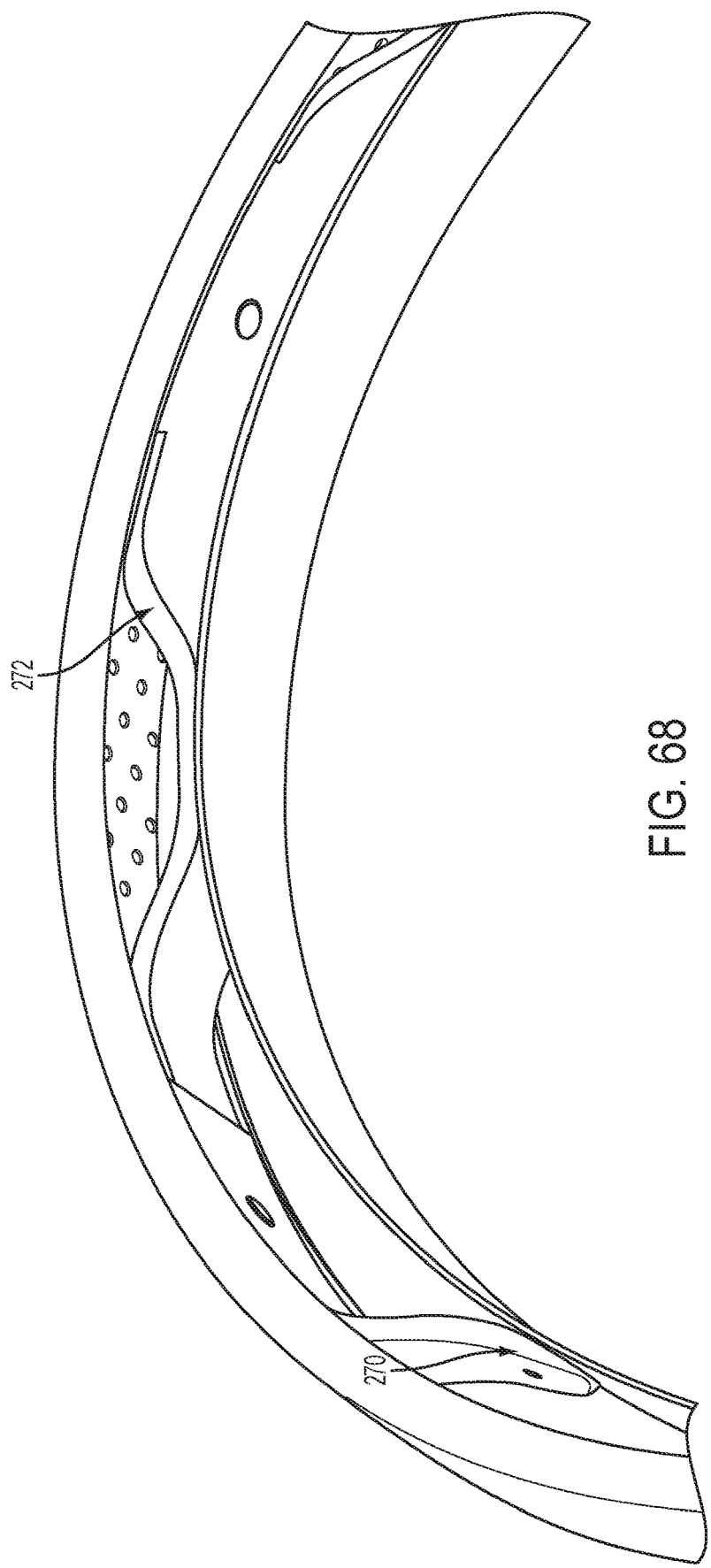
FIG. 68 is an example band assembly for a wearable apparatus.

FIG. 68 further illustrates a schematic diagram of a portion of the rubber spring strip with a first attachment point 270 and a second attachment point 272 connecting the inner band member and the outer band member. The spring force may be controlled for comfort by the thickness of the rubber, the durometer of the rubber, and the positioning of the attachment or glue points.

Embodiments described herein provide a flexible soft conductive surface (for skin contact) using a conductive coating that electronically connects to an electrical system for biosignal acquisition. The conductive coating may be provided by silver ink. The conductive coating may also be used for sensors on earpieces, as described herein.

As an illustrative example, the headband part of the wearable apparatus may contain five sensor connections to the head. As described, a center or central sensor may be the reference measurement (REF) to which all other measurements are taken. Two sensors to the side of the central sensor may be the contacts for the Driven Right Leg circuit, as described. This may reduce common mode noise by driving the body with a signal to cancel noise seen on reference measurement. The outer two sensor contacts may be EEG channels at FP1 and FP2 locations. The sensor contacts in the earpiece may be EEG channels at TP9 and TP12.

In accordance with some embodiments, the band assembly connects to one or more earpieces that contain sensors that may also be used to secure the band assembly. An earpiece may be a shaped conductive rubber piece that provides a good electrical connection to the user's ear to collect biosignal data. The earpiece is shaped to secure the band to the user's head or ear. The rubber ear piece deforms to hook onto the bottom of the ear to allow the user to apply pressure. The rubber ear piece could be open, closed and hollow, or solid. The rubber conforms around various ear sizes. The earpiece may contain an conductive coating of flexible silver ink.

In accordance with some embodiments, an earpiece may be removable and re-attachable. The ear piece may snap into a plastic ear pod. A removable earpiece may include a connection piece that mates with a mushroom head mounted on the ear pod. The mushroom heads match with mating connection pieces in the ear piece with sensor contacts.

Figure 63:
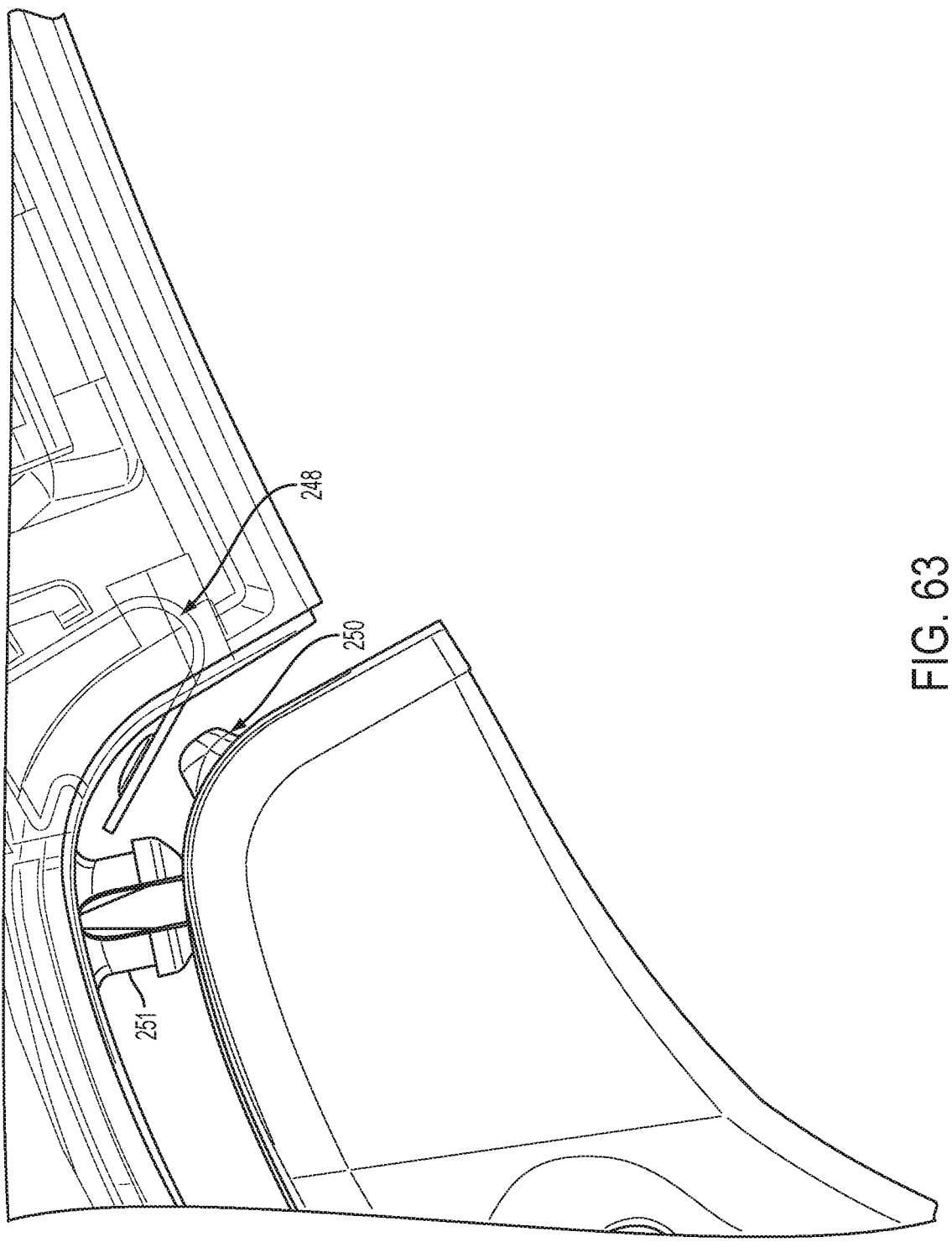
FIG. 63 is a portion of an example earpiece for a wearable apparatus.

Accordingly, one or more earpieces may be removably attached to the band assembly so that a user can swap earpieces. FIG. 63 illustrates details of an ear connection including a mushroom head 251 on an ear pod that removable attaches to an ear piece with a sensor contact portion. A gold plated spring 248 contacts and a nub 250 on chrome plated plastic of the ear piece to electrically connect the ear piece sensors to the ear pod with computer system.

Figure 72:
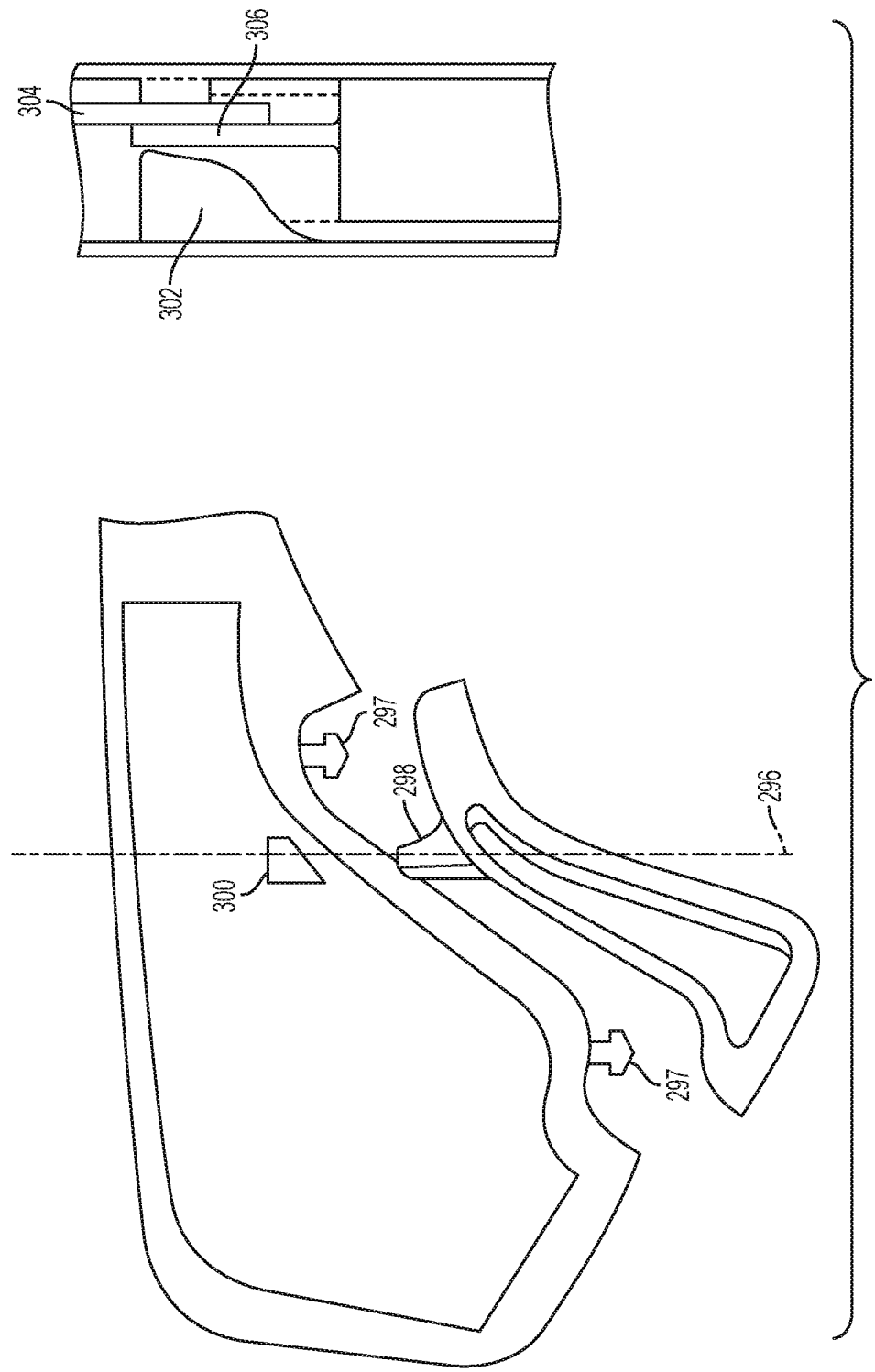
FIG. 72 is an example earpiece for a wearable apparatus.

FIG. 72 illustrates further details of an ear pod attachment. The ear pod includes mushroom heads 297 for connecting to the removable ear piece with the sensor contact area. The ear pod includes a gold contact 300 on a PCB that contacts a conductive spur 298 on the ear piece to establish an electrical connection. A cross section view taken at position 296 illustrates an alternate view of the conductive spur 306 of ear piece with sensor contact in contact with the PCB 304 of the ear pod. Features of the plastic case of the ear pod forces the spur 306 against the gold contact 302.

Figure 67:
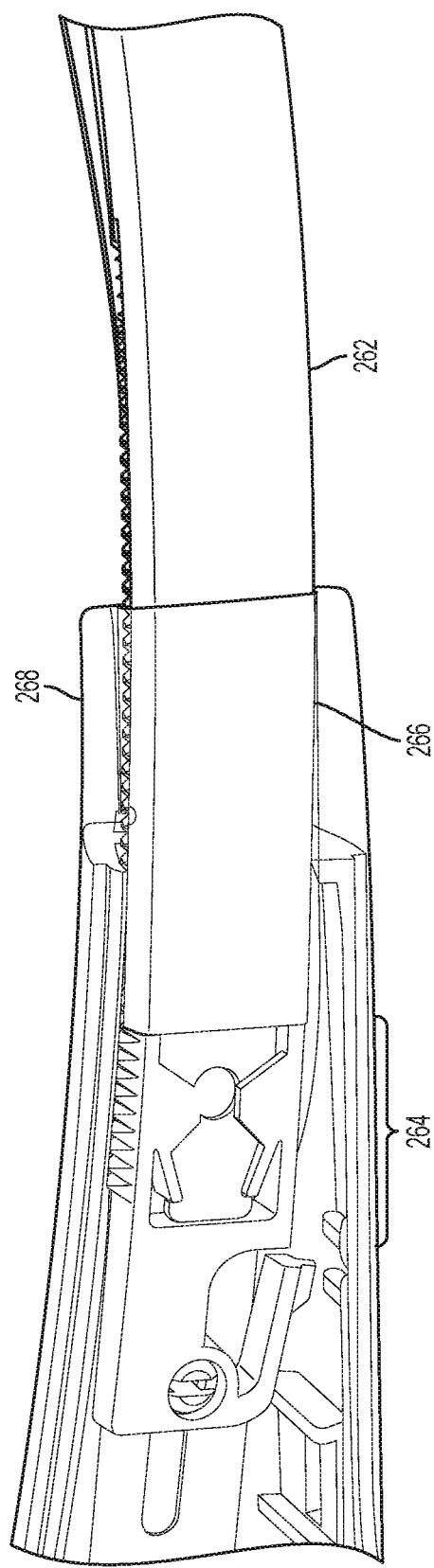
FIG. 67 is an example band assembly for a wearable apparatus.

In accordance with some embodiments, the headband may be adjustable to fit different head sizes. The headband may have an adjustable length. For example, the headband can extend or retract into the ear pods, as shown by the area of adjustment in FIG. 44. This allows the headband to adjust length for different distances between user's ears along the surface of the head based on the overall size of the head. FIG. 67 illustrates an example adjustable slider connection between the band assembly and the ear pod. An ear pod arm 268 may define a receiving slot 266 to receive an end portion 262 of the band assembly. A ratchet mechanism may be used to secure the end portion 262 of the band assembly at different positions 264 within the arm 268 to extend or retract into the ear pods.

FIG. 70 illustrates a schematic of a shorter length for the adjustable headband to fit a small head, and a longer length for the adjustable headband to fit a large head. The end portion 280 of the band assembly may be configured with teeth to interact with a ratchet mechanism in the ear pod to control headband length. A fold portion 282 in the Flex PCB in the ear pod allows for an extendible electrical circuit. When a portion 284 of the Flex PCB is extended that radius in the flex may still be within specification. The outer band member may be springy to get a rough shape of the forehead. The inner band member may include the Flex PCB that follows head contours.

Figure 71:
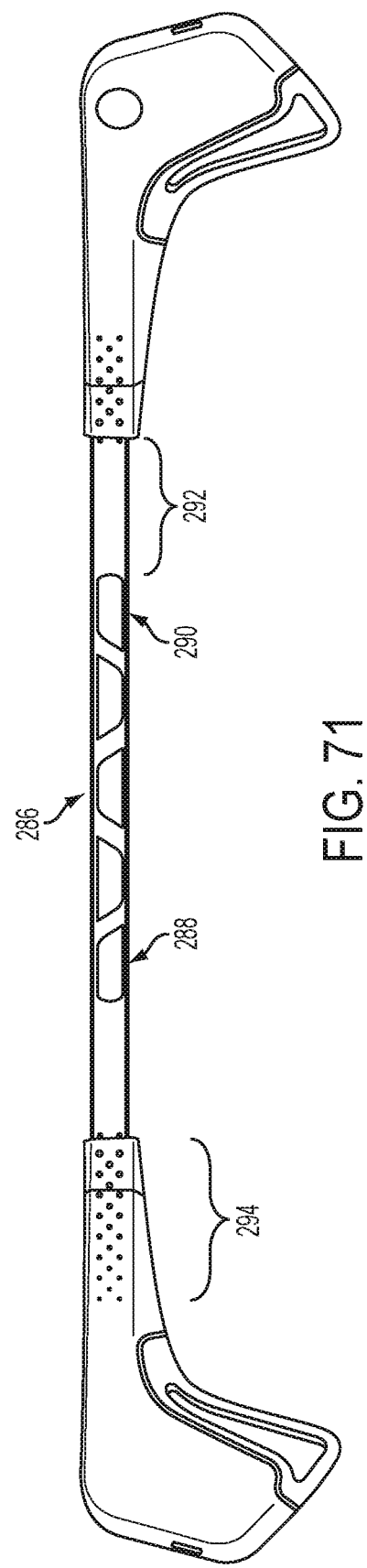
FIG. 71 is an example wearable apparatus.

FIG. 71 shows an adjustable headband 286 with an area of adjustment 294 for the length. A portion 292 may separate the area of adjustment 294 from the sensor contact portion so that it does not retract into the ear pod and maintains proximity from ear area. An example sensor arrangement or position is shown. The sensor contact portion may include a center electrode used as a reference as the center of the headband may have good contact with the user's forehead. The sensor contact portion may also include outer electrodes 288, 290 that may be referred to as FP1 and FP2 position electrodes which may be positioned to maximize the distance between them without allowing proximity to the ear pod which may impact ability to make good contact with the user's head.

Figure 73:
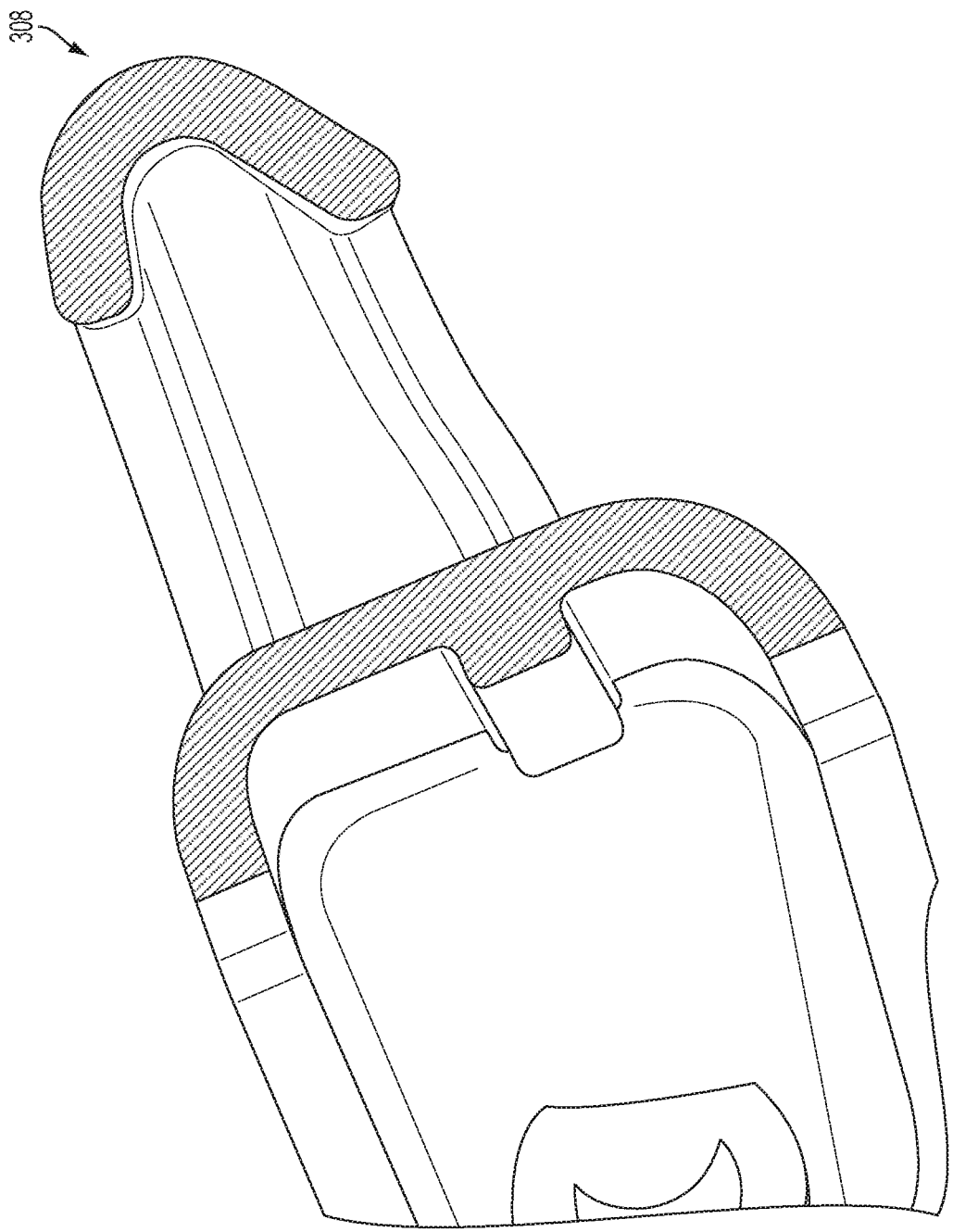
FIG. 73 is an example earpiece for a wearable apparatus.

FIG. 73 shows a triangular or V shape portion 308 of ear piece rubber that is designed to fit into the groove behind the ear and provide comfort and good electrical sensor contact.

FIG. 74 shows a further schematic of the adjustable headband with a deformable rubber ear piece. The band assembly has an end portion 316 with teeth that interact with teeth on top and bottom of a receiving slot in the arm of the ear pod to ratchet band assembly into the ear pod and adjust the length.

Figure 69:
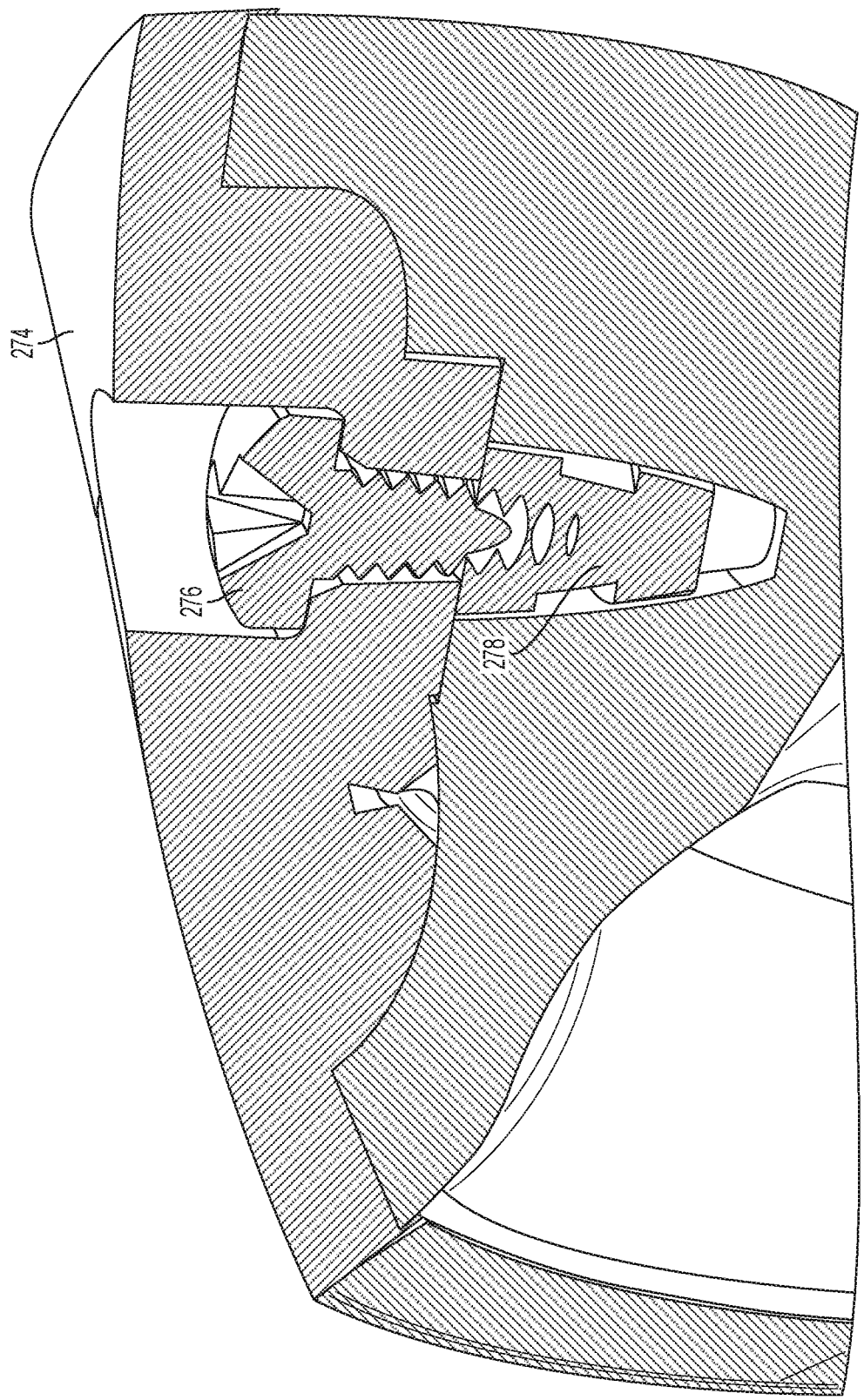
FIG. 69 is an example earpiece for a wearable apparatus.

FIG. 69 illustrates a portion of a rubber ear piece with an electrical connection. The rubber ear piece includes a chrome plated plastic layer 274. A gold screw 276 connects with a brass threaded insert 278 molded into conductive rubber.

In addition to having an adjustable length, the headband is also flexible and can twist allowing adjustment for different shaped heads. The rubber ear contacts provide mechanical holding on the back of the ears to allow for tightening of the headband as needed.

Embodiments described herein may improve wearability for the headband using the adjustment features. Further, the arrangement of springs, as described herein may improve wearability of the headband.

FIG. 74 illustrates a deformable, conductive ear piece 314 that provides both the electrical sensor contact for an EEG channel and structural means for attaching or securing to the user's head. The ear piece with sensor contact includes a hollow area 312 and being open allows the ear piece to form around the back of the ear, distributing pressure to make it more comfortable to wear and maximizing electrical contact. A mechanical holding 310 of the ear piece 314 may deform to hook onto the user's ear and allow the headband to tighten on head. The ear piece 314 may be removable from the ear pod, as described herein. The ear piece 314 may be made of a conductive material such as carbon filled rubber. The ear piece 314 may be coated in a flexible conductive material, such as silver ink.

In another aspect, there is provided a process for ensuring good connection of silver to Flex PCB traces. As described, silver ink may be used as a conductive coating for sensors. Silver ink may provide a flexible conductive ink that is designed to bond with polyamide surfaces. For example, the silver ink may be the coating on the rubber used for the ear contacts. The silver ink may be a flexible and stretchable conductive ink intended for use in creating circuits on fabrics. It may bond to polyurethane and polyester substances. Silver ink may not adhere well to either copper or gold. To form a good connection between silver ink sensor contacts and the Flex PCB traces a hatched pattern of copper is created. The process further involves creating holes in the polyamide coverlay over the copper pattern. The process may further involve gold plating the copper and printing the silver ink onto the flex PCB so that the adhesion between the polyimide coverlay and the silver ink keeps the silver ink on the flex PCB and the cohesive strength of the ink keeps it in contact with the gold plated copper.

It will be appreciated that any module or component exemplified herein that executes instructions may include or otherwise have access to computer readable media such as storage media, computer storage media, or data storage devices (removable and/or non-removable) such as, for example, magnetic disks, optical disks, tape, and other forms of computer readable media. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD), blue-ray disks, or other optical storage, magnetic cassettes, magnetic tape, magnetic disk storage or other magnetic storage devices, or any other medium which can be used to store the desired information and which can be accessed by an application, module, or both. Any such computer storage media may be part of the mobile device, tracking module, object tracking application, etc., or accessible or connectable thereto. Any application or module herein described may be implemented using computer readable/executable instructions that may be stored or otherwise held by such computer readable media.

Thus, alterations, modifications and variations can be effected to the particular embodiments by those of skill in the art without departing from the scope of this disclosure, which is defined solely by the claims appended hereto.

In further aspects, the disclosure provides systems, devices, methods, and computer programming products, including non-transient machine-readable instruction sets, for use in implementing such methods and enabling the functionality described previously.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

Except to the extent explicitly stated or inherent within the processes described, including any optional steps or components thereof, no required order, sequence, or combination is intended or implied. As will be will be understood by those skilled in the relevant arts, with respect to both processes and any systems, devices, etc., described herein, a wide range of variations is possible, and even advantageous, in various circumstances, without departing from the scope of the invention, which is to be limited only by the claims.

What is claimed is:

1. A wearable apparatus for wearing on a head of a user, the apparatus comprising: a band assembly comprising:
    a flexible band member comprising band ends joined by a curved band portion of a curve generally shaped to correspond to the user's forehead;
    at least one bio-signal sensor disposed inwardly along the curved band portion to provide a flexible conductive surface;
    a biasing component to urge the at least one bio-signal sensor towards the user's forehead when worn by the user;
    a conformable earpiece connected to one of the band ends of the flexible band member to secure the wearable apparatus to the user, wherein at least a portion of the conformable earpiece is made of conductive material to provide at least one additional bio-signal sensor in contact with an ear or mastoid bone region of the user to form around the back of the ear of the user, wherein the conformable earpiece has a depressible area to depress the conductive material against the back of the ear at a front edge and hook a bottom edge of the conformable earpiece around the ear to generate a force to secure the conductive material against the back of the ear and to urge the at least one bio-signal sensor towards the user's forehead, wherein the conformable earpiece comprises a collapsible inner hollow area configured to collapse to form around the back of the ear when worn;
    at least one computer system connected to the at least one bio-signal sensor and the at least one additional bio-signal sensor to receive bio-signal data to determine a brain state of the user, the at least one computer system having at least one computer, at least one non-transitory computer readable medium including processing instructions for the computer processor to process the bio-signal data, and at least one communication subsystem for communicating the processed bio-signal data to an external computing device.

2. The wearable apparatus of claim 1, wherein the at least one bio-signal sensor comprises at least a central brainwave sensor at a centre portion of the curved band portion and two outer brainwave sensors, each of the outer brainwave sensors arranged on a respective side of the central brainwave sensor.

3. The wearable apparatus of claim 1, wherein the conformable earpiece has a wrap portion to wrap a contact portion under the user's ear.

4. The wearable apparatus of claim 1, further comprising at least one adjustable component connecting the band assembly to the conformable earpiece, at least one adjustable component being extendable or retractable in relation to the at least one earpiece to extend or retract a length of the band assembly.

5. The wearable apparatus of claim 1, wherein the at least one computer system is connected to the at least one bio-signal sensor and the at least one additional bio-signal sensor by communication wires integrated into the band assembly.

6. The wearable apparatus of claim 1, wherein the at least one computer system has a port for connecting the wearable apparatus to a power source for charging or for interfacing the wearable apparatus with the external computing device or additional elements electrical elements.

7. The wearable apparatus of claim 1, wherein the conformable earpiece supports the wearable apparatus on the head.

8. The wearable apparatus of claim 1, wherein the conformable earpiece has a bottom portion being a contact portion having the at least one additional bio-signal sensor, the bottom portion having a front edge and a bottom edge, the front edge shaped to form to the user's ear, the bottom edge being shaped to wrap under the user's ear.

9. The wearable apparatus of claim 1, wherein the at least one bio-signal sensor and the additional bio-signal sensor comprises a reference sensor providing a reference measurement for other bio-signal measurements, a Driven Right Leg sensor to reduce noise of the reference measurement, at least two sensors for providing EEG channel measurements at FP1 and FP2 locations, and at least two sensors for providing EEG channel measurements at TP9 and TP12 locations.

10. The wearable apparatus of claim 9, wherein the reference sensor is a central brainwave sensor providing the reference measurement.

11. The wearable apparatus of claim 1, wherein the at least one conformable earpiece is removable from the wearable apparatus and comprises a mushroom head with an attachment device that mates with a corresponding attachment device of the wearable apparatus.

12. The wearable apparatus of claim 1, wherein the conformable earpiece comprises a mechanical holding on the a back of the conformable earpiece to tighten the band assembly.

13. The wearable apparatus of claim 1, wherein the band assembly is stretchable to adjust the curve of the curved band portion.

14. The wearable apparatus of claim 1, further comprising a flexible conductive coating on the conformable earpiece to provide the at least one additional bio-signal sensor.

15. The wearable apparatus of claim 1, wherein the at least one bio-signal sensor has a conductive coating that connects to a flexible circuit in the computer system.

16. The wearable apparatus of claim 1, wherein the at least one bio-signal sensor comprises a hydrogel that has been hydrated with a conductive solution.

17. The wearable apparatus of claim 1, wherein the band member comprises stretchable material.

18. The wearable apparatus of claim 1, further comprising a semi-rigid attachment with the at least one bio-signal sensor being attachable to the headband at a plurality of locations.

19. The wearable apparatus of claim 1, wherein the conformable earpiece has a receiving slot to receive the band member and has an attachment component to secure the band member to the conformable earpiece at a plurality of positions to adjust the length of the wearable apparatus.

20. The wearable apparatus of claim 1, wherein the conformable earpiece further comprises a mechanical holding of the earpiece configured to deform to hook onto the ear of the user and allow the headband to tighten on the head.

* * * * *